US012807707B2

(12) United States Patent
Serrero

(10) Patent No.: US 12,807,707 B2
(45) **Date of Patent: *Nov. 24, 2026**

(54) MONOCLONAL ANTIBODIES AND CONJUGATES AGAINST PROSTAGLANDIN F2 RECEPTOR INHIBITOR AND USES THEREOF

(71) Applicant: A & G Pharmaceutical, Inc., Columbia, MD (US)

(72) Inventor: Ginette Serrero, Ellicott City, MD (US)

(73) Assignee: A & G Pharmaceutical, Inc., Columbia, MD (US)

( * ) Notice: Subject to any disclaimer, the term of this patent is extended or adjusted under 35 U.S.C. 154(b) by 215 days.

This patent is subject to a terminal disclaimer.

(21) Appl. No.: 18/078,378

(22) Filed: Dec. 9, 2022

(65) Prior Publication Data

US 2024/0199738 A1 Jun. 20, 2024

Related U.S. Application Data

(63) Continuation of application No. 16/755,685, filed as application No. PCT/US2018/055905 on Oct. 15, 2018, now Pat. No. 11,555,074.

(60) Provisional application No. 62/571,961, filed on Oct. 13, 2017.

(51) Int. Cl.
*C07K 16/28* (2006.01)

(52) U.S. Cl.
CPC .... *C07K 16/2803* (2013.01); *C07K 2317/565* (2013.01); *C07K 2317/73* (2013.01)

(58) Field of Classification Search
CPC .................................................. C07K 16/2803
USPC ....................................................... 424/133.1
See application file for complete search history.

(56) References Cited

U.S. PATENT DOCUMENTS

| | | | | |
|---|---|---|---|---|
| 11,555,074 B2 * | 1/2023 | Serrero | .................. | C07K 16/30 |
| 2011/0059107 A1 | 3/2011 | Allison et al. | | |
| 2013/0236467 A1 | 9/2013 | Griggs et al. | | |
| 2016/0151515 A1 | 6/2016 | Joubert et al. | | |
| 2026/0132218 A1 * | 5/2026 | Serrero | .................. | C07K 16/32 |

FOREIGN PATENT DOCUMENTS

| | | |
|---|---|---|
| WO | 2024081905 A2 * | 4/2024 |
| WO | 2024215624 A2 * | 10/2024 |

OTHER PUBLICATIONS

Marquez et al (PLoS ONE 16(1): e0246197).*
Marquez et al (ACS Omega Mar. 15, 2024;9(12):14381-14387. doi: 10.1021/acsomega.4c00042. eCollection Mar. 26, 2024).*
Marquez et al (J Cell Biochem Aug. 2024;125(8):e30616. doi: 10.1002/jcb.30616. Epub Jun. 24, 2024).*
George et al. (Circulation. 1998; 97: 900-906).
Krah et al. (Immunopharmacology and Immunotoxicology, 38:1, 21-28 (2016)).
Kim et al. (Biochimica et Biophysica Acta 1844 (2014) 1983-2001).
Almagro & Franssen (Frontiers in Bioscience, 13:1619-33 (2008)).
Edwards et al., J. Mol Biol 334:103-118 (2003).
Marchalonis et al., Dev & Comp Immunol. 30:223-247 (2006).
Lippow et al., Nature Biotechnology, 25(10):1171-1176 (2007).
Sulea et al., Scientific Reports, 8(260):1-11 (2018).
Hasegawa et al., MABS, vol. 9, No. 5, pp. 854-873 (2017).
Altshuler et al., Biochemistry (Moscow), 75(13):1584-1605 (2010) at p. 1600, col. 1, para. 2, lines 1-5.
Vajda et al., Current Opinion in Structural Biology, 67 pp. 226-231 (2021).
Marks et al., J. Biol. Chem. 295(29) 9823-9837 (2020).
Akbar et al., (Cell Reports 34, 108856, Mar. 16, 2021).
Lo et al., BMC Genomics vol. 22, Article No. 116 (2021).
Marquez et al (PLoS ONE 16(1): e0246197 (2021)).
Marquez et al (Cancer Research, (Jul. 2021) vol. 81, No. 13 Suppl. Abstract No. LB116. Meeting Info: AACR Annual Meeting 2021. Philadelphia, PA, United States. May 17, 2021-May 21, 2021).
International Search Report and Written Opinion; International Application No. PCT/US2018/055905; Feb. 27, 2019.
International Preliminary Report on Patentability; International Application No. PCT/US2018/055905; Apr. 14, 2020.
S. Charrin et al., "The Major CD9 and CD81 Molecular Partner-Identification and Characterization of the Complexes", The Journal of Biological Chemistry, Apr. 2001, vol. 276, No. 17, pp. 14329-14337.
Al. Goenaga et al., "Identification and characterization of tumor antigens by using antibody phage display and intrabody strategies", Molecular Immunology, Jul. 2007, vol. 44, No. 15, pp. 3777-3788.
W. Guilmain et al., "CD9P-1 expression correlates with the metastatic status of lung cancer, and a truncated form of CD9P-1, GS-168AT2, inhibits in vivo tumour growth", British Journal of Cancer, 2011, vol. 104, pp. 496-504.
Y. Zhou et al., "Internalizing Cancer Antibodies from Phage Libraries Selected on Tumor Cells and Yeast-Displayed Tumor Antigens", Journal of Molecular Biology, 2010, vol. 404, pp. 88-99.

* cited by examiner

*Primary Examiner* — Lynn A Bristol
(74) *Attorney, Agent, or Firm* — Farber LLC

(57) ABSTRACT

The present disclosure provides an antibody, antigen binding fragment thereof, or an antibody conjugate thereof, useful in methods for treatment or diagnosis of conditions characterized by the expression of PTGFRN. The antibodies or antigen binding fragments thereof may also be used in imaging or detecting cells that express PTGFRN.

29 Claims, 20 Drawing Sheets

Specification includes a Sequence Listing.

Control

Transfected

4°C

37°C

4F4 binding at 4ºC 1 h.

4F4 internalization at 37ºC 1 h.

HEK cells - Human embryonic kidney cells overexpressing PTGFRN

DAOY cells – human medulloblastoma

A431 cells: Human epidermoid carcinoma (H/N)

Negative /low control slide
(Hek293 CD )

Positive control slide
(A431 cells)

Benign pleural mesothelioma

Malignant pleural mesothelioma

Histogram of mIgG and 4F4 (right peak) against DAOY Cells

| Calibration beads | ABC | MFI |
|---|---|---|
| 1 | 1,900 | 5.91 |
| 2 | 8,100 | 29.7 |
| 3 | 40,000 | 138 |
| 4 | 225,000 | 482 |
| 5 | 799,000 | 1631 |

Antibodies per cell line

Cell lines per Antibody

Figure 18

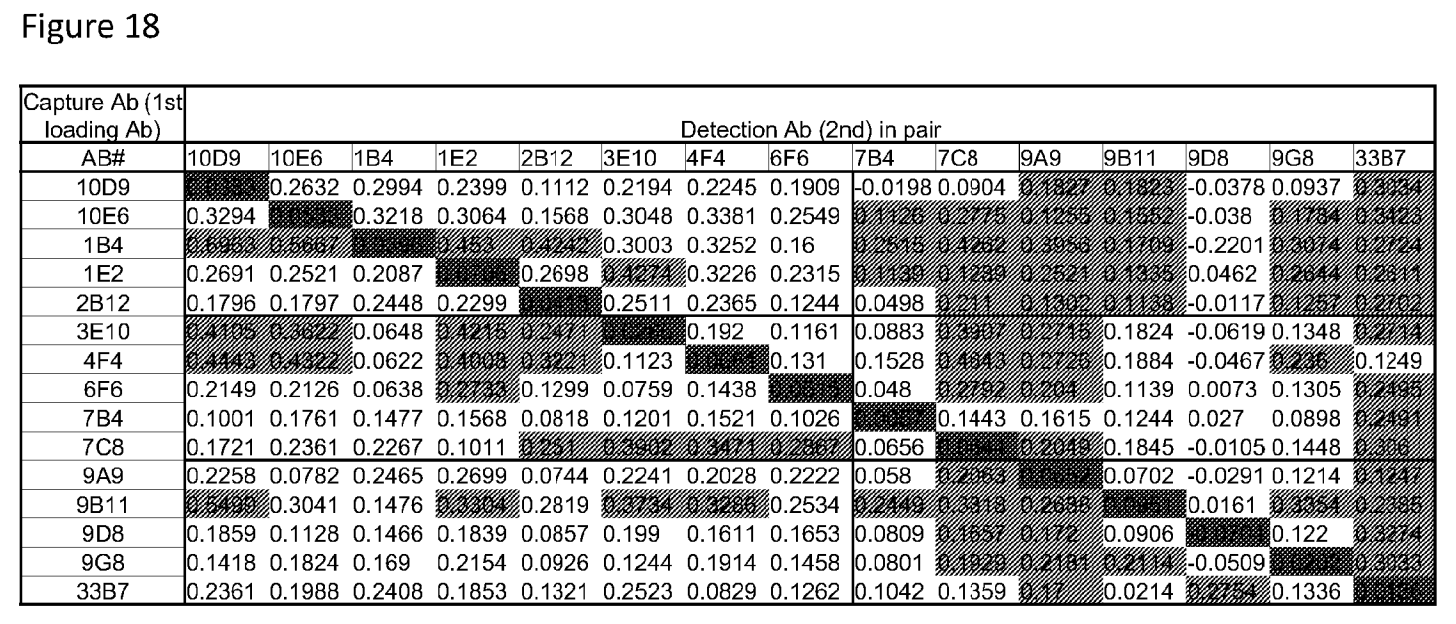

| Capture Ab (1st loading Ab) | Detection Ab (2nd) in pair | | | | | | | | | | | | | | |
|---|---|---|---|---|---|---|---|---|---|---|---|---|---|---|---|
| AB# | 10D9 | 10E6 | 1B4 | 1E2 | 2B12 | 3E10 | 4F4 | 6F6 | 7B4 | 7C8 | 9A9 | 9B11 | 9D8 | 9G8 | 33B7 |
| 10D9 | [illegible] | 0.2632 | 0.2994 | 0.2399 | 0.1112 | 0.2194 | 0.2245 | 0.1909 | -0.0198 | 0.0904 | 0.1827 | 0.1823 | -0.0378 | 0.0937 | 0.3034 |
| 10E6 | 0.3294 | [illegible] | 0.3218 | 0.3064 | 0.1568 | 0.3048 | 0.3381 | 0.2549 | 0.1126 | 0.2775 | 0.1255 | 0.1552 | -0.038 | 0.1784 | 0.3423 |
| 1B4 | 0.6963 | 0.5667 | [illegible] | 0.453 | 0.4242 | 0.3003 | 0.3252 | 0.16 | 0.2515 | 0.4262 | 0.3956 | 0.1709 | -0.2201 | 0.3074 | 0.2724 |
| 1E2 | 0.2691 | 0.2521 | 0.2087 | [illegible] | 0.2698 | 0.4274 | 0.3226 | 0.2315 | 0.1139 | 0.1239 | 0.2521 | 0.1335 | 0.0462 | 0.2644 | 0.2611 |
| 2B12 | 0.1796 | 0.1797 | 0.2448 | 0.2299 | [illegible] | 0.2511 | 0.2365 | 0.1244 | 0.0498 | 0.211 | 0.1302 | 0.1138 | -0.0117 | 0.1257 | 0.2702 |
| 3E10 | 0.4105 | 0.3622 | 0.0648 | 0.4215 | 0.2471 | [illegible] | 0.192 | 0.1161 | 0.0883 | 0.3907 | 0.2715 | 0.1824 | -0.0619 | 0.1348 | 0.2714 |
| 4F4 | 0.4443 | 0.4322 | 0.0622 | 0.4008 | 0.3221 | 0.1123 | [illegible] | 0.131 | 0.1528 | 0.4643 | 0.2726 | 0.1884 | -0.0467 | 0.236 | 0.1249 |
| 6F6 | 0.2149 | 0.2126 | 0.0638 | 0.2733 | 0.1299 | 0.0759 | 0.1438 | [illegible] | 0.048 | 0.2792 | 0.204 | 0.1139 | 0.0073 | 0.1305 | 0.2495 |
| 7B4 | 0.1001 | 0.1761 | 0.1477 | 0.1568 | 0.0818 | 0.1201 | 0.1521 | 0.1026 | [illegible] | 0.1443 | 0.1615 | 0.1244 | 0.027 | 0.0898 | 0.2491 |
| 7C8 | 0.1721 | 0.2361 | 0.2267 | 0.1011 | 0.251 | 0.3902 | 0.3471 | 0.2867 | 0.0656 | [illegible] | 0.2049 | 0.1845 | -0.0105 | 0.1448 | 0.306 |
| 9A9 | 0.2258 | 0.0782 | 0.2465 | 0.2699 | 0.0744 | 0.2241 | 0.2028 | 0.2222 | 0.058 | 0.2063 | [illegible] | 0.0702 | -0.0291 | 0.1214 | 0.1247 |
| 9B11 | 0.5499 | 0.3041 | 0.1476 | 0.3304 | 0.2819 | 0.3734 | 0.3286 | 0.2534 | 0.2449 | 0.3318 | 0.2686 | [illegible] | 0.0161 | 0.3354 | 0.2385 |
| 9D8 | 0.1859 | 0.1128 | 0.1466 | 0.1839 | 0.0857 | 0.199 | 0.1611 | 0.1653 | 0.0809 | 0.1657 | 0.172 | 0.0906 | [illegible] | 0.122 | 0.3274 |
| 9G8 | 0.1418 | 0.1824 | 0.169 | 0.2154 | 0.0926 | 0.1244 | 0.1914 | 0.1458 | 0.0801 | 0.1929 | 0.2181 | 0.2114 | -0.0509 | [illegible] | 0.3033 |
| 33B7 | 0.2361 | 0.1988 | 0.2408 | 0.1853 | 0.1321 | 0.2523 | 0.0829 | 0.1262 | 0.1042 | 0.1359 | 0.17 | 0.0214 | 0.2754 | 0.1336 | [illegible] |

SEQUENCE LISTING

```
Sequence total quantity: 160
SEQ ID NO: 1           moltype = DNA  length = 336
FEATURE                Location/Qualifiers
source                 1..336
                       mol_type = genomic DNA
                       organism = Mus musculus
SEQUENCE: 1
gacattgtga tgtcacagtc tccatcctcc ctagctgtgt cagttggaga gaaggttact  60
atgagctgca agtccagtca gagcctttta tatagtacca atcaaaagaa ctacttagcc  120
tggtaccagc agaaaccagg gcagtctcct aaaccgctga tttactgggc atccactagg  180
gaatctgggg tccctgatcg cttcacaggc agtgggtctg ggacagattt cactctcacc  240
atcagcagtg tgaaggctga agacctggca gtttattact gtcagcaata ttatagttat  300
cggacgttcg gtggaggcac caagctggaa atcaaa                            336

SEQ ID NO: 2           moltype = AA  length = 130
FEATURE                Location/Qualifiers
source                 1..130
                       mol_type = protein
                       organism = Mus musculus
SEQUENCE: 2
DIVMSQSPSS LAVSVGEKVT MSCKSSQSLL YSTNQKNYLA WYQQKPGQSP KPLIYWASTR  60
ESGVPDRFTG SGSGTDFTLT ISSVKAEDLA VYYCQQYYSY RTFGGGTKLE IKRADAAPTV  120
SIFPPSSKLG                                                         130

SEQ ID NO: 3           moltype = DNA  length = 357
FEATURE                Location/Qualifiers
source                 1..357
                       mol_type = genomic DNA
                       organism = Mus musculus
SEQUENCE: 3
gatgtacagc ttcaggagtc aggacctggc ctcgtgaaac cttctcagtc tctgtctctg  60
acctgctctg tcactggctg ctccatcacc agtggttatt attggaactg gatccggcag  120
tttccaggaa acaaactgga atggatgggc tacataagcc acgatggtaa caataactac  180
agcccatctc tcaaaaatcg aatctccatc actcgtgaca catctaagaa ccagtttttc  240
ctgaagttga actctgtgac tactgaggac acagccacat attactgtgc aagaggattt  300
tattactacg gttactttgg ctactggggc caaggcacca ctctcacagt ctccagc     357

SEQ ID NO: 4           moltype = AA  length = 135
FEATURE                Location/Qualifiers
source                 1..135
                       mol_type = protein
                       organism = Mus musculus
SEQUENCE: 4
DVQLQESGPG LVKPSQSLSL TCSVTGCSIT SGYYWNWIRQ FPGNKLEWMG YISHDGNNNY  60
SPSLKNRISI TRDTSKNQFF LKLNSVTTED TATYYCARGF YYYGYFGYWG QGTTLTVSSA  120
KTTPPSVYPL VPGSL                                                   135

SEQ ID NO: 5           moltype = AA  length = 17
FEATURE                Location/Qualifiers
source                 1..17
                       mol_type = protein
                       organism = Mus musculus
SEQUENCE: 5
KSSQSLLYST NQKNYLA                                                 17

SEQ ID NO: 6           moltype = AA  length = 7
FEATURE                Location/Qualifiers
source                 1..7
                       mol_type = protein
                       organism = Mus musculus
SEQUENCE: 6
```

```
WASTRES                                                        7

SEQ ID NO: 7           moltype = AA  length = 8
FEATURE                Location/Qualifiers
source                 1..8
                       mol_type = protein
                       organism = Mus musculus
SEQUENCE: 7
QQYYSYRT                                                       8

SEQ ID NO: 8           moltype = AA  length = 11
FEATURE                Location/Qualifiers
source                 1..11
                       mol_type = protein
                       organism = Mus musculus
SEQUENCE: 8
GCSITSGYYW N                                                   11

SEQ ID NO: 9           moltype = AA  length = 16
FEATURE                Location/Qualifiers
source                 1..16
                       mol_type = protein
                       organism = Mus musculus
SEQUENCE: 9
YISHDGNNNY SPSLKN                                              16

SEQ ID NO: 10          moltype = AA  length = 10
FEATURE                Location/Qualifiers
source                 1..10
                       mol_type = protein
                       organism = Mus musculus
SEQUENCE: 10
GFYYYGYFGY                                                     10

SEQ ID NO: 11          moltype = AA  length = 7
FEATURE                Location/Qualifiers
source                 1..7
                       mol_type = protein
                       organism = Mus musculus
SEQUENCE: 11
GYTFTGY                                                        7

SEQ ID NO: 12          moltype = AA  length = 6
FEATURE                Location/Qualifiers
source                 1..6
                       mol_type = protein
                       organism = Mus musculus
SEQUENCE: 12
LPGSGS                                                         6

SEQ ID NO: 13          moltype = AA  length = 9
FEATURE                Location/Qualifiers
source                 1..9
                       mol_type = protein
                       organism = Mus musculus
SEQUENCE: 13
RRRSYYFDY                                                      9

SEQ ID NO: 14          moltype = AA  length = 7
FEATURE                Location/Qualifiers
source                 1..7
                       mol_type = protein
                       organism = Mus musculus
SEQUENCE: 14
GYTFTTY                                                        7

SEQ ID NO: 15          moltype = AA  length = 6
FEATURE                Location/Qualifiers
source                 1..6
                       mol_type = protein
                       organism = Mus musculus
SEQUENCE: 15
NTYSGV                                                         6

SEQ ID NO: 16          moltype = AA  length = 9
FEATURE                Location/Qualifiers
source                 1..9
                       mol_type = protein
                       organism = Mus musculus
```

-continued

```
SEQUENCE: 16
GTGFYAMDC                                                         9

SEQ ID NO: 17          moltype = AA  length = 11
FEATURE                Location/Qualifiers
source                 1..11
                       mol_type = protein
                       organism = Mus musculus
SEQUENCE: 17
RASGNIHNYL A                                                      11

SEQ ID NO: 18          moltype = AA  length = 7
FEATURE                Location/Qualifiers
source                 1..7
                       mol_type = protein
                       organism = Mus musculus
SEQUENCE: 18
NAKTLAD                                                           7

SEQ ID NO: 19          moltype = AA  length = 9
FEATURE                Location/Qualifiers
source                 1..9
                       mol_type = protein
                       organism = Mus musculus
SEQUENCE: 19
QHFWSTPYT                                                         9

SEQ ID NO: 20          moltype = AA  length = 11
FEATURE                Location/Qualifiers
source                 1..11
                       mol_type = protein
                       organism = Mus musculus
SEQUENCE: 20
SASQGISNYL N                                                      11

SEQ ID NO: 21          moltype = AA  length = 7
FEATURE                Location/Qualifiers
source                 1..7
                       mol_type = protein
                       organism = Mus musculus
SEQUENCE: 21
YTSSLHS                                                           7

SEQ ID NO: 22          moltype = AA  length = 9
FEATURE                Location/Qualifiers
source                 1..9
                       mol_type = protein
                       organism = Mus musculus
SEQUENCE: 22
QQYSKLPWT                                                         9

SEQ ID NO: 23          moltype = AA  length = 16
FEATURE                Location/Qualifiers
source                 1..16
                       mol_type = protein
                       organism = Mus musculus
SEQUENCE: 23
RSSQSLVHIN GNTYLH                                                 16

SEQ ID NO: 24          moltype = AA  length = 7
FEATURE                Location/Qualifiers
source                 1..7
                       mol_type = protein
                       organism = Mus musculus
SEQUENCE: 24
KVSNRFS                                                           7

SEQ ID NO: 25          moltype = AA  length = 9
FEATURE                Location/Qualifiers
source                 1..9
                       mol_type = protein
                       organism = Mus musculus
SEQUENCE: 25
SQSTHVPWT                                                         9

SEQ ID NO: 26          moltype = AA  length = 7
FEATURE                Location/Qualifiers
source                 1..7
                       mol_type = protein
```

```
                        organism = Mus musculus
SEQUENCE: 26
DYTFTSY                                                                7

SEQ ID NO: 27           moltype = AA  length = 6
FEATURE                 Location/Qualifiers
source                  1..6
                        mol_type = protein
                        organism = Mus musculus
SEQUENCE: 27
YPRSGN                                                                 6

SEQ ID NO: 28           moltype = AA  length = 15
FEATURE                 Location/Qualifiers
source                  1..15
                        mol_type = protein
                        organism = Mus musculus
SEQUENCE: 28
GTSITTVVER LFFDY                                                       15

SEQ ID NO: 29           moltype = AA  length = 7
FEATURE                 Location/Qualifiers
source                  1..7
                        mol_type = protein
                        organism = Mus musculus
SEQUENCE: 29
GFTFSDA                                                                7

SEQ ID NO: 30           moltype = AA  length = 8
FEATURE                 Location/Qualifiers
source                  1..8
                        mol_type = protein
                        organism = Mus musculus
SEQUENCE: 30
RNKANNHA                                                               8

SEQ ID NO: 31           moltype = AA  length = 8
FEATURE                 Location/Qualifiers
source                  1..8
                        mol_type = protein
                        organism = Mus musculus
SEQUENCE: 31
GGYYPFDY                                                               8

SEQ ID NO: 32           moltype = AA  length = 11
FEATURE                 Location/Qualifiers
source                  1..11
                        mol_type = protein
                        organism = Mus musculus
SEQUENCE: 32
RASQSISDYL H                                                           11

SEQ ID NO: 33           moltype = AA  length = 7
FEATURE                 Location/Qualifiers
source                  1..7
                        mol_type = protein
                        organism = Mus musculus
SEQUENCE: 33
YSSQSIS                                                                7

SEQ ID NO: 34           moltype = AA  length = 9
FEATURE                 Location/Qualifiers
source                  1..9
                        mol_type = protein
                        organism = Mus musculus
SEQUENCE: 34
QNGHSFPYT                                                              9

SEQ ID NO: 35           moltype = AA  length = 7
FEATURE                 Location/Qualifiers
source                  1..7
                        mol_type = protein
                        organism = Mus musculus
SEQUENCE: 35
GFTFSSY                                                                7

SEQ ID NO: 36           moltype = AA  length = 6
FEATURE                 Location/Qualifiers
source                  1..6
```

```
                      mol_type = protein
                      organism = Mus musculus
SEQUENCE: 36
SSGGSH                                                     6

SEQ ID NO: 37         moltype = AA  length = 14
FEATURE               Location/Qualifiers
source                1..14
                      mol_type = protein
                      organism = Mus musculus
SEQUENCE: 37
HPSYYGSSLY CFDY                                            14

SEQ ID NO: 38         moltype = AA  length = 11
FEATURE               Location/Qualifiers
source                1..11
                      mol_type = protein
                      organism = Mus musculus
SEQUENCE: 38
RASQDISNYL N                                               11

SEQ ID NO: 39         moltype = AA  length = 7
FEATURE               Location/Qualifiers
source                1..7
                      mol_type = protein
                      organism = Mus musculus
SEQUENCE: 39
YTSRLHS                                                    7

SEQ ID NO: 40         moltype = AA  length = 9
FEATURE               Location/Qualifiers
source                1..9
                      mol_type = protein
                      organism = Mus musculus
SEQUENCE: 40
QQGSTLPWT                                                  9

SEQ ID NO: 41         moltype = AA  length = 7
FEATURE               Location/Qualifiers
source                1..7
                      mol_type = protein
                      organism = Mus musculus
SEQUENCE: 41
GYTFTTY                                                    7

SEQ ID NO: 42         moltype = AA  length = 6
FEATURE               Location/Qualifiers
source                1..6
                      mol_type = protein
                      organism = Mus musculus
SEQUENCE: 42
HPSDSD                                                     6

SEQ ID NO: 43         moltype = AA  length = 8
FEATURE               Location/Qualifiers
source                1..8
                      mol_type = protein
                      organism = Mus musculus
SEQUENCE: 43
SLYYTMDY                                                   8

SEQ ID NO: 44         moltype = AA  length = 11
FEATURE               Location/Qualifiers
source                1..11
                      mol_type = protein
                      organism = Mus musculus
SEQUENCE: 44
KASQDIKKYI A                                               11

SEQ ID NO: 45         moltype = AA  length = 7
FEATURE               Location/Qualifiers
source                1..7
                      mol_type = protein
                      organism = Mus musculus
SEQUENCE: 45
YTSTLQP                                                    7

SEQ ID NO: 46         moltype = AA  length = 9
FEATURE               Location/Qualifiers
```

```
source                1..9
                      mol_type = protein
                      organism = Mus musculus
SEQUENCE: 46
LQYDNLLYT                                                          9

SEQ ID NO: 47         moltype = AA  length = 7
FEATURE               Location/Qualifiers
source                1..7
                      mol_type = protein
                      organism = Mus musculus
SEQUENCE: 47
DYTFTSY                                                            7

SEQ ID NO: 48         moltype = AA  length = 6
FEATURE               Location/Qualifiers
source                1..6
                      mol_type = protein
                      organism = Mus musculus
SEQUENCE: 48
YPRSGN                                                             6

SEQ ID NO: 49         moltype = AA  length = 15
FEATURE               Location/Qualifiers
source                1..15
                      mol_type = protein
                      organism = Mus musculus
SEQUENCE: 49
GTSITTVVER LFFDY                                                   15

SEQ ID NO: 50         moltype = AA  length = 7
FEATURE               Location/Qualifiers
source                1..7
                      mol_type = protein
                      organism = Mus musculus
SEQUENCE: 50
GYTFTTY                                                            7

SEQ ID NO: 51         moltype = AA  length = 6
FEATURE               Location/Qualifiers
source                1..6
                      mol_type = protein
                      organism = Mus musculus
SEQUENCE: 51
YPRDGN                                                             6

SEQ ID NO: 52         moltype = AA  length = 12
FEATURE               Location/Qualifiers
source                1..12
                      mol_type = protein
                      organism = Mus musculus
SEQUENCE: 52
DYYGSTYGYF DY                                                      12

SEQ ID NO: 53         moltype = AA  length = 11
FEATURE               Location/Qualifiers
source                1..11
                      mol_type = protein
                      organism = Mus musculus
SEQUENCE: 53
RASEKIYSYL A                                                       11

SEQ ID NO: 54         moltype = AA  length = 7
FEATURE               Location/Qualifiers
source                1..7
                      mol_type = protein
                      organism = Mus musculus
SEQUENCE: 54
DANTLAQ                                                            7

SEQ ID NO: 55         moltype = AA  length = 9
FEATURE               Location/Qualifiers
source                1..9
                      mol_type = protein
                      organism = Mus musculus
SEQUENCE: 55
QHHYVTPLT                                                          9

SEQ ID NO: 56         moltype = AA  length = 11
```

```
FEATURE                Location/Qualifiers
source                 1..11
                       mol_type = protein
                       organism = Mus musculus
SEQUENCE: 56
RASQSISDYL H                                                      11

SEQ ID NO: 57          moltype = AA  length = 7
FEATURE                Location/Qualifiers
source                 1..7
                       mol_type = protein
                       organism = Mus musculus
SEQUENCE: 57
YSSQSIS                                                           7

SEQ ID NO: 58          moltype = AA  length = 9
FEATURE                Location/Qualifiers
source                 1..9
                       mol_type = protein
                       organism = Mus musculus
SEQUENCE: 58
QNGHSFPYT                                                         9

SEQ ID NO: 59          moltype = AA  length = 8
FEATURE                Location/Qualifiers
source                 1..8
                       mol_type = protein
                       organism = Mus musculus
SEQUENCE: 59
GCSITSGY                                                          8

SEQ ID NO: 60          moltype = AA  length = 5
FEATURE                Location/Qualifiers
source                 1..5
                       mol_type = protein
                       organism = Mus musculus
SEQUENCE: 60
NYDGN                                                             5

SEQ ID NO: 61          moltype = AA  length = 10
FEATURE                Location/Qualifiers
source                 1..10
                       mol_type = protein
                       organism = Mus musculus
SEQUENCE: 61
SDGYYWYFDV                                                        10

SEQ ID NO: 62          moltype = AA  length = 11
FEATURE                Location/Qualifiers
source                 1..11
                       mol_type = protein
                       organism = Mus musculus
SEQUENCE: 62
KASQDIKSYL S                                                      11

SEQ ID NO: 63          moltype = AA  length = 7
FEATURE                Location/Qualifiers
source                 1..7
                       mol_type = protein
                       organism = Mus musculus
SEQUENCE: 63
YATSLAD                                                           7

SEQ ID NO: 64          moltype = AA  length = 9
FEATURE                Location/Qualifiers
source                 1..9
                       mol_type = protein
                       organism = Mus musculus
SEQUENCE: 64
LQHAERPLT                                                         9

SEQ ID NO: 65          moltype = AA  length = 7
FEATURE                Location/Qualifiers
source                 1..7
                       mol_type = protein
                       organism = Mus musculus
SEQUENCE: 65
GYTFTSY                                                           7
```

```
SEQ ID NO: 66           moltype = AA  length = 6
FEATURE                 Location/Qualifiers
source                  1..6
                        mol_type = protein
                        organism = Mus musculus
SEQUENCE: 66
YPGSGN                                                            6

SEQ ID NO: 67           moltype = AA  length = 11
FEATURE                 Location/Qualifiers
source                  1..11
                        mol_type = protein
                        organism = Mus musculus
SEQUENCE: 67
FFILTSYYFD Y                                                      11

SEQ ID NO: 68           moltype = AA  length = 11
FEATURE                 Location/Qualifiers
source                  1..11
                        mol_type = protein
                        organism = Mus musculus
SEQUENCE: 68
KASQNVGTAV A                                                      11

SEQ ID NO: 69           moltype = AA  length = 7
FEATURE                 Location/Qualifiers
source                  1..7
                        mol_type = protein
                        organism = Mus musculus
SEQUENCE: 69
LASNRYT                                                           7

SEQ ID NO: 70           moltype = AA  length = 9
FEATURE                 Location/Qualifiers
source                  1..9
                        mol_type = protein
                        organism = Mus musculus
SEQUENCE: 70
QQYSNYPLT                                                         9

SEQ ID NO: 71           moltype = AA  length = 7
FEATURE                 Location/Qualifiers
source                  1..7
                        mol_type = protein
                        organism = Mus musculus
SEQUENCE: 71
GYTFTSY                                                           7

SEQ ID NO: 72           moltype = AA  length = 6
FEATURE                 Location/Qualifiers
source                  1..6
                        mol_type = protein
                        organism = Mus musculus
SEQUENCE: 72
NPNNGG                                                            6

SEQ ID NO: 73           moltype =   length =
SEQUENCE: 73
000

SEQ ID NO: 74           moltype = AA  length = 11
FEATURE                 Location/Qualifiers
source                  1..11
                        mol_type = protein
                        organism = Mus musculus
SEQUENCE: 74
SASQGIHNYL N                                                      11

SEQ ID NO: 75           moltype = AA  length = 7
FEATURE                 Location/Qualifiers
source                  1..7
                        mol_type = protein
                        organism = Mus musculus
SEQUENCE: 75
YTSGLHS                                                           7

SEQ ID NO: 76           moltype = AA  length = 9
FEATURE                 Location/Qualifiers
source                  1..9
```

```
                         mol_type = protein
                         organism = Mus musculus
SEQUENCE: 76
QQYSKLPWT                                                        9

SEQ ID NO: 77            moltype = AA  length = 16
FEATURE                  Location/Qualifiers
source                   1..16
                         mol_type = protein
                         organism = Mus musculus
SEQUENCE: 77
RSSQSLENSD GNTYLN                                                16

SEQ ID NO: 78            moltype = AA  length = 7
FEATURE                  Location/Qualifiers
source                   1..7
                         mol_type = protein
                         organism = Mus musculus
SEQUENCE: 78
RVSNRFS                                                          7

SEQ ID NO: 79            moltype = AA  length = 9
FEATURE                  Location/Qualifiers
source                   1..9
                         mol_type = protein
                         organism = Mus musculus
SEQUENCE: 79
LQVTHVPYT                                                        9

SEQ ID NO: 80            moltype = AA  length = 7
FEATURE                  Location/Qualifiers
source                   1..7
                         mol_type = protein
                         organism = Mus musculus
SEQUENCE: 80
GYTFTTY                                                          7

SEQ ID NO: 81            moltype = AA  length = 6
FEATURE                  Location/Qualifiers
source                   1..6
                         mol_type = protein
                         organism = Mus musculus
SEQUENCE: 81
YPRDGN                                                           6

SEQ ID NO: 82            moltype = AA  length = 12
FEATURE                  Location/Qualifiers
source                   1..12
                         mol_type = protein
                         organism = Mus musculus
SEQUENCE: 82
DYYGSTYGYF DY                                                    12

SEQ ID NO: 83            moltype = AA  length = 11
FEATURE                  Location/Qualifiers
source                   1..11
                         mol_type = protein
                         organism = Mus musculus
SEQUENCE: 83
RASEKIYSYL A                                                     11

SEQ ID NO: 84            moltype = AA  length = 7
FEATURE                  Location/Qualifiers
source                   1..7
                         mol_type = protein
                         organism = Mus musculus
SEQUENCE: 84
DANTLAQ                                                          7

SEQ ID NO: 85            moltype = AA  length = 9
FEATURE                  Location/Qualifiers
source                   1..9
                         mol_type = protein
                         organism = Mus musculus
SEQUENCE: 85
QHHYVTPLT                                                        9

SEQ ID NO: 86            moltype = AA  length = 8
FEATURE                  Location/Qualifiers
```

```
source                  1..8
                        mol_type = protein
                        organism = Mus musculus
SEQUENCE: 86
DYSITSGY                                                                 8

SEQ ID NO: 87           moltype = AA  length = 5
FEATURE                 Location/Qualifiers
source                  1..5
                        mol_type = protein
                        organism = Mus musculus
SEQUENCE: 87
SYDGS                                                                    5

SEQ ID NO: 88           moltype = AA  length = 8
FEATURE                 Location/Qualifiers
source                  1..8
                        mol_type = protein
                        organism = Mus musculus
SEQUENCE: 88
GWDYCFDY                                                                 8

SEQ ID NO: 89           moltype = AA  length = 11
FEATURE                 Location/Qualifiers
source                  1..11
                        mol_type = protein
                        organism = Mus musculus
SEQUENCE: 89
SASQGISNYL N                                                             11

SEQ ID NO: 90           moltype = AA  length = 7
FEATURE                 Location/Qualifiers
source                  1..7
                        mol_type = protein
                        organism = Mus musculus
SEQUENCE: 90
YTSGLHS                                                                  7

SEQ ID NO: 91           moltype = AA  length = 9
FEATURE                 Location/Qualifiers
source                  1..9
                        mol_type = protein
                        organism = Mus musculus
SEQUENCE: 91
QQYSQLPWT                                                                9

SEQ ID NO: 92           moltype = AA  length = 7
FEATURE                 Location/Qualifiers
source                  1..7
                        mol_type = protein
                        organism = Mus musculus
SEQUENCE: 92
GFSLTSY                                                                  7

SEQ ID NO: 93           moltype = AA  length = 5
FEATURE                 Location/Qualifiers
source                  1..5
                        mol_type = protein
                        organism = Mus musculus
SEQUENCE: 93
WGDGS                                                                    5

SEQ ID NO: 94           moltype = AA  length = 10
FEATURE                 Location/Qualifiers
source                  1..10
                        mol_type = protein
                        organism = Mus musculus
SEQUENCE: 94
YGNYYYAMDY                                                               10

SEQ ID NO: 95           moltype = AA  length = 11
FEATURE                 Location/Qualifiers
source                  1..11
                        mol_type = protein
                        organism = Mus musculus
SEQUENCE: 95
KASQDINSYL S                                                             11

SEQ ID NO: 96           moltype = AA  length = 7
```

```
FEATURE                Location/Qualifiers
source                 1..7
                       mol_type = protein
                       organism = Mus musculus
SEQUENCE: 96
RANDRLVD                                                    7

SEQ ID NO: 97          moltype = AA  length = 9
FEATURE                Location/Qualifiers
source                 1..9
                       mol_type = protein
                       organism = Mus musculus
SEQUENCE: 97
LQYDEFPYT                                                   9

SEQ ID NO: 98          moltype = AA  length = 11
FEATURE                Location/Qualifiers
source                 1..11
                       mol_type = protein
                       organism = Mus musculus
SEQUENCE: 98
RASEKIYSYL A                                                11

SEQ ID NO: 99          moltype = AA  length = 7
FEATURE                Location/Qualifiers
source                 1..7
                       mol_type = protein
                       organism = Mus musculus
SEQUENCE: 99
NAKTLAE                                                     7

SEQ ID NO: 100         moltype = AA  length = 9
FEATURE                Location/Qualifiers
source                 1..9
                       mol_type = protein
                       organism = Mus musculus
SEQUENCE: 100
QHHYVTPLT                                                   9

SEQ ID NO: 101         moltype = AA  length = 117
FEATURE                Location/Qualifiers
source                 1..117
                       mol_type = protein
                       organism = Mus musculus
SEQUENCE: 101
QVQLQQSGAE LMKPGASVKL SCKATGYTFT GYWIEWVKQR PGHGLEWIGE ILPGSGSTNY  60
NENFKGKATF TADTSSNTAY MQLSSLTTED SAIYYCSRRR SYYFDYWGQG TTLTVSS     117

SEQ ID NO: 102         moltype = AA  length = 118
FEATURE                Location/Qualifiers
source                 1..118
                       mol_type = protein
                       organism = Mus musculus
SEQUENCE: 102
QIQLVQSGPE LKKPGETVKI SCKASGYTFT TYGMSWVKQA PGKGLKWMGW INTYSGVPTY  60
TDDFKGRSVF SVETSASTAY LQINNLKYED TATYFCVRGT GFYAMDCWGQ GTSVTVSS    118

SEQ ID NO: 103         moltype = AA  length = 107
FEATURE                Location/Qualifiers
source                 1..107
                       mol_type = protein
                       organism = Mus musculus
SEQUENCE: 103
DIQMTQSPAS LSASVGETVT ITCRASGNIH NYLAWYQQKQ GKSPQLLVYN AKTLADGVPS  60
RFSGSGSGTQ YSLKINSLQP EDFGSYYCQH FWSTPYTFGG GTKLEIK               107

SEQ ID NO: 104         moltype = AA  length = 107
FEATURE                Location/Qualifiers
source                 1..107
                       mol_type = protein
                       organism = Mus musculus
SEQUENCE: 104
DIQMTQTTSS LSASLGDRVT ISCSASQGIS NYLNWYQQKP DGTVKLLIYY TSSLHSGVPS  60
RFSGSGSGTD YSLTISNLEP EDIATYYCQQ YSKLPWTFGG GTKLEIK               107

SEQ ID NO: 105         moltype = AA  length = 112
FEATURE                Location/Qualifiers
source                 1..112
                       mol_type = protein
```

```
                         organism = Mus musculus
SEQUENCE: 105
DVVMTQTPLS LPVSLGDQAS ISCRSSQSLV HINGNTYLHW YLQKPGQSPN LLIYKVSNRF  60
SGVPDRFSGS GSGTDFTLKI SRVEAEDLGV YFCSQSTHVP WTFGGGTKLE IK          112

SEQ ID NO: 106           moltype = AA  length = 124
FEATURE                  Location/Qualifiers
source                   1..124
                         mol_type = protein
                         organism = Mus musculus
SEQUENCE: 106
QVQLQQSGTE LARPGASVKL SCKASDYTFT SYGINWVKQR TGQGLEWIGE IYPRSGNTYY  60
NENFKGKATL TADKSSSTAY MELRSLTSED SAVYFCARGT SITTVVERLF FDYWGQGTTL  120
TVSS                                                               124

SEQ ID NO: 107           moltype = AA  length = 119
FEATURE                  Location/Qualifiers
source                   1..119
                         mol_type = protein
                         organism = Mus musculus
SEQUENCE: 107
EVKLEESGGG LVQPGGSMKL SCAASGFTFS DAWMDWVRQS PEKGLEWVAE IRNKANNHAT  60
YYAESVKGRF TISRDDSKSS VYLQMNSLRA EDTGIYYCTR GGYYPFDYWG QGTTLTVSS   119

SEQ ID NO: 108           moltype = AA  length = 107
FEATURE                  Location/Qualifiers
source                   1..107
                         mol_type = protein
                         organism = Mus musculus
SEQUENCE: 108
DIVMTQSPAT LSVTPGDRVS LSCRASQSIS DYLHWYQQKS HESPRLLIKY SSQSISGIPS  60
RFSGSGSGSD FTLSINSVEP EDVGVYYCQN GHSFPYTFGG GTKLEIK                107

SEQ ID NO: 109           moltype = AA  length = 123
FEATURE                  Location/Qualifiers
source                   1..123
                         mol_type = protein
                         organism = Mus musculus
SEQUENCE: 109
EVHLVESGGD LVKPGGSLKL SCAASGFTFS SYGMSWVRQT PDKRLEWVAS ISSGGSHTYY  60
PDRVKGRFTI SRDNAKNTLY LQMSSLKSED TAMYYCARHP SYYGSSLYCF DYWGQGTTLT  120
VSS                                                                123

SEQ ID NO: 110           moltype = AA  length = 107
FEATURE                  Location/Qualifiers
source                   1..107
                         mol_type = protein
                         organism = Mus musculus
SEQUENCE: 110
DIQMTQTTSS LSASLGDRVT ISCRASQDIS NYLNWYQQKP DGTVKLLIYY TSRLHSGVPS  60
RFSGSGSGTD FSLTISNLEQ EDVATYFCQQ GSTLPWTFGG GTKLEIK                107

SEQ ID NO: 111           moltype = AA  length = 117
FEATURE                  Location/Qualifiers
source                   1..117
                         mol_type = protein
                         organism = Mus musculus
SEQUENCE: 111
QVQLQQSGAE LVKPGASVKV SCKASGYTFT TYWMHWVKQR PGQGLEWIGR IHPSDSDTNY  60
NQKFKGKATL TLDKSSSTAY MQLSSLTSED SAVYYCAMSL YYTMDYWGQG TSVTVSS     117

SEQ ID NO: 112           moltype = AA  length = 107
FEATURE                  Location/Qualifiers
source                   1..107
                         mol_type = protein
                         organism = Mus musculus
SEQUENCE: 112
DIQMTQSPSS LSASLGGKVT ITCKASQDIK KYIAWYQHKP GKGPRLLIHY TSTLQPGIPS  60
RFSGSGSGRD YSFSISNLEP EDIATYYCLQ YDNLLYTFGG GTKLEIK                107

SEQ ID NO: 113           moltype = AA  length = 124
FEATURE                  Location/Qualifiers
source                   1..124
                         mol_type = protein
                         organism = Mus musculus
SEQUENCE: 113
QVQLQQSGTE LARPGASVKL SCKASDYTFT SYGINWVKKR TGQGLEWIGE IYPRSGNTYH  60
NENFKGQATL TADKSSSTAY MELRSLTSED SAVYFCARGT SITTVVERLF FDYWGQGTTL  120
TVSS                                                               124
```

```
SEQ ID NO: 114          moltype = AA  length = 121
FEATURE                 Location/Qualifiers
source                  1..121
                        mol_type = protein
                        organism = Mus musculus
SEQUENCE: 114
QVQLQQSGPE LVKPGASVKL SCKASGYTFT TYDINWVKQR PGQGLEWIGW LYPRDGNTNY  60
NEKFKGKASL TVDTSSSTAY MELHSLTSED SAVYFCARDY YGSTYGYFDY WGQGTTLTVS  120
S                                                                  121

SEQ ID NO: 115          moltype = AA  length = 107
FEATURE                 Location/Qualifiers
source                  1..107
                        mol_type = protein
                        organism = Mus musculus
SEQUENCE: 115
DIQMTQSPAS LSASVGGTVT ITCRASEKIY SYLAWYQQKQ GKSPQLLVYD ANTLAQGVPS  60
RFSGSGSGTQ FSLKINSLQP EDFGSYYCQH HYVTPLTFGA GTKLALK                107

SEQ ID NO: 116          moltype = AA  length = 107
FEATURE                 Location/Qualifiers
source                  1..107
                        mol_type = protein
                        organism = Mus musculus
SEQUENCE: 116
DIVMTQSPAT LSVTPGDRVS LSCRASQSIS DYLHWYQQKS HESPRLLIKY SSQSISGIPS  60
RFSGSGSGSD FTLSINSVEP EDVGVYYCQN GHSFPYTFGG GTKLEIK                107

SEQ ID NO: 117          moltype = AA  length = 119
FEATURE                 Location/Qualifiers
source                  1..119
                        mol_type = protein
                        organism = Mus musculus
SEQUENCE: 117
DVQLQESGPG LVKPSQSLSL TCSVTGCSIT SGYDWNWIRQ FPGNKLEWMG YINYDGNSNY  60
IPSLKNRVSI TRDTSKNQFF LKLNSVTTED TATYYCARSD GYYWYFDVWG TGTTVTVSS   119

SEQ ID NO: 118          moltype = AA  length = 107
FEATURE                 Location/Qualifiers
source                  1..107
                        mol_type = protein
                        organism = Mus musculus
SEQUENCE: 118
DIKMTQSPSS MYASLGERVT ITCKASQDIK SYLSWYQQKP WKSPKTLIYY ATSLADGVPS  60
RFSASGSGQD YSLTISSLES DDTATYYCLQ HAERPLTFGA GTKLELK                107

SEQ ID NO: 119          moltype = AA  length = 120
FEATURE                 Location/Qualifiers
source                  1..120
                        mol_type = protein
                        organism = Mus musculus
SEQUENCE: 119
QVQLQQPGAE LVKPGASVKM SCKASGYTFT SYWITWVKQG PGQGLEWIGD IYPGSGNTNY  60
NEKFKSKATL TVDTSSSTAY MQLSSLTSED SAVYYCARFF ILTSYYFDYW GQGTTLTVSS  120

SEQ ID NO: 120          moltype = AA  length = 107
FEATURE                 Location/Qualifiers
source                  1..107
                        mol_type = protein
                        organism = Mus musculus
SEQUENCE: 120
GIVMTQSQKF MSTTVGDRVS ITCKASQNVG TAVAWFQQKP GQSPKLLIYL ASNRYTGVPD  60
RFTGSGSGTD FTLTISNMQS EDLADYFCQQ YSNYPLTFGA GTKLELK                107

SEQ ID NO: 121          moltype = AA  length = 112
FEATURE                 Location/Qualifiers
source                  1..112
                        mol_type = protein
                        organism = Mus musculus
SEQUENCE: 121
QVQLQQPGTE LVKPGASVKL SCKASGYTFT SYLMHWVKQR PGQGLEWIGN INPNNGGTNY  60
NDKFKSKATL TVDKSSITAY MQLSSLTSED SAVYYCARGD YWGQGTTLTV SS          112

SEQ ID NO: 122          moltype = AA  length = 107
FEATURE                 Location/Qualifiers
source                  1..107
                        mol_type = protein
                        organism = Mus musculus
```

```
SEQUENCE: 122
DIQMTQTTSS LSASLGDRVT ISCSASQGIH NYLNWYQQKP DGTVKLLIYY TSGLHSGVPS  60
RFSGSGSGTD YSLTISNLEP EDIATYFCQQ YSKLPWTFGG GTKLEIK               107

SEQ ID NO: 123         moltype = AA  length = 112
FEATURE                Location/Qualifiers
source                 1..112
                       mol_type = protein
                       organism = Mus musculus
SEQUENCE: 123
DAVLTQTPLS LAVSLGDQAS ISCRSSQSLE NSDGNTYLNW YLQKPGQSPQ LLIYRVSNRF  60
SGGLDRFSGS GSGTDFTLKI SRVEAEDLGV YFCLQVTHVP YTFGGGTKLE IK          112

SEQ ID NO: 124         moltype = AA  length = 121
FEATURE                Location/Qualifiers
source                 1..121
                       mol_type = protein
                       organism = Mus musculus
SEQUENCE: 124
QVQLQQSGPE LVKPGASVKL SCKASGYTFT TYDINWVKQR PGQGLEWIGW LYPRDGNTNY  60
NEKFKGKASL TVDTSSSTAY MELHSLTSED SAVYFCARDY YGSTYGYFDY WGQGTTLTVS  120
S                                                                  121

SEQ ID NO: 125         moltype = AA  length = 107
FEATURE                Location/Qualifiers
source                 1..107
                       mol_type = protein
                       organism = Mus musculus
SEQUENCE: 125
DIQMTQSPAS LSASVGGTVT ITCRASEKIY SYLAWYQQKQ GKSPQLLVYD ANTLAQGVPS  60
RFSGSGSGTQ FSLKINSLQP EDFGSYYCQH HYVTPLTFGA GTKLALK               107

SEQ ID NO: 126         moltype = AA  length = 117
FEATURE                Location/Qualifiers
source                 1..117
                       mol_type = protein
                       organism = Mus musculus
SEQUENCE: 126
DVQLQESGPG LVKPSQSLSL TCSVTDYSIT SGYYWNWIRQ FPGNKLEWMG YISYDGSNNY  60
NPSLKNRLSI TRDTSKNQFF LKLNSVTPED TATYYCARGW DYCFDYWGQG ATLTVSS     117

SEQ ID NO: 127         moltype = AA  length = 107
FEATURE                Location/Qualifiers
source                 1..107
                       mol_type = protein
                       organism = Mus musculus
SEQUENCE: 127
DIQMTQTTSS LSASLGDRVT ISCSASQGIS NYLNWYQQKP DGTVKLLIYY TSGLHSGVPS  60
RFSGSGSGTD YSLTISNLEP EDIATYYCQQ YSQLPWTFGG GTKLEIK               107

SEQ ID NO: 128         moltype = AA  length = 118
FEATURE                Location/Qualifiers
source                 1..118
                       mol_type = protein
                       organism = Mus musculus
SEQUENCE: 128
QVQLKESGPG LVAPSQSLSI TCTVSGFSLT SYGVSWVRQP PGKGLEWLGV IWGDGSTNYH  60
SALISRLSIS KDNSKSQVFL KLNSLQTDDT ATYYCAEYGN YYYAMDYWGQ GTSVTVSS    118

SEQ ID NO: 129         moltype = AA  length = 107
FEATURE                Location/Qualifiers
source                 1..107
                       mol_type = protein
                       organism = Mus musculus
SEQUENCE: 129
DIKMTQSPSS MYASLGERVT ITCKASQDIN SYLSWFQQKP GKSPKTLIYR ANRLVDGVPS  60
RFSGSGSGQD YSLTISSLEY EDMGIYYCLQ YDEFPYTFGG GTKQEIK               107

SEQ ID NO: 130         moltype = AA  length = 107
FEATURE                Location/Qualifiers
source                 1..107
                       mol_type = protein
                       organism = Mus musculus
SEQUENCE: 130
DIQMTQSPAS LSASVGETVT ITCRASEKIY SYLAWYQQKQ GKSPQLLVYN AKTLAEGVPS  60
RFSGSGSGTQ FSLKINSLQP EDFGSYYCQH HYVTPLTFGA GTKLELK               107

SEQ ID NO: 131         moltype = DNA  length = 351
FEATURE                Location/Qualifiers
```

```
source                  1..351
                        mol_type = genomic DNA
                        organism = Mus musculus
SEQUENCE: 131
caggttcagc tgcagcagtc tggagctgag ctgatgaagc ctggggcctc agtgaagctt  60
tcctgcaagg ctactggcta cacattcact ggctactgga tagagtgggt aaagcagagg  120
cctggacatg gccttgagtg gattggagag attttacctg gaagtggtag tactaactac  180
aatgagaact tcaagggcaa ggccacattc actgcagata catcctccaa cacagcctac  240
atgcaactca gcagcctgac aactgaggac tctgccatct attactgttc aagaaggaga  300
tcttactact ttgactactg gggccaaggc accactctca cagtctcctc a           351

SEQ ID NO: 132          moltype = DNA  length = 354
FEATURE                 Location/Qualifiers
source                  1..354
                        mol_type = genomic DNA
                        organism = Mus musculus
SEQUENCE: 132
cagatccagt tggtacagtc tgggcctgag ctgaagaagc ctggagagac agtcaagatc  60
tcctgcaagg cttctgggta taccttcaca acctatggaa tgagctgggt gaaacaggct  120
ccaggaaagg gtttaaagtg gatgggctgg ataaacacct actctggagt gccaacatat  180
actgatgact tcaagggacg gtctgtcttc tctgtggaaa cctctgccag cactgcctat  240
ttgcagatca acaacctcaa atatgaggac acggctacat atttctgtgt aagagggact  300
gggttctatg ctatggactg ctggggtcaa ggaacctcag tcaccgtctc ctca        354

SEQ ID NO: 133          moltype = DNA  length = 321
FEATURE                 Location/Qualifiers
source                  1..321
                        mol_type = genomic DNA
                        organism = Mus musculus
SEQUENCE: 133
gacatccaga tgactcagtc tccagcctcc ctatctgcat ctgtgggaga aactgtcacc  60
atcacatgtc gagcaagtgg gaatattcac aattatttag catggtatca gcagaaacag  120
ggaaaatctc ctcagctcct ggtctataat gcaaaaacct tagcagatgg tgtgccatca  180
aggttcagtg gcagtggatc aggaacacaa tattctctca agatcaacag cctgcagcct  240
gaagattttg ggagttatta ctgtcaacat ttttggagta ctccgtacac gttcggaggg  300
gggaccaaac tggaaataaa a                                             321

SEQ ID NO: 134          moltype = DNA  length = 321
FEATURE                 Location/Qualifiers
source                  1..321
                        mol_type = genomic DNA
                        organism = Mus musculus
SEQUENCE: 134
gatatccaga tgacacagac tacatcctcc ctgtctgcct ctctgggaga cagagtcacc  60
atcagttgca gtgcaagtca gggcattagc aattatttaa actggtatca gcagaaacca  120
gatggaactg ttaaactcct gatctattac acatcaagtt tacactcagg agtcccatca  180
aggttcagtg gcagtgggtc tgggacagat tattctctca ccatcagcaa cctggaacct  240
gaagatattg ccacttacta ttgtcagcag tatagtaagc ttccgtggac gttcggtgga  300
ggcaccaagc tggaaatcaa a                                             321

SEQ ID NO: 135          moltype = DNA  length = 336
FEATURE                 Location/Qualifiers
source                  1..336
                        mol_type = genomic DNA
                        organism = Mus musculus
SEQUENCE: 135
gatgttgtga tgacccaaac tccactctcc ctgcctgtca gtcttggaga tcaagcctcc  60
atctcttgca gatctagtca gagccttgta cacattaatg gaaacaccta tttacattgg  120
tacctgcaga agccaggcca gtctccaaac ctcctgatct acaaagtttc caaccgattt  180
tctggggtcc cagacaggtt cagtggcagt ggatcaggga cagatttcac actcaagatc  240
agcagagtgg aggctgagga tctgggagtt tatttctgct ctcaaagtac acatgttccg  300
tggacgttcg gtggaggcac caagctggaa atcaaa                            336

SEQ ID NO: 136          moltype = DNA  length = 371
FEATURE                 Location/Qualifiers
source                  1..371
                        mol_type = genomic DNA
                        organism = Mus musculus
SEQUENCE: 136
caggttcagc tgcagcagtc tggaactgag ctggcgaggc ctggggcttc agtgaagctg  60
tcctgcaagg cttctgacta caccttcaca agctatggta taaactgggt gaagcagaga  120
actggacagg gccttgagtg gattggagag atttatccta gaagtggtaa tacttactac  180
aatgagaact tcaagggcaa ggccacactg actgcagaca aatcctccag cacagcgtac  240
atggagctcc gcagcctgac atctgaggac tctgcggtct atttctgtgc aagagggacg  300
tctattacta cggtagtaga gagactcttc tttgactact ggggccaagg caccactctc  360
acagtctcct c                                                        371

SEQ ID NO: 137          moltype = DNA  length = 358
FEATURE                 Location/Qualifiers
```

```
source                  1..358
                        mol_type = genomic DNA
                        organism = Mus musculus
SEQUENCE: 137
gaagtgaagc ttgaggagtc tggaggaggc ttggtgcaac ctggaggatc catgaaactc  60
tcttgtgctg cctctggatt cacttttagt gacgcctgga tggactgggt ccgccagtct  120
ccagagaagg ggcttgagtg ggttgctgaa attagaaaca aagctaataa tcatgcaaca  180
tactatgctg agtctgtgaa agggaggttc accatctcaa gagatgattc caaaagtagt  240
gtctacctgc aaatgaacag cttaagagct gaagacactg gcatttatta ctgtaccagg  300
ggtggttact accctttga ctactggggc caaggcacca ctctcacagt ctcctcac    358

SEQ ID NO: 138          moltype = DNA  length = 321
FEATURE                 Location/Qualifiers
source                  1..321
                        mol_type = genomic DNA
                        organism = Mus musculus
SEQUENCE: 138
gacattgtga tgactcagtc tccagccacc ctgtctgtga ctccaggaga tagagtctct  60
ctttcctgca gggccagcca gagtattagc gactacttac actggtatca acaaaaatca  120
catgagtctc caaggcttct catcaaatat tcttcccaat ccatctctgg gatcccctcc  180
aggttcagtg gcagtggatc agggtcagat ttcactctca gtatcaacag tgtggaacct  240
gaagatgttg gagtgtatta ctgtcaaaat ggtcacagct ttccgtacac gttcggaggg  300
gggaccaagc tggaaataaa a                                            321

SEQ ID NO: 139          moltype = DNA  length = 369
FEATURE                 Location/Qualifiers
source                  1..369
                        mol_type = genomic DNA
                        organism = Mus musculus
SEQUENCE: 139
gaggtgcacc tggtggagtc tgggggagac ttagtgaagc ctggagggtc cctgaaactc  60
tcctgtgcag cctctggatt cactttcagc agctatggca tgtcttgggt tcgccagact  120
ccagacaaga ggctggagtg ggtcgcaagt attagtagtg gtggtagtca cacttactat  180
ccagacaggg tgaaggggcg attcaccatc tccagagaca atgccaagaa caccctgtac  240
ctgcaaatga gcagtctgaa gtctgaggac acagccatgt attactgtgc aagacacccg  300
agttactacg gtagtagcct gtactgcttt gactactggg gccaaggcac cactctcaca  360
gtctcctca                                                          369

SEQ ID NO: 140          moltype = AA  length = 321
FEATURE                 Location/Qualifiers
source                  1..321
                        mol_type = protein
                        organism = Mus musculus
SEQUENCE: 140
GATATCCAGA TGACACAGAC TACATCCTCC CTGTCTGCCT CTCTGGGAGA CAGAGTCACC  60
ATCAGTTGCA GGGCAAGTCA GGACATTAGC AATTATTTAA ACTGGTATCA GCAGAAACCA  120
GATGGAACTG TTAAACTCCT GATCTACTAC ACATCAAGAT TACACTCAGG AGTCCCATCA  180
AGGTTCAGTG GCAGTGGGTC TGGAACAGAT TTTTCTCTCA CCATTAGCAA CCTGGAGCAA  240
GAAGATGTTG CCACTTACTT TTGCCAACAG GGCAGTACGC TTCCGTGGAC GTTCGGTGGA  300
GGCACCAAGC TGGAAATCAA A                                            321

SEQ ID NO: 141          moltype = DNA  length = 351
FEATURE                 Location/Qualifiers
source                  1..351
                        mol_type = genomic DNA
                        organism = Mus musculus
SEQUENCE: 141
caggtccaac tgcagcagtc tggggctgaa ctggtgaagc ctggggcttc agtgaaggtg  60
tcctgcaagg cttctggcta caccttcacc acctactgga tgcactgggt gaagcagagg  120
cctggccaag gccttgagtg gattggaagg attcatcctt ctgatagtga tactaactac  180
aatcaaaagt tcaagggcaa ggccacattg actttagaca aatcctccag cacagcctac  240
atgcagctca gcagcctgac atctgaggac tctgcggtct attactgtgc aatgagcctt  300
tactatacta tggactactg gggtcaagga acctcagtca ccgtctcctc a           351

SEQ ID NO: 142          moltype = DNA  length = 321
FEATURE                 Location/Qualifiers
source                  1..321
                        mol_type = genomic DNA
                        organism = Mus musculus
SEQUENCE: 142
gacatccaga tgacacagtc tccatcctca ctgtctgcat ctctgggagg caaagtcacc  60
atcacttgca aggcaagcca agacattaaa aagtatatag cttggtacca acacaagcct  120
ggaaaaggtc ctaggctgct catacattac acatctacat tacagccagg catcccatca  180
aggttcagtg gaagtgggtc tgggagagat tattccttca gcatcagcaa cctggagcct  240
gaagatattg caacttatta ttgtctacag tatgataatc ttctgtacac gttcggaggg  300
gggaccaagc tggaaataaa a                                            321

SEQ ID NO: 143          moltype = DNA  length = 372
FEATURE                 Location/Qualifiers
```

```
source                  1..372
                        mol_type = genomic DNA
                        organism = Mus musculus
SEQUENCE: 143
caggttcagc tgcagcagtc tggaactgag ctggcgaggc ctggggcttc agtgaagctg  60
tcctgcaagg cttctgacta caccttcaca agctatggta taaactgggt gaagaagaga  120
actggacagg gccttgagtg gattggagag atttatccta gaagtggtaa tacttaccac  180
aatgagaact tcaagggcca ggccacactg actgcagaca aatcctccag cacagcgtac  240
atggagctcc gcagcctgac atctgaggac tctgcggtct atttctgtgc aagagggacg  300
tctattacta cggtagtaga gagactcttc tttgactact ggggccaagg caccactctc  360
acagtctcct ca                                                      372

SEQ ID NO: 144          moltype = DNA  length = 363
FEATURE                 Location/Qualifiers
source                  1..363
                        mol_type = genomic DNA
                        organism = Mus musculus
SEQUENCE: 144
caggttcagc tgcagcagtc tggacctgaa ctggtgaagc ctggggcttc agtgaagttg  60
tcctgcaagg cttctggcta caccttcaca acctacgata taaactgggt gaagcagagg  120
cctggacagg gacttgagtg gattggatgg ctttatccta gagatggtaa tactaactac  180
aatgagaagt tcaagggcaa ggcctcattg actgtagaca catcctccag cacagcgtac  240
atggagctcc acagcctgac atctgaggac tctgcggtct atttctgtgc acgagattac  300
tacggtagta cctacgggta ctttgactac tggggccaag gcaccactct cacagtctcc  360
tca                                                                363

SEQ ID NO: 145          moltype = DNA  length = 321
FEATURE                 Location/Qualifiers
source                  1..321
                        mol_type = genomic DNA
                        organism = Mus musculus
SEQUENCE: 145
gacatccaga tgactcagtc tccagcctcc ctatctgcat ctgtgggagg aactgtcacc  60
atcacatgtc gagcaagtga gaagatttac agttatttag catggtatca gcagaaacag  120
ggaaaatctc ctcagctcct ggtctatgat gcaaacacct tagcacaagg tgtgccatca  180
aggttcagtg gcagtggatc aggcacacag ttttctctga agatcaacag cctgcagcct  240
gaagattttg ggagttatta ctgtcaacat cattatgtta ctccgctcac gttcggtgct  300
gggaccaagc tggcgctgaa a                                            321

SEQ ID NO: 146          moltype = DNA  length = 322
FEATURE                 Location/Qualifiers
source                  1..322
                        mol_type = genomic DNA
                        organism = Mus musculus
SEQUENCE: 146
gacattgtga tgactcagtc tccagccacc ctgtctgtga ctccaggaga tagagtctct  60
ctttcctgca gggccagcca gagtattagc gactacttac actggtatca acaaaaatca  120
catgagtctc caaggcttct catcaaatat tcttcccaat ccatctctgg gatcccctcc  180
aggttcagtg gcagtggatc agggtcagat ttcactctca gtatcaacag tgtggaacct  240
gaagatgttg gagtgtatta ctgtcaaaat ggtcacagct ttccgtacac gttcggaggg  300
gggaccaagc tggaaataaa ac                                           322

SEQ ID NO: 147          moltype = DNA  length = 356
FEATURE                 Location/Qualifiers
source                  1..356
                        mol_type = genomic DNA
                        organism = Mus musculus
SEQUENCE: 147
gatgtacagc ttcaggagtc aggacctggc ctcgtgaaac cttctcagtc tctgtctctc  60
acctgctctg tcactggctg ctccatcacc agtggttatg actggaactg gatccggcag  120
tttccaggaa acaaactgga atggatgggc tacataaact acgatggtaa cagtaactac  180
atcccatctc tcaaaaatcg agtctccatc actcgtgaca catctaagaa ccagtttttc  240
ctgaagttga attctgtgac tactgaggac acagccacat attactgtgc aagatctgat  300
ggttactact ggtacttcga tgtctggggc acagggacca cggtcaccgt ctcctc      356

SEQ ID NO: 148          moltype = DNA  length = 321
FEATURE                 Location/Qualifiers
source                  1..321
                        mol_type = genomic DNA
                        organism = Mus musculus
SEQUENCE: 148
gacatcaaga tgacccagtc tccatcctcc atgtatgcat cgctgggaga gagagtcact  60
atcacttgca aggcgagtca ggacattaaa agctatttaa gctggtacca gcagaaacca  120
tggaaatctc ctaagaccct gatctattat gcaacaagct tggcagatgg ggtcccatca  180
agattcagtg ccagtggatc tgggcaagat tattctctaa ccatcagcag cctggagtct  240
gacgatacag caacttatta ctgtctacag catgctgagc gccctctcac gttcggtgct  300
gggaccaagc tggagctgaa a                                            321

SEQ ID NO: 149          moltype = DNA  length = 360
```

```
FEATURE                Location/Qualifiers
source                 1..360
                       mol_type = genomic DNA
                       organism = Mus musculus
SEQUENCE: 149
caggtccaac tgcagcagcc tggggctgag cttgtgaagc ctggggcttc agtgaagatg  60
tcctgcaagg cttctggcta caccttcacc agctactgga taacctgggt gaagcagggg  120
cctggacaag gccttgagtg gattggagat atttatcctg gtagtggtaa tactaactac  180
aatgagaagt tcaagagcaa ggccacactg actgtagaca catcctccag cacagcctac  240
atgcagctca gcagcctgac atctgaggac tctgcggtct attactgtgc aagattcttc  300
atactgacct cgtactactt tgactactgg ggccaaggca ccactctcac agtctcctca  360

SEQ ID NO: 150         moltype = DNA  length = 321
FEATURE                Location/Qualifiers
source                 1..321
                       mol_type = genomic DNA
                       organism = Mus musculus
SEQUENCE: 150
ggcattgtga tgacccagtc tcaaaaattc atgtccacaa cagtaggaga cagggtcagc  60
atcacctgca aggccagtca gaatgtgggt actgctgtag cctggtttca acagaaacca  120
ggacaatctc ctaaactact gatttactta gcatccaatc ggtacactgg agtccctgat  180
cgcttcacag gcagtggatc tgggacagat ttcactctca ccattagcaa tatgcagtct  240
gaagacctgg cagattattt ctgtcagcaa tatagcaact atcctctcac gttcggtgct  300
gggaccaagc tggagctgaa a                                           321

SEQ ID NO: 151         moltype = DNA  length = 336
FEATURE                Location/Qualifiers
source                 1..336
                       mol_type = genomic DNA
                       organism = Mus musculus
SEQUENCE: 151
caggtccaac tgcagcagcc tgggactgaa ctggtgaagc ctggggcttc agtgaagctg  60
tcctgcaagg catctggcta caccttcacc agctacctga tgcactgggt gaagcagagg  120
cctggacaag gccttgagtg gattggaaat attaatccta acaatggtgg tactaactac  180
aatgataaat tcaaaagcaa ggccacactg actgtggaca aatcctccat cacagcctac  240
atgcagctca gcagcctgac atctgaggac tctgcggtct attattgtgc aagaggggac  300
tactggggcc aaggcaccac tctcacagtc tcctca                           336

SEQ ID NO: 152         moltype = DNA  length = 321
FEATURE                Location/Qualifiers
source                 1..321
                       mol_type = genomic DNA
                       organism = Mus musculus
SEQUENCE: 152
gatatccaga tgacacagac tacatcctcc ctgtctgcct ctctgggaga cagagtcacc  60
atcagttgca gtgcaagtca gggcattcac aattatttaa actggtatca gcagaaacca  120
gatggaactg ttaaactcct gatctattac acatcaggtt tacactcagg agtcccatca  180
aggttcagtg gcagtgggtc tgggacagat tattctctca ccatcagcaa cctggaacct  240
gaagatattg ccacttactt ttgtcagcag tatagtaagc ttccgtggac gttcggtgga  300
ggcaccaagc tggaaatcaa a                                           321

SEQ ID NO: 153         moltype = DNA  length = 336
FEATURE                Location/Qualifiers
source                 1..336
                       mol_type = genomic DNA
                       organism = Mus musculus
SEQUENCE: 153
gatgctgtgc tgacccaaac tccactctcc ctggctgtca gtcttggaga tcaagcctcc  60
atctcttgta ggtctagtca gagccttgaa aacagtgatg gaaacaccta tttgaactgg  120
tacctccaga aaccaggcca gtctccacag ctcctgatct acagggtttc gaaccgattt  180
tctgggggcc tagacaggtt cagtggtagt ggatcaggga cagatttcac actgaaaatc  240
agcagagtgg aggctgagga tttgggagtt tatttctgcc tccaagttac acatgtcccg  300
tacacgttcg gaggggggac caagctggaa ataaaa                           336

SEQ ID NO: 154         moltype = DNA  length = 363
FEATURE                Location/Qualifiers
source                 1..363
                       mol_type = genomic DNA
                       organism = Mus musculus
SEQUENCE: 154
caggttcagc tgcagcagtc tggacctgaa ctggtgaagc ctggggcttc agtgaagttg  60
tcctgcaagg cttctggcta caccttcaca acctacgata taaactgggt gaagcagagg  120
cctggacagg gacttgagtg gattggatgg ctttatccta gagatggtaa tactaactac  180
aatgagaagt tcaagggcaa ggcctcattg actgtagaca catcctccag cacagcgtac  240
atggagctcc acagcctgac atctgaggac tctgcggtct atttctgtgc acgagattac  300
tacggtagta cctacgggta ctttgactac tggggccaag gcaccactct cacagtctcc  360
tca                                                               363

SEQ ID NO: 155         moltype = DNA  length = 321
```

```
FEATURE                 Location/Qualifiers
source                  1..321
                        mol_type = genomic DNA
                        organism = Mus musculus
SEQUENCE: 155
gacatccaga tgactcagtc tccagcctcc ctatctgcat ctgtgggagg aactgtcacc  60
atcacatgtc gagcaagtga gaagatttac agttatttag catggtatca gcagaaacag  120
ggaaaatctc ctcagctcct ggtctatgat gcaaacacct tagcacaagg tgtgccatca  180
aggttcagtg gcagtggatc aggcacacag ttttctctga agatcaacag cctgcagcct  240
gaagattttg ggagttatta ctgtcaacat cattatgtta ctccgctcac gttcggtgct  300
gggaccaagc tggcgctgaa a                                            321

SEQ ID NO: 156          moltype = DNA  length = 351
FEATURE                 Location/Qualifiers
source                  1..351
                        mol_type = genomic DNA
                        organism = Mus musculus
SEQUENCE: 156
gatgtacagc ttcaggagtc aggacctggc ctcgtgaaac cttctcagtc tctgtctctc  60
acctgctctg tcactgacta ctccatcacc agtggttatt actggaactg gatccggcag  120
tttccaggaa acaaactgga atggatgggc tacataagct acgatggtag caataactac  180
aacccatctc tcaaaaatcg actctccatc actcgtgaca catctaagaa ccagtttttc  240
ctgaagttga attctgtgac tcctgaggac acagccacat attactgtgc aagaggatgg  300
gactactgct ttgactactg gggccaaggc gccactctca cagtctcctc a           351

SEQ ID NO: 157          moltype = DNA  length = 321
FEATURE                 Location/Qualifiers
source                  1..321
                        mol_type = genomic DNA
                        organism = Mus musculus
SEQUENCE: 157
gatatccaga tgacacagac tacatcctcc ctgtctgcct ctctgggaga cagagtcacc  60
atcagttgca gtgcaagtca gggcattagc aattatttaa actggtatca gcagaaacca  120
gatggaactg ttaaactcct gatctattac acatcaggtt tacactcagg agtcccatca  180
aggttcagtg gcagtgggtc tgggacagat tattctctca ccatcagcaa cctggaacct  240
gaagatattg ccacttacta ttgtcagcag tatagtcaac ttccgtggac gttcggtgga  300
ggcaccaagc tggaaatcaa a                                            321

SEQ ID NO: 158          moltype = DNA  length = 354
FEATURE                 Location/Qualifiers
source                  1..354
                        mol_type = genomic DNA
                        organism = Mus musculus
SEQUENCE: 158
caggtgcagc tgaaggagtc aggacctggc ctggtggcgc cctcacagag cctgtccatc  60
acatgcactg tctcagggtt ctcattaacc agctatggtg taagctgggt tcgccagcct  120
ccaggaaagg gtctggagtg gctgggagta atatggggtg acgggagcac aaattatcat  180
tcagctctca tatccagact gagcatcagc aaggataact ccaagagcca agttttctta  240
aaactgaaca gtctgcaaac tgatgacaca gccacgtact actgtgccga atatggtaac  300
tattactatg ctatggacta ctggggtcaa ggaacctcag tcaccgtctc ctca        354

SEQ ID NO: 159          moltype = DNA  length = 321
FEATURE                 Location/Qualifiers
source                  1..321
                        mol_type = genomic DNA
                        organism = Mus musculus
SEQUENCE: 159
gacatcaaga tgacccagtc tccatcttcc atgtatgcat ctctaggaga gagagtcact  60
atcacttgca aggcgagtca ggacattaat agctatttaa gctggttcca gcagaaacca  120
gggaaatctc ctaagaccct gatctatcgt gcaaacagat tggtagatgg ggtcccatca  180
aggttcagtg gcagtggatc tgggcaagat tattctctca ccatcagcag cctggagtat  240
gaagatatgg gaatttatta ttgtctacag tatgatgagt ttccgtacac gttcggaggg  300
gggaccaagc aggaaataaa a                                            321

SEQ ID NO: 160          moltype = DNA  length = 321
FEATURE                 Location/Qualifiers
source                  1..321
                        mol_type = genomic DNA
                        organism = Mus musculus
SEQUENCE: 160
gacatccaga tgactcagtc tccagcctcc ctatctgcat ctgtgggaga aactgtcacc  60
atcacatgtc gagcaagtga gaaaatttac agttatttag catggtatca gcagaaacag  120
ggaaaatctc ctcagctcct ggtctataat gcaaaaacct tagcagaagg tgtgccatca  180
aggttcagtg gcagtggatc aggcacacag ttttctctga agatcaacag cctgcagcct  240
gaagattttg ggagttatta ctgtcaacat cattatgtta ctccgctcac gttcggtgct  300
gggaccaagc tggagctgaa a                                            321
```

MONOCLONAL ANTIBODIES AND CONJUGATES AGAINST PROSTAGLANDIN F2 RECEPTOR INHIBITOR AND USES THEREOF

CROSS-REFERENCE TO RELATED APPLICATION

This application is a continuation of U.S. patent application Ser. No. 16/755,685 filed Apr. 13, 2020, which is a National Stage Entry of and claims priority to International Patent Application No. PCT/US2018/055905 filed Oct. 15, 2018, which claims the benefit of U.S. Provisional Application No. 62/571,961, filed Oct. 13, 2017, all of which are hereby incorporated in their entirety by reference for all purposes as if copied and pasted herein.

INCORPORATION-BY-REFERENCE OF MATERIAL SUBMITTED ELECTRONICALLY

Incorporated by reference in its entirety herein is a computer-readable nucleotide/amino acid sequence listing file named "AG015USCON1-WIPO-ST26," 152 Kilobytes in size, created on Oct. 26, 2023.

FIELD OF THE INVENTION

The present disclosure relates to antibodies and related molecules that bind to Prostaglandin F2 Receptor Inhibitor (PTGFRN). The present disclosure also relates to molecules comprising, or alternatively consisting of, full-length antibodies, antibody fragments or variants thereof. The present disclosure further relates to the amino acid and nucleic acid sequences coding for such antibodies. The present disclosure also relates to antibody conjugates (e.g., antibody-drug conjugates or immunoconjugates) comprising the anti-PTGFRN antibodies, compositions comprising the anti-PTGFRN antibodies, and methods for using the anti-PTGFRN antibodies, and their conjugates for treating conditions associated with PTGFRN expression (e.g., cancer). The disclosure further comprises the use of said antibodies, antigen-binding fragment thereof, or antibody-drug conjugates and corresponding processes, for detecting and diagnosing pathological disorders associated with expression of PTGFRN. The disclosure finally comprises products and/or compositions or kits comprising at least such antibody or antibody-drug conjugate for the prognosis or diagnostic or therapy monitoring of such disorders.

BACKGROUND

Monoclonal antibodies have become one of the most important tools in the diagnosis and treatment of a variety of diseases, including cancer. As of Jan. 11, 2017, the FDA has approved 68 therapeutic monoclonal antibodies (Cai H H (2017) Therapeutic Monoclonal Antibodies Approved by FDA in 2016. MOJ Immunol 5(1): 00145). "Monoclonal antibody products today are approved for the treatment of a variety of diseases, ranging from those that treat patient populations of a few thousand or less for such orphan indications as paroxysmal nocturnal hemoglobinuria or the cryopyrin-associated periodic syndromes to those treating hundreds of thousands of patients for some cancers and multiple sclerosis or even millions of patients for diseases such as asthma and rheumatoid arthritis." (Ecker, et al., Monoclonal Antibodies 7(1):9-14, 2015).

Monoclonal antibodies that recognize antigens expressed on the surface of cancer cells can be used to target specific tumor types. For example, a monoclonal antibody that recognizes the EpCAM/17-1A antigen located on the cell surfaces of carcinomas, edrecolomab, and a monoclonal antibody directed against the receptor tyrosine-protein kinase erbB-2 (also known as CD340 and HER2/neu), trastuzumab, is a frontline therapy for the treatment of positive breast cancer. Other monoclonal antibody therapeutics include rituximab, which binds to the CD20 antigen, and is used to treat B-cell lymphomas, alemtuzumab which binds the CD52 antigen and is used to treat chronic lymphocytic leukemia, and ipilimumab, which binds to CTLA-4 and is used to treat melanoma.

Monoclonal antibodies can also be conjugated to drug molecules to create antibody-drug conjugates (ADCs). In one example, an anticancer drug (e.g. a cell toxin or cytotoxin) is coupled to a monoclonal antibody that specifically binds to an antigen found on the surface of a cancer cell. When the antibody binds the cell surface antigen, the antibody (and the toxin) can be internalized. This has the effect of conveying the toxin predominantly to cancer cells allowing the introduction of a toxin into cells that otherwise would not receive it, thereby increasing the antibody therapeutic effect, or alternatively, allowing the use of less toxin and resulting in fewer toxin-induced side effects. An example of this type of therapeutic is trastuzumab emtansine in which the monoclonal antibody trastuzumab has been conjugated to the microtubule assembly inhibitor mertansine (also called maytansinoid DM1 and emtansine). Trastuzumab emtansine is used to treat breast cancer patients that have HER2 positive tumors and are resistant to trastuzumab.

Despite the numerous examples above, there remains a need in the art for monoclonal antibody based therapeutics. In particular, there remains a need in the art for monoclonal antibody therapeutics that bind to antigens on the surface of cancer cells, thereby providing opportunities for new therapeutic development. This need and others are met by the present disclosure.

BRIEF SUMMARY

The present disclosure provides isolated antibodies, antigen-binding fragments, and derivatives thereof that bind to prostaglandin F2 receptor inhibitor (PTGFRN), i.e., anti-PTGFRN antibodies. Such antibodies, antigen-binding fragments, and derivatives thereof may be attached to one or more functional moieties (e.g. detectable moieties, cytotoxic moieties, etc). The disclosure also includes the amino acid sequences of the variable heavy and light chain of the antibodies and their corresponding nucleic acid sequences. In one embodiment, an antibody of the disclosure may be a monoclonal antibody. A suitable example of a monoclonal antibody of the disclosure is produced by murine hybridoma 33B7 which has been deposited with the ATCC and given Patent Deposit Designation PTA-124281. 33B7 is also known by the name AG02 and the two names are used interchangeably throughout this document.

In some embodiments, the present disclosure provides an isolated antibody or an antigen binding fragment thereof that specifically binds to Prostaglandin F2 Receptor Inhibitor (PTGFRN) and is internalized.

In some embodiments, the present disclosure provides an antibody or antigen-binding fragment thereof that specifically binds to the same Prostaglandin F2 Receptor Inhibitor (PTGFRN) epitope as an antibody selected from the group consisting of: an antibody comprising the polypeptide of SEQ ID NO: 101 and the polypeptide of SEQ ID NO. 103; an antibody comprising the polypeptide of SEQ ID NO: 101 and the polypeptide of SEQ ID NO:104; an antibody comprising the polypeptide of SEQ ID NO: 101 and the polypeptide of SEQ ID NO:105; an antibody comprising the polypeptide of SEQ ID NO: 102 and the polypeptide of SEQ ID NO: 103; an antibody comprising the polypeptide of SEQ ID NO: 102 and the polypeptide of SEQ ID NO: 104; an antibody comprising the polypeptide of SEQ ID NO: 102 and the polypeptide of SEQ ID NO: 105; an antibody comprising the polypeptide of SEQ ID NO: 106 and the polypeptide of SEQ ID NO:108; an antibody comprising the polypeptide of SEQ ID NO: 107 and the polypeptide of SEQ ID NO: 108; an antibody comprising the polypeptide of SEQ ID NO: 109 and the polypeptide of SEQ ID NO: 110; an antibody comprising the polypeptide of SEQ ID NO:111 and the polypeptide of SEQ ID NO: 112; an antibody comprising the polypeptide of SEQ ID NO: 113 and the polypeptide of SEQ ID NO: 115; an antibody comprising the polypeptide of SEQ ID NO. 113 and the polypeptide of SEQ ID NO: 116; an antibody comprising the polypeptide of SEQ ID NO: 114 and the polypeptide of SEQ ID NO: 115; an antibody comprising the polypeptide of SEQ ID NO: 114 and the polypeptide of SEQ ID NO: 116; an antibody comprising the polypeptide of SEQ ID NO: 117 and the polypeptide of SEQ ID NO: 118; an antibody comprising the polypeptide of SEQ ID NO: 119 and the polypeptide of SEQ ID NO:120: an antibody comprising the polypeptide of SEQ ID NO: 121 and the polypeptide of SEQ ID NO:122; an antibody comprising the polypeptide of SEQ ID NO: 121 and the polypeptide of SEQ ID NO: 123; an antibody comprising the polypeptide of SEQ ID NO:124 and the polypeptide of SEQ ID NO: 125; an antibody comprising the polypeptide of SEQ ID NO:126 and the polypeptide of SEQ ID NO: 127; an antibody comprising the polypeptide of SEQ ID NO: 128 and the polypeptide of SEQ ID NO: 129; an antibody comprising the polypeptide of SEQ ID NO: 128 and the polypeptide of SEQ ID NO: 130; and an antibody comprising the polypeptide of SEQ ID NO:4 and the polypeptide of SEQ ID NO:2.

In some embodiments, the present disclosure provides an antibody or antigen-binding fragment thereof that specifically binds to Prostaglandin F2 Receptor Inhibitor (PTGFRN), wherein said antibody or fragment thereof competitively inhibits an antibody selected from the group consisting of: an antibody comprising the polypeptide of SEQ ID NO: 101 and the polypeptide of SEQ ID NO. 103; an antibody comprising the polypeptide of SEQ ID NO. 101 and the polypeptide of SEQ ID NO: 104; an antibody comprising the polypeptide of SEQ ID NO: 101 and the polypeptide of SEQ ID NO: 105; an antibody comprising the polypeptide of SEQ ID NO: 102 and the polypeptide of SEQ ID NO:103; an antibody comprising the polypeptide of SEQ ID NO: 102 and the polypeptide of SEQ ID NO:104; an antibody comprising the polypeptide of SEQ ID NO: 102 and the polypeptide of SEQ ID NO: 105; an antibody comprising the polypeptide of SEQ ID NO: 106 and the polypeptide of SEQ ID NO: 108; an antibody comprising the polypeptide of SEQ ID NO: 107 and the polypeptide of SEQ ID NO: 108; an antibody comprising the polypeptide of SEQ ID NO: 109 and the polypeptide of SEQ ID NO:110; an antibody comprising the polypeptide of SEQ ID NO: 111 and the polypeptide of SEQ ID NO:112; an antibody comprising the polypeptide of SEQ ID NO: 113 and the polypeptide of SEQ ID NO: 115; an antibody comprising the polypeptide of SEQ ID NO: 113 and the polypeptide of SEQ ID NO: 116; an antibody comprising the polypeptide of SEQ ID NO: 114 and the polypeptide of SEQ ID NO: 115; an antibody comprising the polypeptide of SEQ ID NO: 114 and the polypeptide of SEQ ID NO: 116, an antibody comprising the polypeptide of SEQ ID NO: 117 and the polypeptide of SEQ ID NO: 118; an antibody comprising the polypeptide of SEQ ID NO:119 and the polypeptide of SEQ ID NO: 120; an antibody comprising the polypeptide of SEQ ID NO:121 and the polypeptide of SEQ ID NO: 122; an antibody comprising the polypeptide of SEQ ID NO: 121 and the polypeptide of SEQ ID NO: 123; an antibody comprising the polypeptide of SEQ ID NO: 124 and the polypeptide of SEQ ID NO: 125; an antibody comprising the polypeptide of SEQ ID NO: 126 and the polypeptide of SEQ ID NO: 127; an antibody comprising the polypeptide of SEQ ID NO: 128 and the polypeptide of SEQ ID NO: 129; an antibody comprising the polypeptide of SEQ ID NO: 128 and the polypeptide of SEQ ID NO:130; and an antibody comprising the polypeptide of SEQ ID NO:4 and the polypeptide of SEQ ID NO:2.

In some embodiments, the present disclosure provides an antibody or antigen-binding fragment thereof that specifically binds to Prostaglandin F2 Receptor Inhibitor (PTGFRN), wherein said antibody or fragment thereof comprises a heavy chain variable region (VH) and light chain variable region (VL), wherein the VII and VL comprise complementarity determining regions CDR1, CDR2, and CDR3, and wherein VH-CDR1, VH-CDR2, and VH-CDR3 and the VL-CDR1, VL-CDR2, and VL-CDR3, respectively, comprise the polypeptide sequences selected from the group consisting of: SEQ ID NOs: 11, 12, and 13 and SEQ ID NOs: 17, 18, and 19, respectively; SEQ ID NOs: 11, 12, and 13 and SEQ ID NOs: 20, 21, and 22, respectively; SEQ ID NOs: 11, 12, and 13 and SEQ ID NOs: 23, 24, and 25, respectively; SEQ ID NOs: 14, 15, and 16 and SEQ ID NOs: 17, 18, and 19, respectively; SEQ ID NOs: 14, 15, and 16 and SEQ ID NOs: 20, 21, and 22, respectively; SEQ ID NOs: 14, 15, and 16 and SEQ ID NOs: 23, 24, and 25, respectively; SEQ ID NOs: 26, 27, and 28 and SEQ ID NOs: 32, 33, and 34, respectively; SEQ ID NOs: 29, 30, and 31 and SEQ ID NOs: 32, 33, and 34, respectively; SEQ ID NOs: 35, 36, and 37 and SEQ ID NOs: 38, 39, and 40, respectively; SEQ ID NOs: 41, 42, and 43 and SEQ ID NOs: 44, 45, and 46, respectively; SEQ ID NOs: 47, 48, and 49 and SEQ ID NOs: 53, 54, and 55, respectively; SEQ ID NOs: 47, 48, and 49 and SEQ ID NOs: 56, 57, and 58, respectively; SEQ ID NOs: 50, 51, and 52 and SEQ ID NOs: 53, 54, and 55, respectively; SEQ ID NOs: 50, 51, and 52 and SEQ ID NOs: 56, 57, and 58, respectively; SEQ ID NOs: 59, 60, and 61 and SEQ ID NOs: 62, 63, and 64, respectively; SEQ ID NOs: 65, 66, and 67 and SEQ ID NOs: 68, 69, and 70, respectively; SEQ ID NOs: 71, 72, and 73 and SEQ ID NOs: 74, 75, and 76, respectively; SEQ ID NOs: 71, 72, and 73 and SEQ ID NOs: 77, 78, and 79, respectively; SEQ ID NOs: 80, 81, and 82 and SEQ ID NOs: 83, 84, and 85, respectively; SEQ ID NOs: 86, 87, and 88 and SEQ ID NOs: 89, 90, and 91, respectively; SEQ ID NOs: 92, 93, and 94 and SEQ ID NOs: 95, 96, and 97, respectively; SEQ ID NOs: 92, 93, and 94 and SEQ ID NOs: 98, 99, and 100, respectively; SEQ ID NOs: 8, 9, and 10 and SEQ ID NOs: 5, 6, and 7, respectively; and variants of (a) to (w) comprising 1, 2, 3, or 4 conservative amino acid substitutions.

In some embodiments, the antibody or antigen-binding fragment thereof of the present disclosure comprises polypeptide sequences that are at least 90%, 95%, 99%, or 100% identical to polypeptide sequences selected from the group consisting of: SEQ ID NO: 101 and SEQ ID NO: 103; SEQ ID NO: 101 and SEQ ID NO: 104; SEQ ID NO: 101 and SEQ ID NO: 105; SEQ ID NO: 102 and SEQ ID NO: 103; SEQ ID NO: 102 and SEQ ID NO: 104; SEQ ID NO: 102 and SEQ ID NO: 105; SEQ ID NO: 106 and SEQ ID NO:108; SEQ ID NO: 107 and SEQ ID NO: 108; SEQ ID NO: 109 and SEQ ID NO:110; SEQ ID NO:111 and SEQ ID NO: 112; SEQ ID NO: 113 and SEQ ID NO:115; SEQ ID NO: 113 and SEQ ID NO:116; SEQ ID NO: 114 and SEQ ID NO: 115; SEQ ID NO: 114 and SEQ ID NO: 116; SEQ ID NO: 117 and SEQ ID NO: 118; SEQ ID NO: 119 and SEQ ID NO: 120; SEQ ID NO: 121 and SEQ ID NO: 122; SEQ ID NO: 121 and SEQ ID NO: 123; SEQ ID NO: 124 and SEQ ID NO: 125; SEQ ID NO: 126 and SEQ ID NO: 127; SEQ ID NO: 128 and SEQ ID NO: 129; SEQ ID NO: 128 and SEQ ID NO: 130; and SEQ ID NO:4 and SEQ ID NO:2.

In some embodiments, the antibody or antigen binding fragment thereof is internalized. In some embodiments, the antibody or antigen binding fragment thereof is murine, human, humanized, or chimeric. In some embodiments, the antibody or antigen binding fragment thereof is CDR-grafted, recombinant, or resurfaced. In some embodiments, the antibody or antigen binding fragment thereof further comprises human or human-derived heavy and light chain variable region frameworks. In some embodiments, the antibody or antigen binding fragment thereof comprises an IgG1 or IgG2 constant region. In some embodiments, the antibody or antigen binding fragment thereof is capable of inducing cell death. In some embodiments, the antibody or antigen binding fragment thereof binds to human PTGFRN. In some embodiments, the antibody or antigen binding fragment thereof binds to murine PTGFRN. In some embodiments, the antibody is a full length antibody. In some embodiments, it is an antigen binding fragment. In some embodiments, the antibody or antigen binding fragment thereof comprises a Fab, Fab', F(ab')2, Fd, single chain Fv or scFv, disulfide linked Fv, V-NAR domain, IgNar, intrabody, IgGΔCH2, minibody, F(ab')3, tetrabody, triabody, diabody, single-domain antibody, DVD-Ig, Fcab, mAb2, (scFv)2, or scFv-Fc.

The present disclosure further provides an antibody conjugate of the formula: Ab-L-M, wherein: (a) Ab is an antibody or antigen binding fragment thereof that specifically binds to PTGFRN; (b) L is a linker; and (c) M is a functional moiety. In some embodiments, the Ab in the antibody conjugate is an antibody or antigen binding fragment thereof of any one of claims 1-18. In some embodiments, the M in the antibody conjugate is selected from the group consisting of a cytotoxic reagent, an immunomodulating agent, an imaging agent, a therapeutic protein, a biopolymer, and an oligonucleotide. In some embodiments, the M is a cytotoxic reagent. In some embodiments, the cytotoxic reagent is selected from the group consisting of an anthracycline, an auristatin, a camptothecin, a combretastatin, a dolastatin, a duocarmycin, an enediyne, a geldanamycin, an indolino-benzodiazepine dimer, a maytansine, a puromycin, a pyrrolobenzodiazepine dimer, a taxane, a vinca alkaloid, a tubulysin, a hemiasterlin, a spliceostatin, a pladienolide, and calicheamicin. In some embodiments, the cytotoxic reagent is selected from monomethyl auristatin E, monomethyl auristatin F, maytansinoid DM1, maytansinoid DM4, calicheamicin, ozogamicin, α-amanitin, yttrium-90, and iodine-131. In some embodiments, the linker in the antibody conjugate is selected from the group consisting of a cleavable linker, a non-cleavable linker, a hydrophilic linker, and a dicarboxylic acid based linker. In some embodiments, the antibody conjugate provided in the present disclosure binds PTGFRN and is internalized.

The present disclosure further provides a pharmaceutical composition comprising a therapeutically effective amount of the antibody or antigen binding fragment thereof, or the antibody conjugate encompassed by the disclosure, and a pharmaceutically acceptable carrier.

Further provided in the present disclosure is a method for treating a disorder associated with PTGFRN function or expression in a subject comprising administering to a subject in need thereof an effective amount of the antibody or antigen binding fragment thereof, the antibody conjugate, or the pharmaceutical composition encompassed by the disclosure. In some embodiments, the disorder is a cancer. In some embodiments, the cancer is a medulloblastoma, an epidermoid carcinoma, a mesothelioma, an osteosarcoma, a spindle cell sarcomatoid carcinoma, a choriocarcinoma, a rhabdomyosarcoma, a neuroblastoma, a leiomyosarcomas, a triple negative breast carcinoma, a head and neck carcinoma, castrate resistant prostate carcinoma, squamous carcinoma, lung squamous carcinoma, Ovarian carcinoma, and pancreatic carcinoma, or any metastases thereof.

The present disclosure also provides a method for decreasing tumor growth or progression in a subject who has a PTGFRN-expressing tumor, comprising administering to the subject in need thereof an effective amount of the antibody or antigen binding fragment thereof, the antibody conjugate, or the pharmaceutical composition encompassed by the disclosure.

The present disclosure further provides a method for decreasing metastasis of PTGFRN-expressing cancer cells in a subject, comprising administering to the subject in need thereof an effective amount of the antibody or antigen binding fragment thereof, the antibody conjugate, or the pharmaceutical composition encompassed by the disclosure.

The present disclosure provides a method for inducing tumor regression in a subject who has a PTGFRN-expressing tumor, comprising administering to the subject in need thereof an effective amount of the antibody or antigen binding fragment thereof, the antibody conjugate, or the pharmaceutical composition encompassed by the disclosure.

The present disclosure also provides a method for imaging a cell, comprising (1) contacting the cell with the antibody or antigen binding fragment thereof or the antibody conjugate encompassed by the disclosure; and (2) detecting the antibody or antigen binding fragment thereof or the conjugate.

The present disclosure also provides a method for identifying the expression of PTGFRN in a tumor, comprising (1) obtaining a sample of the tumor, (2) contacting the sample with the antibody or antigen binding fragment thereof or the antibody conjugate encompassed by the disclosure; and (3) detecting the antibody or antigen binding fragment thereof or the conjugate. In some embodiments, the detecting is by immunochemistry.

The present disclosure also provides a method for preventing tumor regrowth in a subject who has, or has had, a PTGFRN-expressing tumor, comprising administering to the subject in need thereof an effective amount of the antibody or antigen binding fragment thereof, the antibody conjugate, or the pharmaceutical composition encompassed by the disclosure.

The present disclosure also provides a method for ameliorating symptoms in a subject who has, or has had, a PTGFRN-expressing tumor, comprising administering to the subject in need thereof an effective amount of the antibody or antigen binding fragment thereof, the antibody conjugate, or the pharmaceutical composition encompassed by the disclosure.

Further provides in the disclosure is a diagnostic reagent comprising the antibody or antigen binding fragment thereof of the present disclosure. In some embodiments, the antibody or antigen binding fragment thereof is labeled. In some embodiments, the label is selected from the group consisting of a radiolabel, a fluorophore, a chromophore, an imaging agent and a metal ion.

The present disclosure also provides a kit comprising the antibody or antigen binding fragment thereof, the antibody conjugate, or the pharmaceutical composition encompassed by the disclosure.

The disclosure also provides an isolated polynucleotide. In some embodiments, the polynucleotide comprises a sequence that encodes a polypeptide at least 90%, 95%, 99%, or 100% identical to a sequence selected from the group consisting of SEQ ID NOs: 2, 4, and 101-130. In some embodiments, the polynucleotide comprises a sequence that is at least 90%, 95%, 99%, or 100% identical to SEQ ID NOs: 1, 2, and 131-160. The disclosure also provides a vector comprising the polynucleotide, and/or a host cell comprising the vector thereof.

In some embodiments, the present disclosure includes use of the complementary determining region (CDR) sequences of the antibodies of the disclosure to obtain binding molecules that bind PTGFRN. Such binding molecules typically comprise one or more CDR regions, or CDR-derived regions, of an antibody of the disclosure.

In some embodiments, the disclosure provides antibody-drug conjugates (ADCs) comprising the anti-PTGFRN antibodies disclosed herein. In another aspect, the disclosure comprises the use of anti-PTGFRN antibody, antigen-binding fragments thereof, and antibody-drug conjugates and corresponding processes, for detecting and diagnosing disorders associated with expression or function of PTGFRN. In certain embodiments, the disorders are cancer disorders. Examples of cancers that can be treated with the ADCs of the disclosure include, but are not limited to, medulloblastomas, spindle cell sarcomatoid carcinomas (SCSCs), mesotheliomas, epidermoid carcinomas of the head and neck, osteosarcomas, choriocarcinomas, rhabdomyosarcomas, neuroblastomas, leiomyosarcomas, triple negative breast carcinomas, and squamous carcinomas (such as the lung, breast, or head and neck cancers, etc.).

In another aspect, the disclosure comprises products and/or compositions or kits comprising at least one such antibody, antigen binding fragment, or antibody-drug conjugate for the prognosis or diagnostic or therapy monitoring of certain cancers.

In some embodiments, the present disclosure provides pharmaceutical compositions comprising an anti-PTGFRN antibody, antigen binding fragment thereof, or antibody-drug conjugate, disclosed herein and a pharmaceutically acceptable carrier.

In some embodiments, the present disclosure provides a method for treating cancer that expresses Prostaglandin F2 Receptor Inhibitor (PTGFRN) in a subject. Such methods may comprise administering to the subject a composition comprising an anti-PTGFRN antibody, or an antigen binding fragment thereof. Typically, such anti-PTGFRN antibodies and/or fragments are conjugated to a functional moiety. The conjugates may be administered in an amount sufficient to reduce or inhibit the growth of the subject's cancer. In some embodiments, the anti-PTGFRN antibody or antigen binding fragment comprises: (a) three heavy chain complementarity determining regions (VH CDR1, VH CDR2, and VH CDR3) comprising amino acid sequences: GCSITSGYYWN (VH CDR1, SEQ ID NO:8), YISHDGNNNYSPSLKN (VH CDR2, SEQ ID NO: 9), and GFYYYGYFGY (VH CDR3, SEQ ID NO:10); and (b) three light chain complementarity determining regions (VL CDR1, VL CDR2, and VL CDR3) comprising amino acid sequences: KSSQSLLYSTNQKNYLA (VL CDR1, SEQ ID NO:5), WASTRES (VL CDR2, SEQ ID NO:6), and QQYYSYRT (VL CDR3, SEQ ID NO:7).

Any cancer that expresses PTGFRN may be treated using methods of the disclosure. Examples of cancers that may be treated include, but are not limited to, a medulloblastoma, an epidermoid tumor, mesothelioma, osteosarcoma, spindle cell sarcomatoid carcinoma, choriocarcinoma, squamous carcinoma, or any local, regional, or distant metastases thereof.

Any suitable functional moiety may be conjugated to the antibodies of the disclosure. In some embodiments, the functional moiety may comprise a radioisotope, a therapeutic agent, a cytotoxic reagent, an auristatin, a dolastatin, a taxane, a duocarmycin, a calicheamicin, a cryptophycin, a DNA alkylating agent, or a tumor-activated prodrug. Suitable cytotoxic reagents include, but are not limited to, monomethyl auristatin E, monomethyl auristatin F, maytansinoid DM1, maytansinoid DM4, calicheamicin, ozogamicin, α-amanitin, yttrium-90, and iodine-131.

Antibodies or antigen binding fragments thereof suitable for use in methods of the disclosure include, but are not limited to, human antibodies or antigen binding fragments thereof, humanized antibodies or antigen binding fragments thereof, CDR-grafted antibodies or antigen binding fragments thereof, and chimeric antibodies or antigen binding fragments thereof. In some embodiments, the anti-PTGFRN antibody may comprise human or human-derived heavy and light chain variable region frameworks. In some embodiments, antibodies of the disclosure may comprise a heavy chain variable region that comprises one or more of the amino acid sequences of amino acids 47-57 of SEQ ID NO: 4, amino acids 72-87 of SEQ ID NO: 4, or amino acids 120-129 of SEQ ID NO: 4 and the light chain variable region comprises one or more of the amino acid sequences of amino acids 42-58 of SEQ ID NO: 2, amino acids 74-80 of SEQ ID NO: 2, or amino acids 113-120 of SEQ ID NO: 2.

In some embodiments, the disclosure provides an isolated antibody, or an antigen binding fragment thereof, that binds to PTGFRN. Such antibodies or fragments may comprise (a) three heavy chain complementarity determining regions (VH CDR1, VH CDR2, and VH CDR3) comprising amino acid sequences: GCSITSGYYWN (VH CDR1, SEQ ID NO:8), YISHDGNNNYSPSLKN (VH CDR2, SEQ ID NO:9), and GFYYYGYFGY (VH CDR3, SEQ ID NO: 10); and (b) three light chain complementarity determining regions (VL CDR1, VL CDR2, and VL CDR3) comprising amino acid sequences: KSSQSLLYSTNQKNYLA (VL CDR1, SEQ ID NO: 5), WASTRES (VL CDR2. SEQ ID NO:6), and QQYYSYRT (VL CDR3, SEQ ID NO:7).

In some embodiments, the isolated antibody, or an antigen binding fragment thereof, binds to PTGFRN and is internalized. An isolated antibody or fragment thereof of the disclosure may comprise a heavy chain variable region that comprises one or more of the amino acid sequences of amino acids 47-57 of SEQ ID NO: 4, amino acids 72-87 of SEQ ID NO: 4, or amino acids 120-129 of SEQ ID NO: 4 and the light chain variable region comprises one or more of the amino acid sequences of amino acids 42-58 of SEQ ID NO: 2, amino acids 74-80 of SEQ ID NO: 2, or amino acids 113-120 of SEQ ID NO: 2. An isolated antibody or antigen fragment thereof of the disclosure may comprises a heavy chain variable region having an amino acid sequence that has at least one region of contiguous amino acids that is at least 95% identical to one of amino acids 47-57 of SEQ ID NO: 4, amino acids 72-87 of SEQ ID NO: 4, or amino acids 120-129 of SEQ ID NO: 4; and a light chain variable region having an amino acid sequence that has at least one region of contiguous amino acids that is at least 95% identical to one of amino acids 42-58 of SEQ ID NO: 2, amino acids 74-80 of SEQ ID NO: 2, or amino acids 113-120 of SEQ ID NO: 2. An antibody or antigen binding fragment may be a humanized, chimeric, CDR grafted, or recombinant human antibody.

In some embodiments, the present disclosure provides an antibody conjugate of the formula: Ab-L-M, wherein: (a) Ab is an antibody or antigen-binding fragment thereof of the disclosure that binds to PTGFRN; (b) L is a linker; and (c) M is a functional moiety. An antibody or fragment thereof of the disclosure that may be used to make an antibody conjugate of the disclosure may comprise (a) three heavy chain complementarity determining regions (VH CDR1, VH CDR2, and VH CDR3) comprising amino acid sequences: GCSITSGYYWN (VH CDR1, SEQ ID NO:8), YISHDGNNNYSPSLKN (VH CDR2, SEQ ID NO:9), and GFYYYGYFGY (VH CDR3, SEQ ID NO:10); and (b) three light chain complementarity determining regions (VI. CDR1, VL CDR2, and VI. CDR3) comprising amino acid sequences: KSSQSLLYSTNQKNYLA (VL CDR1, SEQ ID NO:5), WASTRES (VL CDR2, SEQ ID NO:6), and QQYYSYRT (VL CDR3, SEQ ID NO:7).

In some embodiments, the antibody conjugate of the disclosure binds to PTGFRN and is internalized. The antibody portion of an antibody conjugate of the disclosure may comprise a heavy chain variable region that comprises one or more of the amino acid sequences of amino acids 47-57 of SEQ ID NO: 4, amino acids 72-87 of SEQ ID NO: 4, or amino acids 120-129 of SEQ ID NO: 4, and a light chain variable region that comprises one or more of the amino acid sequences of amino acids 42-58 of SEQ ID NO: 2, amino acids 74-80 of SEQ ID NO. 2, or amino acids 113-120 of SEQ ID NO: 2. An antibody or antigen fragment thereof suitable for forming an antibody conjugate of the disclosure may comprises a heavy chain variable region having an amino acid sequence that has at least one region of contiguous amino acids that is at least 95% identical to one of amino acids 47-57 of SEQ ID NO: 4, amino acids 72-87 of SEQ ID NO: 4, or amino acids 120-129 of SEQ ID NO: 4; and a light chain variable region having an amino acid sequence that has at least one region of contiguous amino acids that is at least 95% identical to one of amino acids 42-58 of SEQ ID NO: 2, amino acids 74-80 of SEQ ID NO: 2, or amino acids 113-120 of SEQ ID NO: 2. An antibody or antigen binding fragment suitable for forming an antibody conjugate of the disclosure may be a humanized, chimeric, CDR grafted, or recombinant human antibody.

In some embodiments, an antibody conjugate of the disclosure may comprise a functional moiety M that may be a cytotoxic reagent, an immunomodulating agent, an imaging agent, a therapeutic protein, a biopolymer, or an oligonucleotide. In some embodiments, M is a cytotoxic reagent. In some embodiments, M may be an anthracycline, an auristatin, a camptothecin, a combretastatin, a dolastatin, a duocarmycin, an enediyne, a geldanamycin, an indolinobenzodiazepine dimer, a maytansine, a puromycin, a pyrrolobenzodiazepine dimer, a taxane, a vinca alkaloid, a tubulysin, a hemiasterlin, a spliceostatin, a pladienolide, or a calicheamicin. In some embodiments, M may be monomethyl auristatin E, monomethyl auristatin F, maytansinoid DM1, maytansinoid DM4, calicheamicin, ozogamicin, α-amanitin, yttrium-90, or iodine-131.

In some embodiments, the disclosure provides a pharmaceutical composition comprising a therapeutically effective amount of an antibody or antigen binding fragment thereof of the disclosure or an antibody conjugate of the disclosure and a pharmaceutically acceptable carrier.

In some embodiments, the disclosure provides a method for treating a disorder associated with PTGFRN function or expression in a subject comprising administering to a subject in need thereof an effective amount of a pharmaceutical composition of the disclosure. Disorders that may be treated include cancer. Cancers that may be treated include, but are not limited to, medulloblastomas, epidermoid tumors, mesotheliomas, osteosarcomas, spindle cell sarcomatoid carcinomas, choriocarcinomas, or any metastases thereof.

In some embodiments, the disclosure provides a method for decreasing tumor growth or progression in a subject who has a PTGFRN-expressing tumor, comprising administering to the subject in need thereof an effective amount of a pharmaceutical composition of the disclosure.

In some embodiments, the disclosure provides a method for decreasing metastasis of PTGFRN-expressing cancer cells in a subject, comprising administering to the subject in need thereof an effective amount of a pharmaceutical composition of the disclosure.

In some embodiments, the disclosure provides a method for inducing tumor regression in a subject who has a PTGFRN-expressing tumor, comprising administering to the subject in need thereof an effective amount of a pharmaceutical composition of the disclosure.

In some embodiments, the disclosure provides a method for preventing tumor regrowth in a subject who has had a PTGFRN-expressing tumor, comprising administering to the subject in need thereof an effective amount of a pharmaceutical composition of the disclosure.

In some embodiments, the present disclosure provides a method for ameliorating symptoms in a subject who has, or has had, a PTGFRN-expressing tumor, comprising administering to the subject in need thereof an effective amount of a pharmaceutical composition of the disclosure.

In some embodiments, the disclosure provides a method for imaging a cell, comprising contacting the cell with an antibody or antigen binding fragment thereof of the disclosure or an antibody conjugate of the disclosure; and detecting the antibody or antigen binding fragment thereof or the antibody conjugate.

BRIEF DESCRIPTION OF THE DRAWINGS

FIG. 1A shows that rhodamine-labelled 33B7 does not bind with PTGFRN negative cells. FIG. 1B shows that 33B7 binds to same cells transfected with PTGFRN.

FIG. 3A FITC (fluorescein isothiocyanate)-labelled 33B7 bound to PTGFRN on cancer cells at 4° when there is no internalization. FIG. 3B shows 33B7 internalized in same cells when the cells are incubated at 37° C. for one hour.

(FIG. 11A) and the internalization in the same cells at 37° C. (FIG. 11B).

FIG. 12A shows the binding of 7C8 to DAOY cells at various concentrations. FIG. 12B shows the binding of 4F4 and 7B4 to MDA231, FaDu, and NCI-520 cell lines. FIG. 12C shows the binding of multiple anti-PTGFRN mAbs to DAOY cell line at 1 μg. FIG. 12D shows the binding of multiple anti-PTGFRN mAbs to A431 cells. 9G8 is an anti-PTGFRN negative control mAb that only works on EIA with anti-PTGFRN ECD. mIgG is used as the negative control.

FIG. 13A compares the efficacy of 4F4 and 5H12 to 33B7 in HEK cells overexpressing PTGFRN. mIgG and 9G8 are negative controls. FIGS. 13B and 13C show the efficacy of the cells in DAOY and A431 cell lines.

FIG. 14A shows a dose-response of 4F4 on DAOY cells. The bar on the left of each pair is mIgG (the negative control) and the bar on the right of each pair is 4F4. FIG. 14B compares the cell-killing efficacy of multiple anti-PTGFRN mAbs on DAOY cells at contraction of 0.3 nM. The upper line indicates 50% viability. The lower line shows the 4F4 efficacy level. Dose response of antibody 4F4 on A431 and MSTO cell lines are shown in FIG. 14C and FIG. 14D, respectively. The bar on the left of each pair in light gray is mIgG (the negative control) and the bar on the right of each pair in dark gray is 4F4. FIG. 14E compares the cell-killing efficacy of multiple anti-PTGFRN mAbs on A431 cell line at 0.03 nM and 0.3 nM.

FIG. 18 shows the pairing analysis of 15 mAbs with PTGFRN-ECD (Binning Matrix) based on Octet® Data. The diagonal line in dark gray indicates the self-pairing or blocking effect, and is used as the threshold to determine the strong pairs.

DETAILED DESCRIPTION

Figure 1A:
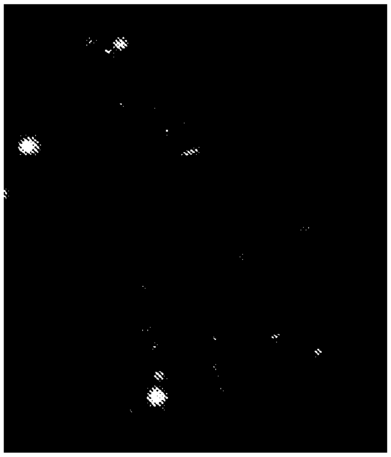
FIGS. 1A and 1B are photomicrographs showing PTGFRN positive cells display 33B7 (also called AG02) binding while PTGFRN negative cells do not bind 33B7.

The present disclosure provides antibodies and antibody conjugates (e.g., antibody-drug conjugates) that bind to PTGFRN (e.g., human PTGFRN). One example of such antibodies is 33B7. The disclosure also provides polynucleotides encoding the 33B7 antibody, compositions comprising antibodies of the disclosure, and methods of making and using these antibodies. In some embodiments, antibodies of the disclosure comprise all or a portion of the variable regions of the particular heavy and light chain sequences disclosed herein. In some embodiments, antibodies of the disclosure comprise the amino acid sequence of one or more of the CDR regions disclosed herein.

The present disclosure further comprises methods for using antibodies of the disclosure, for example, to detect PTGFRN, to modulate PTGFRN activity and/or for targeting to PTGFRN expressing cells for killing (e.g., ADCs).

I. Definitions

To facilitate an understanding of the present disclosure, a number of terms and phrases are defined below.

Prostaglandin F2 receptor inhibitor (PTGFRN) is known by several names in the art, for example, FPRP; CD315; EWI-F: CD9P-1; SMAP-6, KIAA1436, Prostaglandin F2-Alpha Receptor Regulatory Protein, Prostaglandin F2-Alpha Receptor-Associated Protein, Prostaglandin F2 Receptor Negative Regulator, Glu-Trp-Ile EWI Motif-Containing Protein F. PTGFRN has the following accession numbers: UniProt Q9P2B2, Entrez Gene ID: 5738, Ensemble: ENSG00000134247, OMIM: 601204, and HGNC: 9601.

The term “antibody” as used herein refers to an immunoglobulin molecule capable of recognizing and binding to a specific target or antigen. Antibodies of the disclosure typically comprise at least one antigen recognition site, located in the variable region of the immunoglobulin molecule. Antibodies of the disclosure may be monoclonal antibodies, polyclonal antibodies, and antigen binding fragments thereof that retain the ability to specifically bind to PTGFRN. In some embodiments, antibodies of the disclosure may be single chain (ScFv) and single domain antibodies (e.g., shark and camelid antibodies). Antibodies of the disclosure may be humanized antibodies, chimeric antibodies, or fully human antibodies. Antibodies of the disclosure may be from any source known to those skilled in the art, for example, antibodies of the disclosure may be of murine, rat, camel, human, or any other origin or may be synthesized.

As used herein, the term "antibody" encompasses intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc. For example, in some embodiments, antibodies of the disclosure may be humanized antibodies conjugated to drug molecules.

In some embodiments, antibodies of the disclosure may be humanized. The term "humanized antibody" refers to forms of non-human (e.g. murine) antibodies that are specific immunoglobulin chains, chimeric immunoglobulins, or fragments thereof that contain minimal non-human (e.g., murine) sequences. Typically, humanized antibodies are human immunoglobulins in which residues from the complementary determining region (CDR) are replaced by residues from the CDR of a non-human species (e.g. mouse, rat, rabbit, hamster) that have the desired specificity, affinity, and capability (Jones et al., 1986, Nature, 321:522-525; Riechmann et al., 1988, Nature, 332:323-327; Verhocyen et al., 1988, Science, 239:1534-1536). In some instances, the Fv framework region (FR) residues of a human immunoglobulin are replaced with the corresponding residues in an antibody from a non-human species that has the desired specificity, affinity, and capability. The humanized antibody can be further modified by the substitution of additional residues either in the Fv framework region and/or within the replaced non-human residues to refine and optimize antibody specificity, affinity, and/or capability. In general, the humanized antibody will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody can also comprise at least a portion of an immunoglobulin constant region or domain (Fc), typically that of a human immunoglobulin. Humanization may be by any method known in the art, for example, using the methods disclosed in Jones et al. Nature 321:522-525 (1986); Riechmann et al. Nature 332:323-327 (1988); Verhoeyen et al. Science 239:1534-1536 (1988). As used herein, an antibody is humanized by replacing all or a portion of one or more of the CDRs of a human antibody with all or a portion of one or more of the CDRs of a non-human antibody of the disclosure. U.S. Pat. Nos. 5,225,539; 5,585,089; 5,693,761; 5,693,762; 5,859,205 are herein incorporated by reference for their disclosures relating to humanization of antibodies.

In some embodiments of the disclosure, antibodies of the disclosure may be made in cells of animals other than mice, for example, antibodies of the disclosure may be made in cells from chickens, pigs, guinea pigs, hamsters, horses, rats, camels, goats, rabbits, and sheep. Antibodies of the disclosure may be synthetic antibodies.

The term "anti-PTGFRN antibody" or "an antibody that binds to PTGFRN" refers to an antibody that is capable of binding PTGFRN with sufficient affinity such that the antibody is useful as a diagnostic and/or therapeutic agent in targeting PTGFRN. The extent of binding of an anti-PTGFRN antibody to an unrelated, non-PTGFRN protein can be less than about 10% of the binding of the antibody to PTGFRN as measured, e.g., by an immunoassay. In certain embodiments, an antibody that binds to PTGFRN has a dissociation constant (Kd) of $<1$ μM, $<100$ nM, $<10$ nM, $<1$ nM, or $<0.1$ nM.

The term "antibody fragment" refers to a portion of an intact antibody and refers to the antigenic determining variable regions of an intact antibody. Examples of antibody fragments include, but are not limited to Fab, Fab', F(ab')2, and Fv fragments, linear antibodies, single chain antibodies, and multispecific antibodies formed from antibody fragments.

A "monoclonal antibody" refers to a homogeneous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of manners including but not limited to by hybridoma, phage selection, recombinant expression, and transgenic animals.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al (1997) J. Molec. Biol. 273:927-948)). In addition, combinations of these two approaches are sometimes used in the art to determine CDRs.

The term "human antibody" means an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

The term "humanized antibody" refers to forms of non-human (e.g. murine) antibodies that are specific immunoglobulin chains, chimeric immunoglobulins, or fragments thereof that contain minimal non-human (e.g., murine) sequences. Typically, humanized antibodies are human immunoglobulins in which residues from the complementary determining region (CDR) are replaced by residues from the CDR of a non-human species (e.g. mouse, rat, rabbit, hamster) that have the desired specificity, affinity, and capability. In some instances, the Fv framework region (FR) residues of a human immunoglobulin are replaced with the corresponding residues in an antibody from a non-human species that has the desired specificity, affinity, and capability. The humanized antibody can be further modified by the substitution of additional residues either in the Fv framework region and/or within the replaced non-human residues to refine and optimize antibody specificity, affinity, and/or capability. In general, the humanized antibody will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody can also comprise at least a portion of an immunoglobulin constant region or domain (Fc), typically that of a human immunoglobulin. Examples of methods used to generate humanized antibodies are described in U.S. Pat. No. 5,225,539.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g. mouse, rat, rabbit, etc) with the desired specificity, affinity, and capability while the constant regions are homologous to the sequences in antibodies derived from another (usually human) to avoid eliciting an immune response in that species.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present disclosure. Specific illustrative embodiments are described in the following, for instance, Example 20.

"Or better" when used herein to refer to binding affinity refers to a stronger binding between a molecule and its binding partner. "Or better" when used herein refers to a stronger binding, represented by a smaller numerical Kd value. For example, an antibody which has an affinity for an antigen of "0.3 nM or better", the antibody's affinity for the antigen is <0.3 nM, i.e. 0.29 nM, 0.28 nM, 0.27 nM etc. or any value less than 0.3 nM.

By "specifically binds," it is generally meant that an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

By "preferentially binds," it is meant that the antibody specifically binds to an epitope more readily than it would bind to a related, similar, homologous, or analogous epitope. Thus, an antibody which "preferentially binds" to a given epitope would more likely bind to that epitope than to a related epitope, even though such an antibody may cross-react with the related epitope.

An antibody is said to "competitively inhibit" binding of a reference antibody to a given epitope if it preferentially binds to that epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

The phrase "substantially similar," or "substantially the same", as used herein, denotes a sufficiently high degree of similarity between two numeric values (generally one associated with an antibody of the disclosure and the other associated with a reference/comparator antibody) such that one of skill in the art would consider the difference between the two values to be of little or no biological and/or statistical significance within the context of the biological characteristic measured by said values (e.g., Kd values). The difference between said two values can be less than about 50%, less than about 40%, less than about 30%, less than about 20%, or less than about 10% as a function of the value for the reference/comparator antibody.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cell or compositions include those which have been purified to a degree that they are no longer in a form in which they are found in nature. In some embodiments, an antibody, polynucleotide, vector, cell, or composition which is isolated is substantially pure.

As used herein, "substantially pure" refers to material which is at least 50% pure (i.e., free from contaminants), at least 90% pure, at least 95% pure, at least 98% pure, or at least 99% pure.

In some embodiments, antibodies of the disclosure may be conjugated to a functional moiety to form an antibody conjugate. The term "immunoconjugate." "conjugate." or "antibody drug conjugate" as used herein interchangeably refers to a compound or a derivative thereof that is linked to a cell-binding agent (i.e., an anti-PTGFRN antibody or fragment thereof). Antibody conjugates of the disclosure may have the formula Ab-L-M, wherein: (a) Ab is an antibody, or antigen-binding fragment thereof, of the disclosure that binds to PTGFRN; (b) L is a linker; and (c) Mis a functional moiety. Conjugation may be direct in which case Lis simply a chemical bond between Ab and M. Conjugation may involve the use of a linker. Examples of functional moieties include, but are not limited to, drugs, fluorescent molecules, radioactive molecules, chemiluminescent molecules, molecules used for imaging, epitopes, ligands and the like. Functional moieties may be conjugated to antibodies of the disclosure using any technology known to those skilled in the art. When a linker is used, the linker may be cleavable or non-cleavable and may be of any length. When a linker is used in the practice of the disclosure, the linker may be conjugated to any part of the immunoglobulin molecule or any amino-acid of the immunoglobulin molecule. A linker may be attached to an antibody of the disclosure using any technique known to those skilled in the art, for example, through surface lysines, reductive-coupling to oxidized carbohydrates, cysteine residues liberated by reducing interchain disulfide linkages, reactive cysteine residues engineered at specific sites, and acyl donor glutamine-containing tag or an endogenous glutamine made reactive by polypeptide engineering in the presence of transglutaminase and an amine. A variety of ADC linkage systems are known in the art, including hydrazone-, disulfide- and peptide-based linkages.

A "linker" is any chemical moiety that is capable of linking a compound, usually a drug, such as a maytansinoid, to a cell-binding agent such as an anti PTGFRN antibody or a fragment thereof in a stable, covalent manner. Linkers can be susceptible to or be substantially resistant to acid-induced cleavage, light-induced cleavage, peptidase-induced cleavage, esterase-induced cleavage, and disulfide bond cleavage, at conditions under which the compound or the antibody remains active. Suitable linkers are well known in the art and include, for example, disulfide groups, thioether groups, acid labile groups, photolabile groups, peptidase labile groups and esterase labile groups. Linkers also include charged linkers, and hydrophilic forms thereof as described herein and know in the art. The linker can be, for example, a cleavable linker, a non-cleavable linker, a hydrophilic linker, or a dicarboxylic acid based linker.

The terms "cancer" and "cancerous" refer to or describe the physiological condition in mammals in which a population of cells are characterized by unregulated cell growth. Examples of cancer include, but are not limited to, carcinoma, lymphoma, blastoma, sarcoma, and leukemia. "Tumor" and "neoplasm" refer to one or more cells that result from excessive cell growth or proliferation, either benign (noncancerous) or malignant (cancerous) including pre-cancerous lesions. Examples of cancer include, but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer. In certain embodiments, the cancer is a medulloblastoma, an epidermoid carcinoma, a mesothelioma, an osteosarcoma, a spindle cell sarcomatoid carcinoma, a choriocarcinoma, a rhabdomyosarcoma, a neuroblastoma, a leiomyosarcomas, a triple negative breast carcinoma, or any metastases thereof.

The terms "cancer cell," "tumor cell," and grammatical equivalents refer to the total population of cells derived from a tumor or a pre-cancerous lesion, including both non-tumorigenic cells, which comprise the bulk of the tumor cell population, and tumorigenic stem cells (cancer stem cells). As used herein, the term "tumor cell" will be modified by the term "non-tumorigenic" when referring solely to those tumor cells lacking the capacity to renew and differentiate to distinguish those tumor cells from cancer stem cells.

The term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

Administration "in combination with" one or more further therapeutic agents includes simultaneous (concurrent) and consecutive administration in any order.

The term "pharmaceutical formulation" refers to a preparation which is in such form as to permit the biological activity of the active ingredient to be effective, and which contains no additional components which are unacceptably toxic to a subject to which the formulation would be administered. The formulation can be sterile.

An "effective amount" of an antibody as disclosed herein is an amount sufficient to carry out a specifically stated purpose. An "effective amount" can be determined empirically and in a routine manner, in relation to the stated purpose.

The term "therapeutically effective amount" refers to an amount of an antibody or other drug effective to "treat" a disease or disorder in a subject or mammal. In the case of cancer, the therapeutically effective amount of the drug can reduce the number of cancer cells; reduce the tumor size; inhibit (i.e., slow to some extent or stop) cancer cell infiltration into peripheral organs; inhibit (i.e., slow to some extent or stop) tumor metastasis; inhibit, to some extent, tumor growth; and/or relieve to some extent one or more of the symptoms associated with the cancer. See the definition herein of "treating". To the extent the drug can prevent growth and/or kill existing cancer cells, it can be cytostatic and/or cytotoxic. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The word "label" when used herein refers to a detectable compound or composition which is conjugated directly or indirectly to the antibody so as to generate a "labeled" antibody. The label can be detectable by itself (e.g. radioisotope labels or fluorescent labels) or, in the case of an enzymatic label, can catalyze chemical alteration of a substrate compound or composition which is detectable.

A "chemotherapeutic agent" is a chemical compound useful in the treatment of cancer, regardless of mechanism of action. Chemotherapeutic agents include, for example, antagonists of CD20 such as Rituximab and cyclophosphamide, doxorubicin, vincristine, prednisone, fludarabine, etoposide, methotrexate, lenalidomide, chlorambucil, bendamustine and/or modified versions of such chemotherapeutics.

Terms such as "treating" or "treatment" or "to treat" or "alleviating" or "to alleviate" refer to both 1) therapeutic measures that cure, slow down, lessen symptoms of, and/or halt progression of a diagnosed pathologic condition or disorder and 2) prophylactic or preventative measures that prevent and/or slow the development of a targeted pathologic condition or disorder. Thus, those in need of treatment include those already with the disorder; those prone to have the disorder; and those in whom the disorder is to be prevented. In certain embodiments, a subject is successfully "treated" for cancer according to the methods of the present disclosure if the patient shows one or more of the following: a reduction in the number of or complete absence of cancer cells; a reduction in the tumor size; inhibition of or an absence of cancer cell infiltration into peripheral organs including, for example, the spread of cancer into soft tissue and bone; inhibition of or an absence of tumor metastasis; inhibition or an absence of tumor growth; relief of one or more symptoms associated with the specific cancer; reduced morbidity and mortality; improvement in quality of life; reduction in tumorigenicity, tumorgenic frequency, or tumorgenic capacity, of a tumor; reduction in the number or frequency of cancer stem cells in a tumor; differentiation of tumorigenic cells to a non-tumorigenic state; or some combination of effects.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide can comprise modified nucleotides, such as methylated nucleotides and their analogs. If present, modification to the nucleotide structure can be imparted before or after assembly of the polymer. The sequence of nucleotides can be interrupted by non-nucleotide components. A polynucleotide can be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars can be replaced, for example, by phosphonate groups, phosphate groups, protected by standard protecting groups, or activated to prepare additional linkages to additional nucleotides, or can be conjugated to solid supports. The 5' and 3' terminal OH can be phosphorylated or substituted with amines or organic capping group moieties of from 1 to 20 carbon atoms. Other hydroxyls can also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha.-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages can be replaced by alternative linking groups. These alternative linking groups include, but are not limited to, embodiments wherein phosphate is replaced by P(O)S ("thioate"), P(S)S ("dithioate"), "(O)NR2 ("amidate"), P(O)R, P(O)OR, CO or CH2 ("formacetal"), in which each R or R is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

The term "vector" means a construct, which is capable of delivering, and optionally expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this disclosure are based upon antibodies, in certain embodiments, the polypeptides can occur as single chains or associated chains.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. One such non-limiting example of a sequence alignment algorithm is the algorithm described in Karlin et al, 1990, Proc. Natl. Acad. Sci., 87:2264-2268, as modified in Karlin et al., 1993, Proc. Natl. Acad. Sci., 90:5873-5877, and incorporated into the NBLAST and XBLAST programs (Altschul et al., 1991, Nucleic Acids Res., 25:3389-3402). In certain embodiments, Gapped BLAST can be used as described in Altschul et al., 1997, Nucleic Acids Res. 25:3389-3402. BLAST-2, WU-BLAST-2 (Altschul et al., 1996, Methods in Enzymology, 266:460-480), ALIGN, ALIGN-2 (Genentech, South San Francisco, California) or Megalign (DNASTAR) are additional publicly available software programs that can be used to align sequences. In certain embodiments, the percent identity between two nucleotide sequences is determined using the GAP program in GCG software (e.g., using a NWSgapdna. CMP matrix and a gap weight of 40, 50, 60, 70, or 90 and a length weight of 1, 2, 3, 4, 5, or 6) In certain alternative embodiments, the GAP program in the GCG software package, which incorporates the algorithm of Needleman and Wunsch (J. Mol. Biol. (48):444-453 (1970)) can be used to determine the percent identity between two amino acid sequences (e.g., using either a Blossum 62 matrix or a PAM250 matrix, and a gap weight of 16, 14, 12, 10, 8, 6, or 4 and a length weight of 1, 2, 3, 4, 5). Alternatively, in certain embodiments, the percent identity between nucleotide or amino acid sequences is determined using the algorithm of Myers and Miller (CABIOS, 4: 11-17 (1989)). For example, the percent identity can be determined using the ALIGN program (version 2.0) and using a PAM120 with residue table, a gap length penalty of 12 and a gap penalty of 4. Appropriate parameters for maximal alignment by particular alignment software can be determined by one skilled in the art. In certain embodiments, the default parameters of the alignment software are used. In certain embodiments, the percentage identity "X" of a first amino acid sequence to a second sequence amino acid is calculated as 100×(Y/Z), where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be longer than the percent identity of the second sequence to the first sequence.

As a non-limiting example, whether any particular polynucleotide has a certain percentage sequence identity (e.g., is at least 80% identical, at least 85% identical, at least 90% identical, and in some embodiments, at least 95%, 96%, 97%, 98%, or 99% identical) to a reference sequence can, in certain embodiments, be determined using the Bestfit program (Wisconsin Sequence Analysis Package, Version 8 for Unix, Genetics Computer Group, University Research Park, 575 Science Drive, Madison, WI 5371 1). Bestfit uses the local homology algorithm of Smith and Waterman, Advances in Applied Mathematics 2: 482 489 (1981), to find the best segment of homology between two sequences. When using Bestfit or any other sequence alignment program to determine whether a particular sequence is, for instance, 95% identical to a reference sequence according to the present disclosure, the parameters are set such that the percentage of identity is calculated over the full length of the reference nucleotide sequence and that gaps in homology of up to 5% of the total number of nucleotides in the reference sequence are allowed.

In some embodiments, two nucleic acids or polypeptides of the disclosure are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. Identity can exist over a region of the sequences that is at least about 10, about 20, about 40-60 residues in length or any integral value therebetween, and can be over a longer region than 60-80 residues, for example, at least about 90-100 residues, and in some embodiments, the sequences are substantially identical over the full length of the sequences being compared, such as the coding region of a nucleotide sequence for example.

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. In some embodiments, conservative substitutions in the sequences of the polypeptides and antibodies of the disclosure do not abrogate the binding of the polypeptide or antibody containing the amino acid sequence, to the antigen(s), i.e., the PTGFRN to which the polypeptide or antibody binds. Methods of identifying nucleotide and amino acid conservative substitutions which do not eliminate antigen binding are well-known in the art (see, e.g., Brummell et al., Biochem. 32: 1 180-1 187 (1993); Kobayashi et al. Protein Eng. 12(10):879-884 (1999); and Burks et al. Proc. Natl. Acad. Sci. USA 94: 412-417 (1997)).

As used in the present disclosure and claims, the singular forms "a," "an," and "the" include plural forms unless the context clearly dictates otherwise.

It is understood that wherever embodiments are described herein with the language "comprising," otherwise analogous embodiments described in terms of "consisting of and/or "consisting essentially of are also provided.

The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

II. PTGFRN Binding Agents

The present disclosure provides agents that specifically bind PTGFRN. These agents are referred to herein as "PTGFRN binding agents."

In certain embodiments, the PTGFRN binding agents are antibodies, Immunoconjugates or polypeptides. In some embodiments, the PTGFRN binding agents are human or humanized antibodies. In some embodiments, the anti-PTGFRN binding molecules can be antibodies or antigen binding fragments that have the CDR sequences set forth in SEQ ID NOs: 5-10. In some embodiments, the anti-PTGFRN binding molecules can be antibodies or antigen binding fragments that have the CDR sequences set forth in of SEQ ID NOs: 11-100. In some embodiments, the PTGFRN binding molecules can be antibodies or antigen binding fragments that specifically bind to PTGFRN that comprise the CDRs of SEQ ID NOs: 11-100 with up to four (i.e. 0, 1, 2, 3, or 4) conservative amino acid substitutions per CDR.

In certain embodiments, the anti-PTGFRN antibodies or antigen binding fragments comprise the VH CDRs of SEQ ID NOs: 11-13. In certain embodiments, the anti-PTGFRN antibodies or antigen binding fragments comprise the VH CDRs of SEQ ID NOs: 14-16. In certain embodiments, the anti-PTGFRN antibodies or antigen binding fragments comprise the VL CDRs of SEQ ID NOs: 17-19. In certain embodiments, the anti-PTGFRN antibodies or antigen binding fragments comprise the VL CDRs of SEQ ID NOs: 20-22. In certain embodiments, the anti-PTGFRN antibodies or antigen binding fragments comprise the VL CDRs of SEQ ID NOs: 23-25.

In certain embodiments, the anti-PTGFRN antibodies or antigen binding fragments comprise the VH CDRs of SEQ ID NOs: 11-13 and VL CDRs of SEQ ID NOs: 17-19. In certain embodiments, the anti-PTGFRN antibodies or antigen binding fragments comprise the VH CDRs of SEQ ID NOs: 11-13 and VL CDRs of SEQ ID NOs: 20-22. In certain embodiments, the anti-PTGFRN antibodies or antigen binding fragments comprise the VH CDRs of SEQ ID NOs: 11-13 and VL CDRs of SEQ ID NOs: 23-25.

In certain embodiments, the anti-PTGFRN antibodies or antigen binding fragments comprise the VH CDRs of SEQ ID NOs: 14-16 and VL CDRs of SEQ ID NOs: 17-19. In certain embodiments, the anti-PTGFRN antibodies or antigen binding fragments comprise the VH CDRs of SEQ ID NOs: 14-16 and VL CDRs of SEQ ID NOs: 20-22. In certain embodiments, the anti-PTGFRN antibodies or antigen binding fragments comprise the VH CDRs of SEQ ID NOs: 14-16 and VL CDRs of SEQ ID NOs: 23-25.

In certain embodiments, the anti-PTGFRN antibodies or antigen binding fragments comprise the VH CDRs of SEQ ID NOs: 26-28. In certain embodiments, the anti-PTGFRN antibodies or antigen binding fragments comprise the VH CDRs of SEQ ID NOs: 29-31. In certain embodiments, the anti-PTGFRN antibodies or antigen binding fragments comprise the VL CDRs of SEQ ID NOs: 32-34.

In certain embodiments, the anti-PTGFRN antibodies or antigen binding fragments comprise the VH CDRs of SEQ ID NOs: 26-28 and VL CDRs of SEQ ID NOs: 32-34. In certain embodiments, the anti-PTGFRN antibodies or antigen binding fragments comprise the VH CDRs of SEQ ID NOs: 26-28 and VL CDRs of SEQ ID NOs: 32-34.

In certain embodiments, the anti-PTGFRN antibodies or antigen binding fragments comprise the VH sequence of SEQ ID NO: 101, 102, 106, 107, 109, 111, 113, 114, 117, 119, 121, 124, 126, or 128. In certain embodiments, the anti-PTGFRN antibodies or antigen binding fragments comprise the VL sequence of SEQ ID NO: 103, 104, 105, 108, 110, 112, 115, 116, 118, 120, 122, 123, 125, 127, 129, or 130. In some embodiments, the anti-PTGFRN binding molecules can be antibodies or antigen binding fragments that have the VH and VL sequences selected from SEQ ID NOs: 101-130. In certain embodiments, the anti-PTGFRN antibodies or antigen binding fragments comprise a VH or a VL having at least about 80%, at least about 85%, at least about 90%, at least about 95%, at least about 96%, at least about 97%, at least about 98%, or at least about 99% sequence identity to a sequence selected from SEQ ID NOs: 101-130.

In certain embodiments, the anti-PTGFRN antibody or antigen binding fragment thereof comprise the VH sequence of SEQ ID NO: 101 or 102 and the VL sequence of SEQ ID NO: 103, 104, or 105. In certain embodiments, the anti-PTGFRN antibody or antigen binding fragment thereof comprise the VH sequence of SEQ ID NO: 106 or 107 and the VL sequence of SEQ ID NO: 108.

In some embodiments, the anti-PTGFRN antibody or antigen-binding fragment thereof binds to the same PTGFRN epitope as an antibody selected from the group consisting of: an antibody comprising the polypeptide of SEQ ID NO: 101 and the polypeptide of SEQ ID NO:103; an antibody comprising the polypeptide of SEQ ID NO: 101 and the polypeptide of SEQ ID NO: 104; an antibody comprising the polypeptide of SEQ ID NO: 101 and the polypeptide of SEQ ID NO: 105; an antibody comprising the polypeptide of SEQ ID NO: 102 and the polypeptide of SEQ ID NO: 103; an antibody comprising the polypeptide of SEQ ID NO: 102 and the polypeptide of SEQ ID NO: 104; an antibody comprising the polypeptide of SEQ ID NO:102 and the polypeptide of SEQ ID NO: 105; an antibody comprising the polypeptide of SEQ ID NO:106 and the polypeptide of SEQ ID NO: 108; an antibody comprising the polypeptide of SEQ ID NO:107 and the polypeptide of SEQ ID NO: 108; an antibody comprising the polypeptide of SEQ ID NO: 109 and the polypeptide of SEQ ID NO: 110; an antibody comprising the polypeptide of SEQ ID NO: 111 and the polypeptide of SEQ ID NO: 112; an antibody comprising the polypeptide of SEQ ID NO: 113 and the polypeptide of SEQ ID NO: 115; an antibody comprising the polypeptide of SEQ ID NO: 113 and the polypeptide of SEQ ID NO: 116; an antibody comprising the polypeptide of SEQ ID NO: 114 and the polypeptide of SEQ ID NO:115; an antibody comprising the polypeptide of SEQ ID NO: 114 and the polypeptide of SEQ ID NO:116: an antibody comprising the polypeptide of SEQ ID NO: 117 and the polypeptide of SEQ ID NO: 118; an antibody comprising the polypeptide of SEQ ID NO: 119 and the polypeptide of SEQ ID NO: 120; an antibody comprising the polypeptide of SEQ ID NO: 121 and the polypeptide of SEQ ID NO: 122; an antibody comprising the polypeptide of SEQ ID NO:121 and the polypeptide of SEQ ID NO: 123; an antibody comprising the polypeptide of SEQ ID NO: 124 and the polypeptide of SEQ ID NO: 125; an antibody comprising the polypeptide of SEQ ID NO: 126 and the polypeptide of SEQ ID NO: 127; an antibody comprising the polypeptide of SEQ ID NO: 128 and the polypeptide of SEQ ID NO: 129; an antibody comprising the polypeptide of SEQ ID NO: 128 and the polypeptide of SEQ ID NO: 130; and an antibody comprising the polypeptide of SEQ ID NO:4 and the polypeptide of SEQ ID NO:2.

In some embodiments, the anti-PTGFRN antibody or antigen-binding fragment thereof competitively inhibits an antibody selected from the group consisting of: an antibody comprising the polypeptide of SEQ ID NO: 101 and the polypeptide of SEQ ID NO: 103; an antibody comprising the polypeptide of SEQ ID NO: 101 and the polypeptide of SEQ ID NO:104; an antibody comprising the polypeptide of SEQ ID NO: 101 and the polypeptide of SEQ ID NO: 105; an antibody comprising the polypeptide of SEQ ID NO: 102 and the polypeptide of SEQ ID NO: 103: an antibody comprising the polypeptide of SEQ ID NO: 102 and the polypeptide of SEQ ID NO: 104; an antibody comprising the polypeptide of SEQ ID NO: 102 and the polypeptide of SEQ ID NO:105; an antibody comprising the polypeptide of SEQ ID NO: 106 and the polypeptide of SEQ ID NO: 108; an antibody comprising the polypeptide of SEQ ID NO:107 and the polypeptide of SEQ ID NO: 108; an antibody comprising the polypeptide of SEQ ID NO:109 and the polypeptide of SEQ ID NO:110; an antibody comprising the polypeptide of SEQ ID NO:111 and the polypeptide of SEQ ID NO:112; an antibody comprising the polypeptide of SEQ ID NO: 113 and the polypeptide of SEQ ID NO: 115; an antibody comprising the polypeptide of SEQ ID NO: 113 and the polypeptide of SEQ ID NO:116; an antibody comprising the polypeptide of SEQ ID NO: 114 and the polypeptide of SEQ ID NO: 115; an antibody comprising the polypeptide of SEQ ID NO: 114 and the polypeptide of SEQ ID NO:116; an antibody comprising the polypeptide of SEQ ID NO: 117 and the polypeptide of SEQ ID NO:118; an antibody comprising the polypeptide of SEQ ID NO: 119 and the polypeptide of SEQ ID NO:120; an antibody comprising the polypeptide of SEQ ID NO: 121 and the polypeptide of SEQ ID NO:122; an antibody comprising the polypeptide of SEQ ID NO: 121 and the polypeptide of SEQ ID NO: 123; an antibody comprising the polypeptide of SEQ ID NO: 124 and the polypeptide of SEQ ID NO: 125; an antibody comprising the polypeptide of SEQ ID NO: 126 and the polypeptide of SEQ ID NO: 127; an antibody comprising the polypeptide of SEQ ID NO: 128 and the polypeptide of SEQ ID NO: 129; an antibody comprising the polypeptide of SEQ ID NO:128 and the polypeptide of SEQ ID NO: 130; and an antibody comprising the polypeptide of SEQ ID NO:4 and the polypeptide of SEQ ID NO:2.

In some embodiments, the anti-PTGFRN antibody or antigen-binding fragment thereof comprises a heavy chain variable region (VH) and light chain variable region (Vl), wherein the VH and VL comprise complementarity determining regions CDR1, CDR2, and CDR3, and wherein VH-CDR1, VH-CDR2, and VH-CDR3 and the VL-CDR1, VL-CDR2, and VL-CDR3, respectively, comprise the polypeptide sequences selected from the group consisting of: SEQ ID NOs: 11, 12, and 13 and SEQ ID NOs: 17, 18, and 19, respectively; SEQ ID NOs: 11, 12, and 13 and SEQ ID NOs: 20, 21, and 22, respectively: SEQ ID NOs: 11, 12, and 13 and SEQ ID NOs: 23, 24, and 25, respectively; SEQ ID NOs: 14, 15, and 16 and SEQ ID NOs: 17, 18, and 19, respectively; SEQ ID NOs: 14, 15, and 16 and SEQ ID NOs: 20, 21, and 22, respectively; SEQ ID NOs: 14, 15, and 16 and SEQ ID NOs. 23, 24, and 25, respectively; SEQ ID NOs: 26, 27, and 28 and SEQ ID NOs: 32, 33, and 34, respectively; SEQ ID NOs: 29, 30, and 31 and SEQ ID NOs: 32, 33, and 34, respectively; SEQ ID NOs: 35, 36, and 37 and SEQ ID NOs: 38, 39, and 40, respectively; SEQ ID NOs: 41, 42, and 43 and SEQ ID NOs: 44, 45, and 46, respectively; SEQ ID NOs: 47, 48, and 49 and SEQ ID NOs: 53, 54, and 55, respectively; SEQ ID NOs: 47, 48, and 49 and SEQ ID NOs: 56, 57, and 58, respectively; SEQ ID NOs: 50, 51, and 52 and SEQ ID NOs: 53, 54, and 55, respectively; SEQ ID NOs: 50, 51, and 52 and SEQ ID NOs: 56, 57, and 58, respectively; SEQ ID NOs: 59, 60, and 61 and SEQ ID NOs: 62, 63, and 64, respectively; SEQ ID NOs: 65, 66, and 67 and SEQ ID NOs: 68, 69, and 70, respectively; SEQ ID NOs: 71, 72, and 73 and SEQ ID NOs: 74, 75, and 76, respectively; SEQ ID NOs: 71, 72, and 73 and SEQ ID NOs: 77, 78, and 79, respectively; SEQ ID NOs: 80, 81, and 82 and SEQ ID NOs: 83, 84, and 85, respectively; SEQ ID NOs: 86, 87, and 88 and SEQ ID NOs: 89, 90, and 91, respectively; SEQ ID NOs: 92, 93, and 94 and SEQ ID NOs: 95, 96, and 97, respectively; SEQ ID NOs: 92, 93, and 94 and SEQ ID NOs: 98, 99, and 100, respectively; SEQ ID NOs: 8, 9, and 10 and SEQ ID NOs: 5, 6, and 7, respectively; and variants of (a) to (w) comprising 1, 2, 3, or 4 conservative amino acid substitutions.

In some embodiments, the anti-PTGFRN antibody or antigen-binding fragment thereof comprises polypeptide sequences that are at least 90%, 95%, 99%, or 100% identical to polypeptide sequences selected from the group consisting of: SEQ ID NO: 101 and SEQ ID NO: 103; SEQ ID NO: 101 and SEQ ID NO: 104; SEQ ID NO: 101 and SEQ ID NO: 105; SEQ ID NO: 102 and SEQ ID NO: 103; SEQ ID NO: 102 and SEQ ID NO: 104; SEQ ID NO: 102 and SEQ ID NO:105; SEQ ID NO: 106 and SEQ ID NO:108; SEQ ID NO:107 and SEQ ID NO:108; SEQ ID NO:109 and SEQ ID NO:110; SEQ ID NO:111 and SEQ ID NO: 112; SEQ ID NO: 113 and SEQ ID NO: 115; SEQ ID NO: 113 and SEQ ID NO: 116; SEQ ID NO: 114 and SEQ ID NO: 115; SEQ ID NO:114 and SEQ ID NO:116; SEQ ID NO: 117 and SEQ ID NO: 118; SEQ ID NO: 119 and SEQ ID NO:120; SEQ ID NO: 121 and SEQ ID NO: 122; SEQ ID NO:121 and SEQ ID NO: 123; SEQ ID NO: 124 and SEQ ID NO: 125; SEQ ID NO: 126 and SEQ ID NO: 127; SEQ ID NO: 128 and SEQ ID NO: 129; SEQ ID NO: 128 and SEQ ID NO: 130; and SEQ ID NO:4 and SEQ ID NO:2.

In some embodiments, the antibody or antigen binding fragment thereof is internalized. In some embodiments, the antibody or antigen binding fragment thereof imurine, human, humanized, or chimeric. In some embodiments, the antibody or antigen binding fragment thereof is CDR-grafted, recombinant, or resurfaced. In some embodiments, the antibody or antigen binding fragment thereof further comprises human or human-derived heavy and light chain variable region frameworks. In some embodiments, the antibody or antigen binding fragment thereof comprises an IgG1 or IgG2 constant region. In some embodiments, the antibody or antigen binding fragment thereof is capable of inducing cell death. In some embodiments, the antibody or antigen binding fragment thereof binds to human PTGFRN. In some embodiments, the antibody or antigen binding fragment thereof binds to murine PTGFRN. In some embodiments, the antibody is a full length antibody. In some embodiments, it is an antigen binding fragment. In some embodiments, the antibody or antigen binding fragment thereof comprises a Fab, Fab', F(ab')2, Fd, single chain Fv or scFv, disulfide linked Fv, V-NAR domain, IgNar, intrabody, IgGΔCH2, minibody, F(ab')3, tetrabody, triabody, diabody, single-domain antibody, DVD-Ig, Fcab, mAb2, (scFv)2, or scFv-Fc.

In some embodiments, one or more functional moieties may be conjugated to an antibody of the disclosure. The number of functional moieties per antibody can be varied by one skilled in the art using known techniques. Typically, at least one functional moiety will be conjugated per antibody. In some embodiments, the ratio of functional moieties per antibody may be from about 1 to about 8, from about 2 to about 8, from about 3 to about 8, from about 4 to about 8, from about 5 to about 8, from about 6 to about 8, or from about 7 to about 8. In some embodiments, an antibody conjugate of the disclosure may comprise 1 functional moiety, 2 functional moieties, 3 functional moieties, 4 functional moieties, 5 functional moieties, 6 functional moieties, 7 functional moieties, or 8 functional moieties. Typically, the number of functional moieties per antibody may be expressed a drug antibody ratio (DAR). The number of functional moieties per antibody can be determined using any technique known in the art, for example, UV spectroscopy, mass spectroscopy, immuno assay, radiometric methods, hydrophobic interaction chromatography (HIC), electrophoresis, or HPLC.

In some embodiments, a functional moiety may be a drug. In some embodiments, a functional moiety may be a drug used to treat cancer, e.g., a cytotoxic reagent. Any cytotoxic reagent known to those skilled in the art may be used in the practice of the disclosure, such as enzymes, toxins, peptides, and anthracyclines. Examples of cytotoxic reagents include, but are not limited to, nucleoside antagonists (e.g., 5-fluorouracil, 6-mercaptopurine, arabinosylcytosine, capecitabine, clofarabine, cytarabine, dacarbazine, fludarabine, gemcitabine, and nelarabine), intercalating agents (e.g., oxaliplatin, cisplatin, and carboplatin), microtubule assembly inhibitors (e.g., auristatins, monomethyl auristatin E, monomethyl auristatin F, docetaxel, paclitaxel, ixabepilone, vinca alkaloids, vindesine, vincristine, vinorelbine, vinblastine, and maytansinoids, mertansine), folate inhibitors (e.g., methotrexate and pemetrexed), ribosome inactivating proteins such as saporin, toxins such as ricin and cholera toxin. In certain embodiments, the cytotoxic reagent is an anthracycline, an auristatin, a camptothecin, a combretastatin, a dolastatin, a duocarmycin, an enediyne, a geldanamycin, an indolino-benzodiazepine dimer, a maytansine, a puromycin, a pyrrolobenzodiazepine dimer, a taxane, a vinca alkaloid, a tubulysin, a hemiasterlin, a spliceostatin, a pladienolide, or a calicheamicin. In some embodiments, M may be monomethyl auristatin E, monomethyl auristatin F, maytansinoid DM1, maytansinoid DM4, calicheamicin, ozogamicin, α-amanitin, yttrium-90, or iodine-131.

The immunoconjugates can, according to some embodiments described herein, be internalized into cells. The immunoconjugate, therefore, can exert a therapeutic effect when it is taken up by, or internalized, by a PTGFRN-expressing cell. In some particular embodiments, the immunoconjugate comprises an antibody, antibody fragment, or polypeptide, linked to a cytotoxic agent by a cleavable linker, and the cytotoxic agent is cleaved from the antibody, antibody fragment, or polypeptide, wherein it is internalized by a PTGFRN-expressing cell.

The present disclosure further provides an antibody conjugate of the formula: Ab-L-M, wherein: (a) Ab is an antibody or antigen binding fragment thereof that specifically binds to PTGFRN; (b) L is a linker; and (c) M is a functional moiety. In some embodiments, the Ab in the antibody conjugate is an antibody or antigen binding fragment thereof of any one of claims 1-18. In some embodiments, the M in the antibody conjugate is selected from the group consisting of a cytotoxic reagent, an immunomodulating agent, an imaging agent, a therapeutic protein, a biopolymer, and an oligonucleotide. In some embodiments, the M is a cytotoxic reagent. In some embodiments, the cytotoxic reagent is selected from the group consisting of an anthracycline, an auristatin, a camptothecin, a combretastatin, a dolastatin, a duocarmycin, an enediyne, a geldanamycin, an indolino-benzodiazepine dimer, a maytansine, a puromycin, a pyrrolobenzodiazepine dimer, a taxane, a vinca alkaloid, a tubulysin, a hemiasterlin, a spliceostatin, a pladienolide, and calicheamicin. In some embodiments, the cytotoxic reagent is selected from monomethyl auristatin E, monomethyl auristatin F, maytansinoid DM1, maytansinoid DM4, calicheamicin, ozogamicin, α-amanitin, yttrium-90, and iodine-131. In some embodiments, the linker in the antibody conjugate is selected from the group consisting of a cleavable linker, a non-cleavable linker, a hydrophilic linker, and a dicarboxylic acid based linker. In some embodiments, the antibody conjugate provided in the present disclosure binds PTGFRN and is internalized.

In certain embodiments, the PTGFRN-binding agents (e.g., antibodies, antigen binding fragments thereof, and/or antibody drug conjugates) have one or more of the following effects: inhibit proliferation of tumor cells, reduce the tumorigenicity of a tumor by reducing the frequency of cancer stem cells in the tumor, inhibit tumor growth, increase survival, trigger cell death of tumor cells, differentiate tumorigenic cells to a non-tumorigenic state, or prevent metastasis of tumor cells.

In certain embodiments, the PTGFRN-binding agents bind to cell surface PTGFRN antigens. In certain embodiments, the PTGFRN-binding agents bind to the extracellular domain (ECD) of PTGFRN. In certain embodiments, cancer cells have multiple cell surface PTGFRN antigens. In certain embodiments, the PTGFRN-binding agents are internalized into the cells.

In certain embodiments, the PTGFRN-binding agents bind to the same epitope on cell surface PTGFRN as 33B7. In certain embodiments, the PTGFRN-binding agents bind to different epitopes on cell surface PTGFRN than 33B7.

In certain embodiments, the PTGFRN-binding agents are capable of cell killing. In certain embodiments, the cell killing is effected by the anti-PTGFRN antibodies. In certain embodiments, the cell killing is effected by the cytotoxic drug conjugated to the anti-PTGFRN antibodies. In certain embodiments, the cell killing is effected by the anti-PTGFRN antibodies and the cytotoxic drug conjugated to the anti-PTGFRN antibodies.

III. Polynucleotides

In certain embodiments, the disclosure encompasses polynucleotides comprising polynucleotides that encode a polypeptide that specifically binds PTGFRN or a fragment of such a polypeptide. For example, the disclosure provides a polynucleotide comprising a nucleic acid sequence that encodes an antibody to a human PTGFRN or encodes a fragment of such an antibody. The polynucleotides of the disclosure can be in the form of RNA or in the form of DNA. DNA includes cDNA, genomic DNA, and synthetic DNA; and can be double-stranded or single-stranded, and if single stranded can be the coding strand or non-coding (anti-sense) strand.

In certain embodiments, the polynucleotides are isolated. In certain embodiments, the polynucleotides are substantially pure.

The disclosure also provides an isolated polynucleotide. In certain embodiments, the polynucleotide comprises a sequence encoding a polypeptide comprising a sequence selected from the group consisting of SEQ ID NOs: 2, 4, and 101-130. In some embodiments, the polynucleotide comprises a sequence that encodes a polypeptide at least 90%, 95%, 99%, or 100% identical to a sequence selected from the group consisting of SEQ ID NOs: 2, 4, and 101-130. Also provided is a polynucleotide having at least about 90%, at least about 95%, at least about 96%, at least about 97%, at least about 98%, or at least about 99% sequence identity to SEQ ID NOs: 1, 2, and 131-160.

In certain embodiments the polynucleotides comprise the coding sequence for the mature polypeptide fused in the same reading frame to a polynucleotide which aids, for example, in expression and secretion of a polypeptide from a host cell (e.g. a leader sequence which functions as a secretory sequence for controlling transport of a polypeptide from the cell). The polypeptide having a leader sequence is a preprotein and can have the leader sequence cleaved by the host cell to form the mature form of the polypeptide. The polynucleotides can also encode for a proprotein which is the mature protein plus additional 5' amino acid residues. A mature protein having a prosequence is a proprotein and is an inactive form of the protein. Once the prosequence is cleaved, an active mature protein remains.

In certain embodiments, the polynucleotides comprise the coding sequence for the mature polypeptide fused in the same reading frame to a marker sequence that allows, for example, for purification of the encoded polypeptide.

The present disclosure further relates to variants of the hereinabove described polynucleotides encoding, for example, fragments, analogs, and derivatives.

The polynucleotide variants can contain alterations in the coding regions, non-coding regions, or both. In some embodiments, the polynucleotide variants contain alterations, which produce silent substitutions, additions, or deletions, but do not alter the properties or activities of the encoded polypeptide. In some embodiments, nucleotide variants are produced by silent substitutions due to the degeneracy of the genetic code. Polynucleotide variants can be produced for a variety of reasons, e.g., to optimize codon expression for a particular host (change codons in the human mRNA to those preferred by a bacterial host such as *E. coli*).

Vectors and cells comprising the polynucleotides described herein are also encompassed by the present disclosure.

IV. Pharmaceutical Compositions and Methods of Use

In some embodiments, antibodies and/or antibody conjugates of the disclosure may be formulated as pharmaceutical compositions. Pharmaceutical compositions of the disclosure will typically comprise from about 0.1% to about 75% by weight of an antibody or antibody drug conjugate of the disclosure. In some embodiments, a pharmaceutical composition of the disclosure may comprise from about 0.2% to about 75%, from about 0.5% to about 75%, from about 1% to about 75%, from about 2% to about 75%, from about 5% to about 75%, from about 10% to about 75%, from about 20% to about 75%, or from about 50% to about 75% by weight of an antibody or antibody drug conjugate of the disclosure.

Pharmaceutical compositions of the disclosure may be formulated in any manner known to those skilled in the art. Typically, pharmaceutical compositions of the disclosure are formulated as injectable compositions which may be liquid solutions or suspensions or solid forms to be dissolved or suspended in liquid prior to injection. Pharmaceutical compositions of the disclosure may be formulated for delayed release, for example, may be formulated for depot injections.

A pharmaceutical composition of the disclosure will typically comprise one or more pharmaceutically acceptable carrier. As used herein, “pharmaceutically acceptable carrier” includes any and all aqueous solvents (e.g., water, alcoholic/aqueous solutions, saline solutions, parenteral vehicles, such as sodium chloride, Ringer’s dextrose, etc.), non-aqueous solvents (e.g., propylene glycol, polyethylene glycol, vegetable oil, and injectable organic esters, such as ethyloleate), dispersion media, coatings, surfactants, anti-oxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, such like materials and combinations thereof, as would be known to one of ordinary skill in the art. The pH and exact concentration of the various components in a pharmaceutical composition are adjusted according to well-known parameters.

The present disclosure also provides methods of treatment using the antibodies of the disclosure. Methods of the disclosure will typically comprise administration of a pharmaceutical composition of the disclosure to a patient in need thereof. The quantity to be administered, both according to number of treatments and dose, may be determined by those skilled in the art. Determination of the quantity and timing of administration of a pharmaceutical composition of the disclosure can be made by consideration of factors such as body weight, the age, health, and sex of the subject, the type of disease being treated, the extent of disease penetration, previous or concurrent therapeutic interventions, idiopathy of the patient, the route of administration, and the potency, stability, and toxicity of the particular therapeutic substance.

In some embodiments, antibodies of the disclosure may be used for imaging applications. Typically, for imaging applications, antibodies of the disclosure may be conjugated to a functional moiety suitable for imaging. Functional moieties suitable for imaging include, but are not limited to, moieties that may be detected by microscopy, e.g. fluorescent microscopy, confocal microscopy, or electron microscopy. Other functional moieties may be detected by other analytical techniques, for example, by magnetic resonance imaging, tomography, such as gamma (SPECT/CT, planar) and positron emission tomography (PET/CT), radiography, or ultrasound. Functional moieties suitable for use in imaging applications of the disclosure may include luminescent molecules, chemiluminescent molecules, fluorochromes, fluorescent quenching agents, colored molecules, radioisotopes, scintillants, massive labels (for detection via mass changes), biotin, avidin, streptavidin, protein A, protein G, antibodies or fragments thereof, Grb2, polyhistidine, Ni2+, Flag tags, myc tags, heavy metals, enzymes, alkaline phosphatase, peroxidase, luciferase, electron donors/acceptors, acridinium esters, and colorimetric substrates.

The PTGFRN-binding agents (including antibodies, immunoconjugates, and polypeptides) of the disclosure are useful in a variety of applications including, but not limited to, therapeutic treatment methods, such as the treatment of cancer. In some embodiments, the cancer is a medulloblastoma, an epidermoid carcinoma, a mesothelioma, an osteosarcoma, a spindle cell sarcomatoid carcinoma, a choriocarcinoma, a rhabdomyosarcoma, a neuroblastoma, a leiomyosarcomas, a triple negative breast carcinoma, a head and neck carcinoma, castrate resistant prostate carcinoma, squamous carcinoma, lung squamous carcinoma, Ovarian carcinoma, and pancreatic carcinoma, or any metastases thereof. In certain embodiments, the agents are useful for inhibiting tumor growth, inducing differentiation, reducing tumor volume, and/or reducing the tumorigenicity of a tumor. The methods of use can be in vitro, ex vivo, or in vivo methods.

In certain embodiments, anti-PTGFRN antibodies and immunoconjugates of the disclosure are useful for detecting the presence of PTGFRN in a biological sample. The term “detecting” as used herein encompasses quantitative or qualitative detection. In certain embodiments, a biological sample comprises a cell or tissue. In certain embodiments, such tissues include normal and/or cancerous tissues that express PTGFRN at higher levels relative to other tissues.

In certain embodiments, the disclosure provides a method of detecting the presence of PTGFRN in a biological sample. In certain embodiments, the method comprises contacting the biological sample with an anti-PTGFRN antibody under conditions permissive for binding of the anti-PTGFRN antibody to PTGFRN, and detecting whether a complex is formed between the anti-PTGFRN antibody and PTGFRN.

In certain embodiments, the disclosure provides a method of diagnosing a disorder, such as cancer. In certain embodiments, the method comprises contacting a test cell with an anti-PTGFRN antibody; determining the level of expression (either quantitatively or qualitatively) of PTGFRN by the test cell by detecting binding of the anti-PTGFRN antibody to PTGFRN; and comparing the level of expression of PTGFRN by the test cell with the level of expression of PTGFRN by a control cell (e.g., a normal cell of the same tissue origin as the test cell or a cell that expresses PTGFRN at levels comparable to such a normal cell), wherein a higher level of expression of PTGFRN by the test cell as compared to the control cell indicates the presence of a disorder associated with increased expression of PTGFRN. In certain embodiments, the test cell is obtained from an individual suspected of having a disorder associated with increased expression of PTGFRN. In certain embodiments, the disorder is a cell proliferative disorder, such as a cancer or a tumor.

In certain embodiments, a method of diagnosis or detection, such as those described above, comprises detecting binding of an anti-PTGFRN antibody to PTGFRN expressed on the surface of a cell or in a membrane preparation obtained from a cell expressing PTGFRN on its surface. In certain embodiments, the method comprises contacting a cell with an anti-PTGFRN antibody under conditions permissive for binding of the anti-PTGFRN antibody to PTGFRN, and detecting whether a complex is formed between the anti-PTGFRN antibody and PTGFRN on the cell surface. An exemplary assay for detecting binding of an anti-PTGFRN antibody to PTGFRN expressed on the surface of a cell is a "FACS" assay.

Certain other methods can be used to detect binding of anti-PTGFRN antibodies to PTGFRN. Such methods include, but are not limited to, antigen-binding assays that are well known in the art, such as western blots, radioimmunoassays, ELISA (enzyme linked immunosorbent assay), "sandwich" immunoassays, immunoprecipitation assays, fluorescent immunoassays, protein A immunoassays, and immunohistochemistry (IHC).

In certain embodiments, anti-PTGFRN antibodies are labeled. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction.

In certain embodiments, the disease treated with the PTGFRN-binding agent (e.g., an anti-PTGFRN antibody or conjugate) is a cancer. In certain embodiments, the cancer is characterized by PTGFRN expressing cells to which the PTGFRN-binding agent (e.g., antibody or conjugate) binds.

The present disclosure provides for methods of treating cancer comprising administering a therapeutically effective amount of a PTGFRN-binding agent to a subject (e.g., a subject in need of treatment). In certain embodiments, the cancer is selected from carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer. In some embodiments, the cancer is a medulloblastoma, an epidermoid carcinoma, a mesothelioma, an osteosarcoma, a spindle cell sarcomatoid carcinoma, a choriocarcinoma, a rhabdomyosarcoma, a neuroblastoma, a leiomyosarcomas, a triple negative breast carcinoma, a head and neck carcinoma, castrate resistant prostate carcinoma, squamous carcinoma, lung squamous carcinoma, Ovarian carcinoma, and pancreatic carcinoma, or any metastases thereof The present disclosure further provides methods for inhibiting tumor growth using the antibodies or conjugates described herein. In certain embodiments, the method of inhibiting the tumor growth comprises contacting the cell with a PTGFRN-binding agent (e.g., antibody or conjugate) in vitro. For example, an immortalized cell line or a cancer cell line that expresses PTGFRN is cultured in medium to which is added the antibody or other agent to inhibit tumor growth. In some embodiments, tumor cells are isolated from a patient sample such as, for example, a tissue biopsy, pleural effusion, or blood sample and cultured in medium to which is added a PTGFRN-binding agent to inhibit tumor growth.

In some embodiments, the method of inhibiting tumor growth comprises contacting the tumor or tumor cells with the PTGFRN-binding agent (e.g., antibody or conjugate) in vivo. In certain embodiments, contacting a tumor or tumor cell with a PTGFRN-binding agent is undertaken in an animal model. For example, PTGFRN-binding agents can be administered to xenografts expressing one or more PTGFRNs that have been grown in immunocompromised mice to inhibit tumor growth.

In certain embodiments, the method of inhibiting tumor growth comprises administering to a subject a therapeutically effective amount of a PTGFRN-binding agent. In certain embodiments, the subject is a human. In certain embodiments, the subject has a tumor or has had a tumor removed.

In certain embodiments, the tumor expresses the PTGFRN to which the PTGFRN-binding agent or antibody binds. In certain embodiments, the tumor overexpresses the human PTGFRN.

In some embodiments, the disclosure provides a method for treating a disorder associated with PTGFRN function or expression in a subject comprising administering to a subject in need thereof an effective amount of a pharmaceutical composition of the disclosure. Disorders that may be treated include cancer. Cancers that may be treated include, but are not limited to, medulloblastomas, epidermoid tumors, mesotheliomas, osteosarcomas, spindle cell sarcomatoid carcinomas, choriocarcinomas, squamous carcinoma, or any metastases thereof.

In some embodiments, the disclosure provides a method for decreasing tumor growth or progression in a subject who has a PTGFRN-expressing tumor, comprising administering to the subject in need thereof an effective amount of a pharmaceutical composition of the disclosure.

In some embodiments, the disclosure provides a method for decreasing metastasis of PTGFRN-expressing cancer cells in a subject, comprising administering to the subject in need thereof an effective amount of a pharmaceutical composition of the disclosure.

In some embodiments, the disclosure provides a method for inducing tumor regression in a subject who has a PTGFRN-expressing tumor, comprising administering to the subject in need thereof an effective amount of a pharmaceutical composition of the disclosure.

In some embodiments, the disclosure provides a method for preventing tumor regrowth in a subject who has had a PTGFRN-expressing tumor, comprising administering to the subject in need thereof an effective amount of a pharmaceutical composition of the disclosure.

In some embodiments, the present disclosure provides a method for ameliorating symptoms in a subject who has, or has had, a PTGFRN-expressing tumor, comprising administering to the subject in need thereof an effective amount of a pharmaceutical composition of the disclosure.

In some embodiments, the disclosure provides a method for imaging a cell, comprising contacting the cell with an antibody or antigen binding fragment thereof of the disclosure or an antibody conjugate of the disclosure; and detecting the antibody or antigen binding fragment thereof or the antibody conjugate.

In some embodiments, the present disclosure provides a method for identifying the expression of PTGFRN in a tumor, comprising (1) obtaining a sample of the tumor, (2) contacting the sample with the antibody or antigen binding fragment thereof or the antibody conjugate encompassed by the disclosure; and (3) detecting the antibody or antigen binding fragment thereof or the conjugate. In some embodiments, the detecting is by immunochemistry. In some embodiments, the method for identifying the expression of PTGFRN in a tumor can be done by immunochemistry (IHC). In other embodiments, such methods can be done by, but are not limited to, antigen-binding assays that are well known in the art, such as western blots, radioimmunoassays, ELISA (enzyme linked immunosorbent assay), "sandwich" immunoassays, immunoprecipitation assays, fluorescent immunoassays, and protein A immunoassays.

EXAMPLES

The present disclosure provides monoclonal antibodies (mAbs) (e.g., antibody 33B7, also designated here as AG02, or antibody 4F4) that specifically bind a cell surface protein (CSP) expressed on cancer cells. The target cell surface protein bound by monoclonal antibodies of the disclosure was identified by mass spectrophotometry as Prostaglandin F2 Receptor Inhibitor (PTGFRN). PTGFRN is preferentially expressed in certain cancer cells, particularly medulloblastoma and mesothelioma. Monoclonal antibodies of the disclosure bind to cells naturally expressing PTGFRN and to cells transfected to express PTGFRN.

Monoclonal antibodies of the disclosure can also be monoclonal antibodies that are internalized by PTGFRN expressing cancer cells and as such are potential payload carriers to kill targeted cells. One example of such a use of the monoclonal antibodies of the disclosure is provided below in the form of a generic type of antibody-drug-conjugate (ADC) consisting of a monoclonal antibody of the disclosure linked to saporin, a ribosome inactivating protein (RIP), a natural glycoside which possess cytotoxic activity. Saporin is widely used in proof-of-concept ADC studies. Using this ADC, we demonstrated both in vitro and in vivo, the selective effect on target cells while cells not expressing the target CSP were unaffected.

These data demonstrated that PTGFRN to which these mABs bind is a valuable target for development of novel anti-cancer agent specific for certain cancers.

It is understood that the examples and embodiments described herein are for illustrative purposes only and that various modifications or changes in light thereof will be suggested to persons skilled in the art and are to be included within the spirit and purview of this application.

Example 1: Screening of Mouse Antibodies

Antibodies were raised as part of a mouse monoclonal antibody library against cell surface proteins (CSPs) found on human cancer cells. Antibodies were screened against several known cancer cells including sarcoma and pediatric cancer cell lines to identify antibodies specific for cancer CSPs as potential druggable candidates. Subsequent screening identified antibodies that not only bound to cancer CSPs but also were internalized into the cancer cells. Such antibody candidates were identified for further development and characterization. One of these antibodies (33B7) was identified as having superior characteristics and marked as a primary candidate for further development and characterization for its therapeutic potential.

Example 2: Identification of the Target for 33B7

To identify the target of 33B7, CSPs on 33B7 positive cells were biotinylated and the cells were homogenized and then processed by differential centrifugation to obtain a plasma membrane preparation. Plasma membranes were solubilized in 1.0% Triton® X100 solution and used as starting material for purification and identification of the 33B7 target. 2×108 SCSC cells were collected from 2 roller bottles with PBS-1 mM EDTA followed by three washes in PBS. Using Thermo Scientific's EZ-Link™ Sulfo-NHS-LC-Biotinylation Kit, the cell surface of these cells were biotinylated for 2 hours at 4° C. After 2 hours, the reaction was quenched with 3 washes of 100 mM Tris®-PBS. The solution was aliquoted into individual 1.5 mL Eppendorf Tubes® and spun down for 15 minutes at 14,000 RPM.

The supernatant was removed, and the membrane pellets were lysed in 1% Triton® X-100 in PBS followed by sonication and centrifugation. The protein concentration was determined by a microBCA.

Protein G beads (50 µl) were added to two 1 mg aliquots of the lysate, and +4 µg of pooled mouse IgG was added to preclear nonspecific-binding. Combined beads, lysate, and mouse IgG were incubated on a rotator at 4° C. for 1.5 hours. After incubation, the beads were spun down and the cleared supernatant was added to 50 µL of Protein G Beads in the presence of 20 µg of 33B7 antibody. Control was done by having a second aliquot of lysed membrane incubated with 50 µL of Protein G Beads +20 µg of unrelated mouse monoclonal antibody. Incubation was carried out overnight at 4° C.

The next day, beads were washed with 1% Triton® X-100 in PBS. After the last wash, beads were incubated with 150 µL of 50 mM Glycine (pH 1.9) to elute proteins bound to 33B7 antibody. A second round of elution was performed and the supernatants combined. This 300 µL was added to 35 µL of 10× Neutralization buffer (pH: 7.4).

Two 100 µL aliquots of streptavidin beads (Dynabeads® MyOne™ Streptavidin C1, from Thermo-Fisher) were washed in 1% Triton® X-100 in PBS 3 times. After the washes, the 300 µL, of eluted fraction from control and test antibodies were added to tubes of the streptavidin beads followed by overnight incubation.

The next day, the solutions with beads were spun down and beads were washed 8 times with 1% Triton® X-100 in PBS. 30 µL of 2× Laemmli SDS sample buffer+100 mM DTT were added to each tube, and heated to 100° C. for 5 minutes. The samples were frozen and thawed 2 times, then reheated to 95° C. for another 5 minutes.

33B7 and IgG control samples were run on two 4-12% Bis-Tris® Polyacrylamide Gels one for western blot and one for Colloidal Blue staining. For Western blot the membrane was incubated with streptavidin HRP to detect band that were biotinylated and were immunoprecipitated by 33B7 antibody.

The second gel was washed and stained with colloidal blue for 3 hours. After 3 hours, the gel was washed and left to rinse overnight in water. Streptavidin-HRP western blot revealed the presence of unique biotinylated band with an apparent molecular weight of 135 kDa that was only visible in the 33B7 sample and not in the IgG control sample. The gel stained by colloidal blue show a corresponding band at the similar molecular weight as the biotinylated band that was cut with scalpel and sent for in gel digestion and mass spectrometry identification. Gel corresponding to the IgG control sample was also cut at the same position as the one for 33B7 samples and was used as a negative control for Mass Spec identification. Mass spectrometry sequencing identified PTGFRN as a candidate for the target recognized and immunoprecipitated by 33B7 antibody.

Figure 1B:
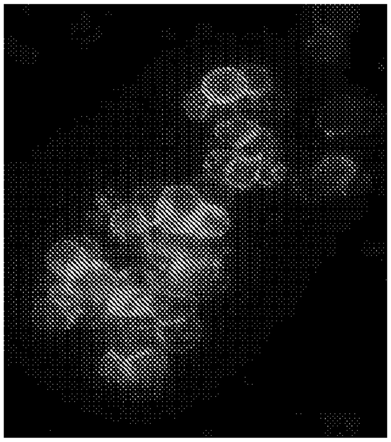

In order to confirm that the PTGFRN target identified by Mass spec was indeed the protein recognized by 33B7, human PTGFRN cDNA was synthesized and inserted into a mammalian pcDNA3 expression vector. PTGFRN expression vector was transiently transfected into human kidney cells Hek293 cells (which are 33B7 negative and do not express PTGFRN as tested using commercially available anti-PTGFRN). After transfection, expression of PTGFRN in the cells was verified by western blot using anti-PTGFRN antibody. The PTGFRN transfected cells could now bind 33B7 in contrast to empty vector Hek293 cells that were negative for PTGFRN and for 33B7 binding. FIG. 1A shows rhodamine-mIgG/33B7 does not bind with PTGFRN negative Hek-293 cells while it binds to the Hek-293 cells transfected with PTGFRN cDNA (FIG. 1B). Thus, 33B7 appears specific for PTGFRN and is able to bind to PTGFRN on the cell surface. These data confirmed that expression of PTGFRN identified by Mass Spec is associated with positive 33B7 binding.

Example 3: 33B7 Binding to Cancer Cell Lines

Figure 2:
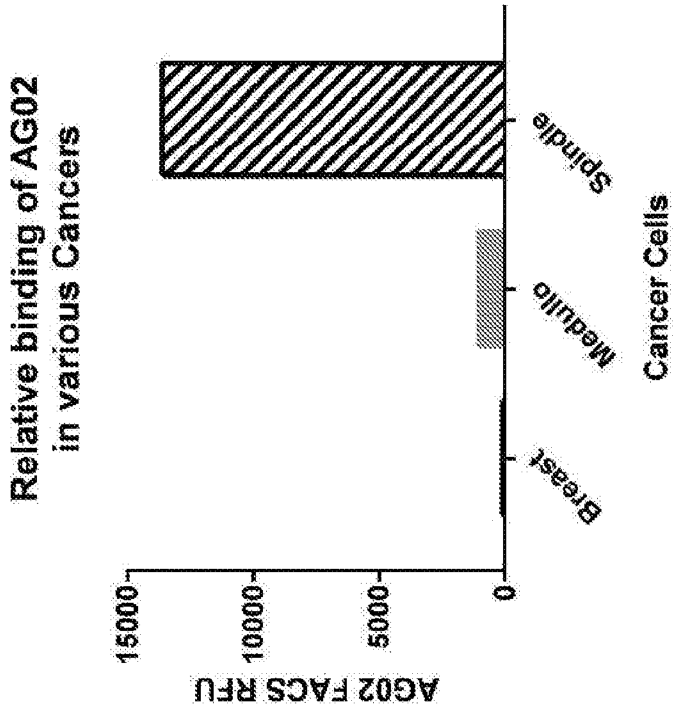
FIG. 2 is a bar graph showing relative binding of 33B7 (AG02) to various cancer cells.

Several cancer cell lines were tested by flow for their ability to bind 33B7 antibody (FIG. 2). Cells were detached with PBS-EDTA and then washed several times with PBS and with binding buffer. Cells were counted and spun down and then resuspended at a density of ~5×105 cells/100 μL in DMEM/F12 medium with 0.5% BSA. The cells were added to a V-bottom 96-well plate.

The plates were centrifuged, the supernatant removed, and the cells were resuspended in 100 μL of a 5 μg/mL solution of primary 33B7 antibody in DMEM/F12+0.5% BSA. The cells were incubated at 4° C. for 1 hour.

After 1 hour, the cells were washed in 200 μL of cold PBS, resuspended in 100 μL of a 10 μg/mL solution of secondary antibody, rabbit anti-mouse IgG in DMEM/F12+0.5% BSA, and incubated at 4° C. for 1 hour.

After 1 hour, the cells were washed in 200 μL of PBS, resuspended in 100 μL of a 20 μg/mL solution of Alexa Fluor® 647 goat anti-rabbit IgG in DMEM/F12+0.5% BSA, and incubated at 4° C. for 1 hour. When using cells for flow assay, the fluorescent protein used is Alexa Fluor®_647. The cells are washed twice with cold PBS. For flow assay, cells can be run directly in a flow measuring device such as Intellicyt® (Albuquerque, N. Mex.).

To visualize internalization, the method of choice was immunofluorescence. The binding assay was the same as described above except that the tertiary antibody was rhodamine-conjugated goat anti-Rabbit IgG. Cells were layered on a glass microscope slide to which a coverslip was added and then viewed with a fluorescent Olympus microscope. To induce internalization, cells were placed at time 0 in a 37° C. CO2 incubator for 1 hour prior to being layered on a microscope slide and viewed as described above.

Example 4: 337B7 Internalization

Figure 3A:
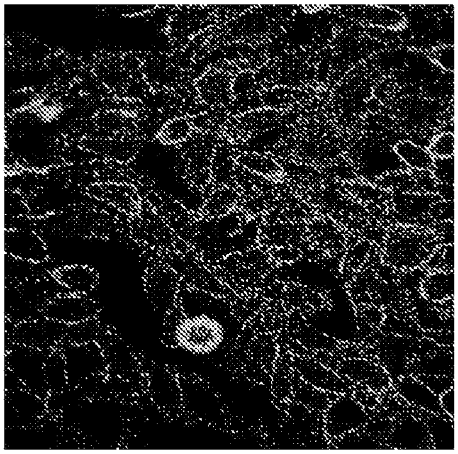
FIGS. 3A and 3B are photomicrographs that show PTGFRN positive cells displaying 33B7 binding and internalization.
Figure 3B:
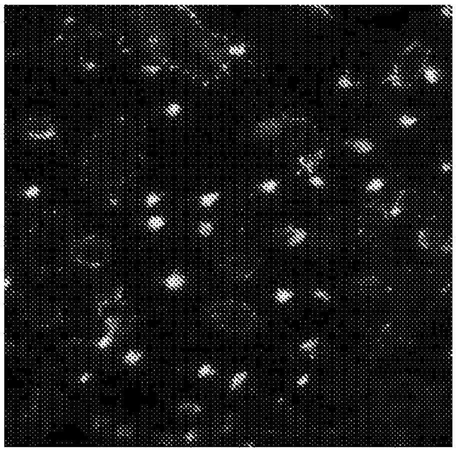

It was investigated whether the 33B7 antibody was internalizing the cell surface target PTGFRN. For this purpose, antibody binding to Hek-293 cells transfected with PTGFRN cDNA was carried out by incubating cells in suspension with 33B7 followed by FITC-conjugated secondary antibody for 1 hour at 4° C. Cells were then transferred to 37° C. for 1 hour and visualized under fluorescence microscope. Cells at 4° C. incubated with 33B7 displayed a strong cell surface immunofluorescence indicating biding of 33B7 to the PTGFRN expressed on the cell surface as shown in FIG. 3A. Upon incubation at 37° C., all of the cell surface binding has disappeared and fluorescence is detected inside the cells (FIG. 3B) indicating that internalization has taken place and 33B7 is an internalizing antibody. At this point, it was also confirmed that 33B7 antibody was first-in-class as no other internalizing antibody to this CSP had been developed.

Example 5: Development of 33B7-ADC

Since 33B7 is an internalizing antibody, an exemplary 33B7-ADC was developed by conjugating 33B7 to Saporin, a generic cytotoxic drug, via a linker. Saporin, used in our studies, is routinely used as payload to conjugate in ADC for proof-of-concept and efficacy studies. Saporin is not cytotoxic unless it penetrates inside cells but has a very low permeability on its own and needs to be delivered as a payload by being conjugated to an internalizing antibody in order to enter and inhibit cell proliferation. This is similar to many effective drugs used in ADC development and the antibody is considered the main enabling component of the ADC. Saporin was chemically conjugated to 33B7 via a cleavable linker and achieved a drug antibody ratio (DAR) of approximately 2.

Example 6: 33B7-ADC Internalization

As an ADC proof-of concept, 33B7 was conjugated with saporin and tested against a panel of cancer cells expressing PTGFRN. Cells to be tested were plated in 96 well plates at a density varying from 2,000 to 5,000 cells per well in standard serum containing medium. After 24 hours, ADC at concentrations varying from 0.1 to 10 nM was added to the cells. After 72 hours, cells were collected to measure proliferation/viability using a commercially available chemiluminescent cell viability assay (Promega Corporation, Madison, WI).

Figure 4:
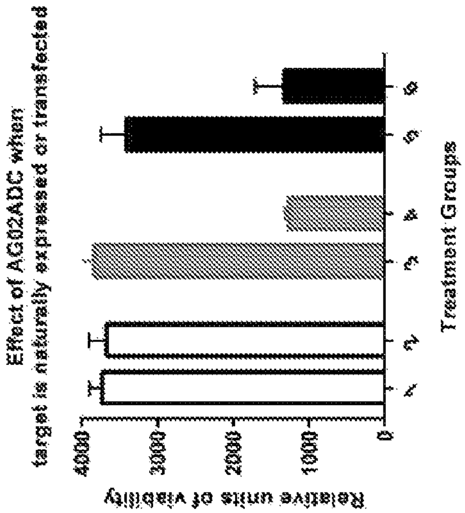
FIG. 4 is a bar graph showing the ability of the anti-PTGFRN antibody-drug conjugate (ADC) to inhibit the proliferation of cells (originally negative for PTGFRN) that had been transfected with empty mammalian expression vector pcDNA 3.1 (White Bars 1 and 2), or PTGFRN cDNA in pcDNA 3.1 (Gray Bars 3 and 4), or natural cancer cells positive for PTGFRN (Black Bars). Treatment Groups: 1 & 2 empty vector transfected into PTGFRN negative cancer cells; 3 & 4 PTGFRN-pcDNA 3.1 transfected into PTGFRN negative cells; 5 & 6 cancer cells that are PTGFRN positive; 1, 3 & 5 use non-immune mouse IgG+drug; 2, 4 & 6 use 33B7 IgG mAb+drug. 33B7-ADC kills 65% PTGFRN positive cells.

Our initial study focused on determining if the ADC was able to deliver the cytotoxic drug to PTGFRN positive cells and inhibit the proliferation of such cells. For this study (FIG. 4), we used cells that were negative for PTGFRN and these were either transfected with empty pcDN 3.1 vector (White Bars 1 and 2), or PTGFRN cDNA ligated to the mammalian expression vector pcDNA 3.1 (Gray Bars 3 and 4), or cancer cells naturally positive for PTGFRN (Black Bars 5 and 6). In bars 1, 3 and 5 we used a control IgG ADC conjugated to saporin at 10 nM, while bars 2, 4 and 6 treatments consisted of 33B7-ADC at 10 nM. As can be observed in FIG. 4, the 33B7-ADC inhibited a high percentage of PTGFRN positive cells (~65%) while it had no effect on PTGFRN negative cells. The control IgG did not deliver saporin inside the cell so produced no effect in any of the cells.

Example 7: Anti-Cancer Activity of 33B7-ADC

The ability of the 33B7-ADC to inhibit different cancers (FIG. 5) was investigated. Again, we used 33B7-ADC (red bar) as the test and an IgG ADC (blue bar) as control. FIG.

Figure 5:
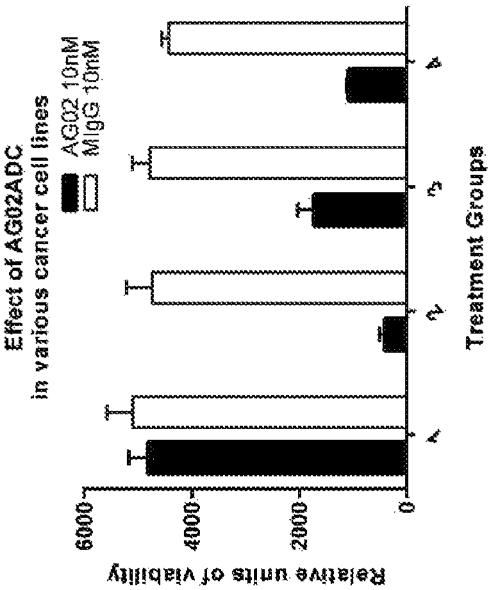
FIG. 5 is a bar graph showing the effect of 33B7-ADC in various cancer cell lines. (1) a PTGFRN negative control cell line, (2) a spindle sarcomatoid carcinoma cell line (SCSC), (3) a medulloblastoma carcinoma cell line, and (4) a mesothelioma cell line.

5 is a bar graph that depicts (1) a PTGFRN negative control cell line, (2) a hamster spindle carcinoma cell line, (3) a medulloblastoma carcinoma cell line, and (4) a mesothelioma cell line. Cell lines 2, 3 and 4 have all been shown to produce tumors when used as xenografts in nude mice. Additionally, we used free saporin at 10 nM in each cell line and demonstrated that free Saporin had no inhibitory effect in these cell lines (data not shown). As can be seen in FIG. 5, the control antibody ADC (mIgG-ADC) had no effect on any of the cell lines while the 33B7-ADC inhibited between 65% and 90% of the cells viability from the carcinoma cell lines while it did not inhibit any of the PTGFRN negative control cells.

Additional cell lines were tested as described above and the results of these studies are summarized in the following Table 1.

TABLE 1

Summary of 33B7 binding to cancer cell lines

| Cell Line | Cancer Type | 33B7 Binding (RFI) | ADC Killing |
|---|---|---|---|
| Hek-293 | Normal cells | Negative | No |
| MCF-7 | Breast | Weak | No |
| DAOY | Medulloblastoma | Strong | Yes |
| A431 | Epidermoid carci. (H&N) | Strong | Yes |
| MSTO211H | Mesothelioma | Medium | Yes |
| 143B | Osteosarcoma | Medium | Yes |
| SCSC | Spindle Cell Sarco. Carci. | Strong | Yes |
| JEG-3 | Choriocarcinoma | Medium-weak | Yes |
| CCL-136 | Rhabdomyosarcoma | Medium-weak | Yes |
| IMR-32 | neuroblastoma | Medium-weak | Yes |
| SK-LMS1 | Leiomyosarcoma | positive | Yes |
| Cell Line | Cancer Type | 33B7 Binding (RFI) | ADC Killing |
| MDA-MB-468 | Triple neg. breast carcinoma | positive | Yes |

The data with different cancer cell lines show that there are a variety of cancer cell types that bind 33B7 and are killed by 33B7-ADC. The ability to bind 33B7 is a good guide to determining the ability of the cells to respond to the ADC. Normal kidney epithelial cells Hek293 cells were negative for 33B7 binding and ADC mediated killing. ER+ breast cancer cells were weakly positive while medulloblastoma and SCSC cells were strongly positive. Except for SCSC all other cell lines are of human origin.

Example 8: 33B7 Binds to PTGFRN

Figure 6B:
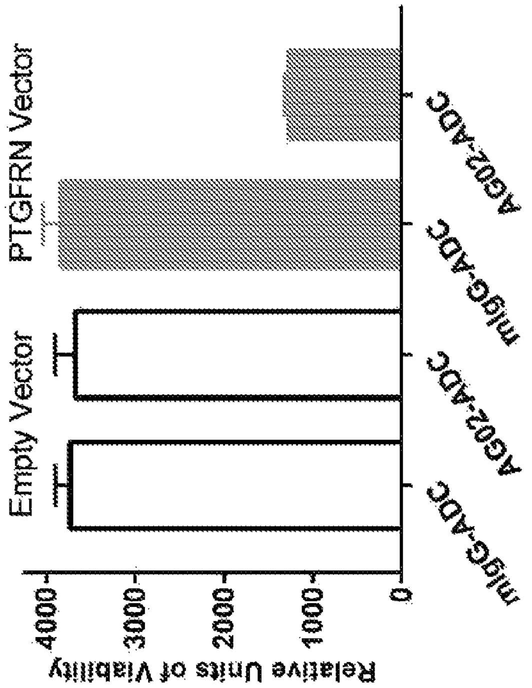
FIG. 6B is a bar graph showing the results of a 33B7-ADC inhibition assay on MCF-7 cells transfected with empty vector (EV) or with PTGFRN-pcDNA 3.1 (PTGFRN) treated with 33B7-ADC or with a non-immune IgG conjugated to saporin (mIg-ADC) as negative control.

As further evidence, breast cancer cells (MCF-7) that are mostly negative for 33B7 binding (see FIG. 2) do not respond to 33B7-ADC. However, when PTGFRN cDNA is transfected into MFC-7 cells, then the transfected cells can bind 33B7 (FIG. 6A) as well as respond to 33B7-ADC (FIG. 6B). Thus, binding of 33B7 to cells can be used to identify cells that will be responsive to 33B7-ADC.

Figure 6A:
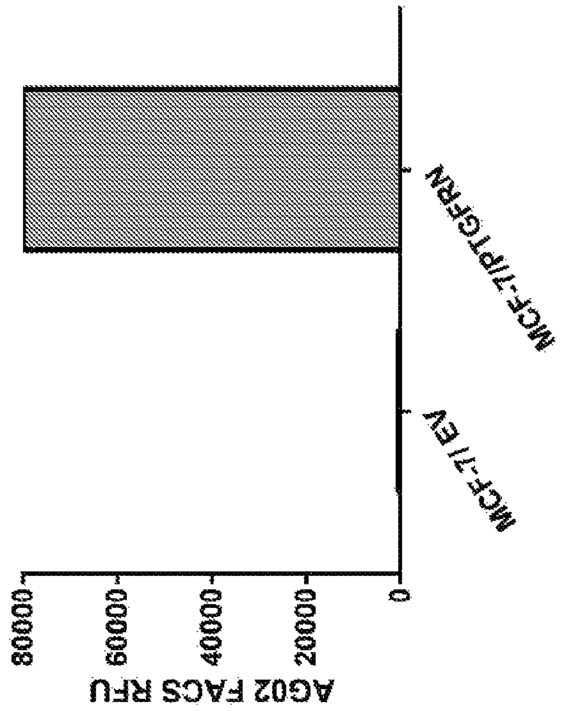
FIG. 6A is a bar graph showing flow based binding of 33B7 to empty vector (EV) and PTGFRN-pcDNA 3.1 transfected MCF-7 cells.

FIG. 6A is a bar graph showing the results of a flow based binding assay of 33B7 to empty vector (EV) and PTGFRN transfected MCF-7 cells. FIG. 6B is a bar graph showing the results of a 33B7-ADC inhibition assay on MCF-7 cells transfected with empty vector (EV) or with PTGFRN cDNA (PTGFRN) treated with 33B7-ADC or with mIg-ADC as negative control.

Example 9: Dose Response of 33B7-ADC

Figure 7:
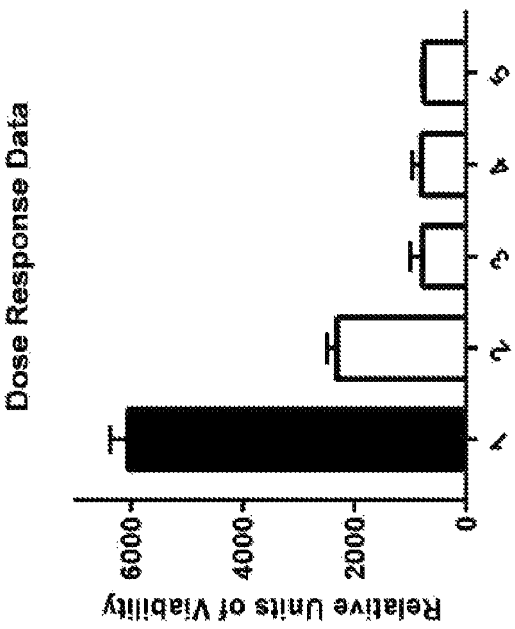
FIG. 7 is a bar graph showing dose response data for treatment of SCSC cells with increasing concentrations of 33B7-ADC.

We studied the effect of dose variation of 33B7-ADC to determine if there might be a dose dependent effect of 33B7-ADC. Using the spindle cell carcinoma cell line (SCSC) that express high level of 33B7 binding (FIG. 2), we treated the cells with (1) a control IgG ADC at 10 nM, and 33B7-ADC at (2) 0.1 nM (3) 1.0 nM (4) 3 nM and (5) 10 nM. As can be determined (FIG. 7), it appears there is a dose response effect of 33B7-ADC on cell viability. In most cells lines tested, 33B7-ADC was used at 10 nM.

The in vitro cell assays demonstrated that (1) 33B7 conjugated to saporin at 10 nM was able to inhibit cells expressing PTGFRN and binding 33B7 while it had no effect non-PTGFRN expressing cells nor on cells not binding 33B7, either natural or transfected, (2) 33B7-ADC is active over several cancers and (3) the effect on cells is dose dependent.

Example 10: In Vivo Tumor Inhibition Activity of 33B7-ADC

Having established the fact that 33B7-ADC is effective in PTGFRN positive cells using in vitro studies, we then investigated the effect of 33B7-ADC using in vivo mouse xenograft studies.

The following studies were established in our laboratory using well-documented protocols and proven methodology for establishing cancer xenografts in nude mice. All xenograft studies used female athymic nude mice injected subcutaneously (s.c.) with 5×106 of the cells under study. In all cases, the tumors were allowed to grow to ~100 $mm^3$ prior to mice being randomized into various experimental groups (6 mice/group). 33B7-ADC or vehicle control was administered i.v weekly at 10 μg/mouse (0.5 mg/kg). Tumor dimensions were measured to determine tumor volume in mm3 at each time point (Vt). Tumor volume increases at each time point were determined by Vt/Vo ratio with Vo being the tumor volume at time of randomization.

Figure 8:
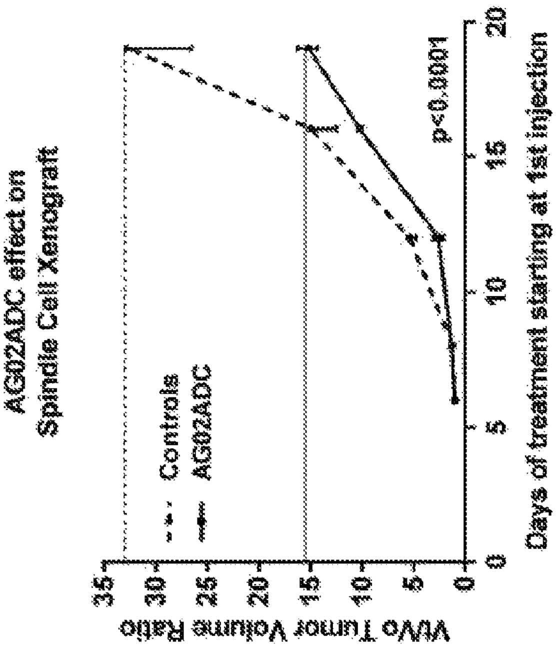
FIG. 8 is a line graph showing 33B7-ADC effect on the volume of tumors in a spindle cell carcinoma xenograft model.
Figure 9:
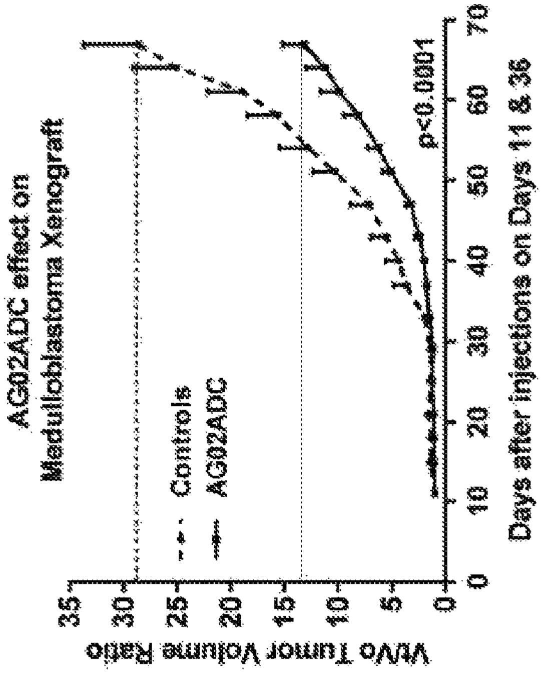
FIG. 9 is a line graph showing 33B7-ADC effect on the volume of tumors in a medulloblastoma xenograft model.
Figure 10:
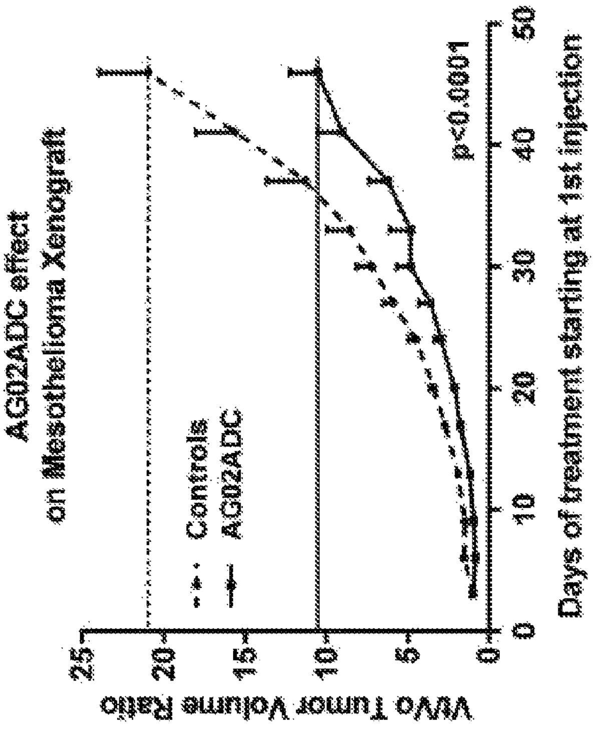
FIG. 10 is a line graph showing 33B7-ADC effect on the volume of tumors in a mesothelioma xenograft model.

The studies used the following xenografts (1) spindle cell carcinoma (FIG. 8); (2) medulloblastoma (FIG. 9); and (3) mesothelioma (FIG. 10). As observed from the graphs, in each case the 33B7-ADC showed a tumor growth inhibition of at least 50% compared with controls.

Example 11: Additional Investigation of Antibody Conjugates

We have injected >6 mice with 33B7-ADC (10 μg/mouse) once a week for 28 Days and compared them to mice injected with vehicle control. We did not observe any overt/gross signs of toxicity/signs of imminent morbidity or death/obvious discomfort, coat roughing, weight loss, reduction in food/water intake, eye condition etc., by daily monitoring of mice. This daily observation of mice in our studies is mandated under our Institutional Animal Care and Use Committee (LACUC) Certification. Post study necropsy showed no gross abnormalities or change in major organs in 33B7-ADC treated animals when compared with normal organs.

Using 33B7-ADC as a treatment in xenograft bearing nude mice, we demonstrated tumor growth inhibition >50% in all xenografts tested even though the 33B7ADC had not been optimized for dose or treatment schedule. While saporin is used in these studies and shows efficacy we fully expect more potent drugs to have considerably more efficacy. Examples of suitable cytotoxic reagents that may be conjugated to the antibodies of the disclosure include, but are not limited to, monomethyl auristatin E, monomethyl auristatin F, maytansinoid DM1, maytansinoid DM4, calicheamicin, ozogamicin, α-amanitin, yttrium-90, and iodine-131.

Example 12: 33B7 Antibody Sequences

The nucleotide and deduced amino acid sequences of the variable regions of the light chain and heavy chain of 33B7 were determined. mRNA from 33B7 hybridoma was obtained by Trizol® extraction. 1st strand cDNA synthesis was carried out by RT-PCR with Sensiscript® reverse transcriptase and universal primer sets. A commercial kit containing mouse IgG primer sets (EMD Millipore, Billerica, Mass.) was used to amplify light and heavy chains cDNA of 33B7 following manufacturer's instructions. PCR products were run on a 1% agarose gel electrophoresis followed by ethidium bromide staining. Bands corresponding to vH and vL were cut and extracted with Qiagen gel DNA extraction kit. vH DNA and vL DNA was topo cloned, plated onto LB Ampicillin plates and several clones were picked, grown and analyzed after EcoRI restriction enzyme digestion to verify presence of insert and size of band. 13 clones were sent for sequencing to obtain nucleotide sequences of vH and vL The nucleic acid sequence of the variable region of the light chain of 33B7 is

```
                                        (SEQ ID NO: 1)
GACATTGTGATGTCACAGTCTCCATCCTCCCTAGCTGTGTCAGTT

GGAGAGAAGGTTACTATGAGCTGCAAGTCCAGTCAGAGCCTTTTA

TATAGTACCAATCAAAAGAACTACTTAGCCTGGTACCAGCAGAAA

CCAGGGCAGTCTCCTAAACCGCTGATTTACTGGGCATCCACTAGG

GAATCTGGGGTCCCTGATCGCTTCACAGGCAGTGGGTCTGGGACA

GATTTCACTCTCACCATCAGCAGTGTGAAGGCTGAAGACCTGGCA

GTTTATTACTGTCAGCAATATTATAGTTATCGGACGTTCGGTGGA

GGCACCAAGCTGGAAATCAAA
```

The amino acid sequence of the variable region of the light chain of 33B7 is

```
                                        (SEQ ID NO: 2)
DIVMSQSPSSLAVSVGEKVTMSCKSSQSLLYSTNQKNYLAWYQQK

PGQSPKPLIYWASTRESGVPDRFTGSGSGTDFTLTISSVKAEDLA

VYYCQQYYSYRTFGGGTKLEIKRADAAPTVSIFPPSSKLG
```

The light chain variable region (vL) CDR1, CDR2, and CDR3 are double underlined. More specifically, the vL-CDR1, vL-CDR2, and vL-CDR3 sequences of 33B7 are set forth in SEQ ID NOs: 5, 6, and 7, respectively.

The nucleic acid sequence of the variable region of the heavy chain of 33B7 is

```
                                        (SEQ ID NO: 3)
GATGTACAGCTTCAGGAGTCAGGACCTGGCCTCGTGAAACCTTCT

CAGTCTCTGTCTCTGACCTGCTCTGTCACTGGCTGCTCCATCACC

AGTGGTTATTATTGGAACTGGATCCGGCAGTTTCCAGGAAACAAA

CTGGAATGGATGGGCTACATAAGCCACGATGGTAACAATAACTAC

AGCCCATCTCTCAAAAATCGAATCTCCATCACTCGTGACACATCT
```

-continued

```
AAGAACCAGTTTTTCCTGAAGTTGAACTCTGTGACTACTGAGGAC

ACAGCCACATATTACTGTGCAAGAGGATTTTATTACTACGGTTAC

TTTGGCTACTGGGGCCAAGGCACCACTCTCACAGTCTCCAGC
```

The amino acid of the variable region of the heavy chain of 33B7 is

```
                                        (SEQ ID NO: 4)
DVQLQESGPGLVKPSQSLSLTCSVTGCSITSGYYWNWIRQFPGNK

LEWMGYISHDGNNNYSPSLKNRISITRDTSKNQFFLKLNSVTTED

TATYYCARGFYYYGYFGYWGQGTTLTVSSAKTTPPSVYPLVPGSL
```

The heavy chain variable region (vH) CDR1, CDR2, and CDR3 are double underlined. More specifically, the vH-CDR1, vH-CDR2, and vH-CDR3 sequences of 33B7 are set forth in SEQ ID NOs: 8, 9, and 10, respectively.

```
vL-CDR1:
                          (SEQ ID NO: 5)
KSSQSLLYSTNQKNYLA

vL-CDR2:
                          (SEQ ID NO: 6)
WASTRES

vL-CDR3:
                          (SEQ ID NO: 7)
QQYYSYRT

vH-CDR1:
                          (SEQ ID NO: 8)
GCSITSGYYWN

vH-CDR2:
                          (SEQ ID NO: 9)
YISHDGNNNYSPSLKN

vH-CDR3:
                         (SEQ ID NO: 10)
GFYYYGYFGY
```

Example 13: Development of Anti-Human PTGFRN Antibodies

Human PTGFRN-ECD (extracellular domain; amino-acid 26 to amino-acid Y at 832) was synthesized and cloned into pcDNA 3.1 expression vector as a His-tag protein and transiently expressed in Hek-293 cells and purified by Nickel column. Protein was prepared with adjuvant and used as antigen to immunize mice. Hek-293 cells overexpressing PTGFRN by transfection of PTGFRN cDNA in pcDNA 3.1, designated "Hek-293 PTG clone 3", were used for screening. Negative cells are Hek-293 cells.

After checking the titer of the mouse serum by flow binding assay between PTGFRN positive and negative cells, the B cells collected from lymph node and spleen were fused by myeloma HL-1 cells. Hybridomas were directly selected by single cloning into methocel. Clones were picked and transferred into 96-well plates. Hybridoma clones were screened first by binding to Hek-293 PTG clone 3 cells and not to Hek293 cells using a flow binding assay protocol provided below.

In brief, detach cells with 5 mM EDTA-PBS and resuspend in 1% FBS in DMEM. Next, plate cells at 4×105 cells/100 μl/well into 96-well V-bottom plates. Add the 1st Ab mIgG or purified anti-H-PTGFRN 100 μl/well. Incubate at 4° C. for 1 hour. The final concentration for the first Ab can vary from 0.1, 1, 2, 5, 10, 20, to 40 μg/ml. Prepare 2nd Ab Alexa488-G anti-M IgG (Invitrogen Cat #A11029) at 10 μg/ml. Spin down cells and wash once with 1×PBS 200 μl/well. Add 2nd Ab at 100 μl/well. Incubate at 4° C. for 1 hour. Wash twice with cold PBS 200 μl/well. Resuspend cells with 100 μl/well and perform FACS analysis. Read with IntelliCytR flow reader. This assay was used for initial and confirmatory hybridoma selection.

Figure 11A:
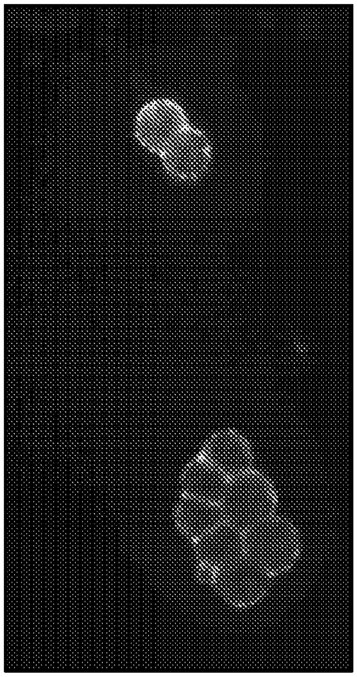
FIG. 11A and FIG. 11B are immunofluorescence assay results demonstrating the cell surface binding of 4F4 on the surface of PTGFRN positive cells at 4° C.
Figure 11B:
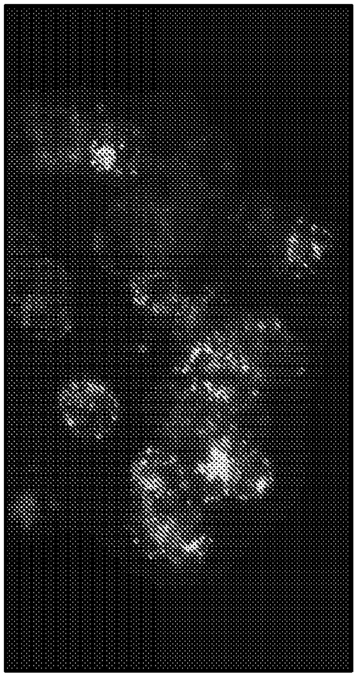
Figure 12A:
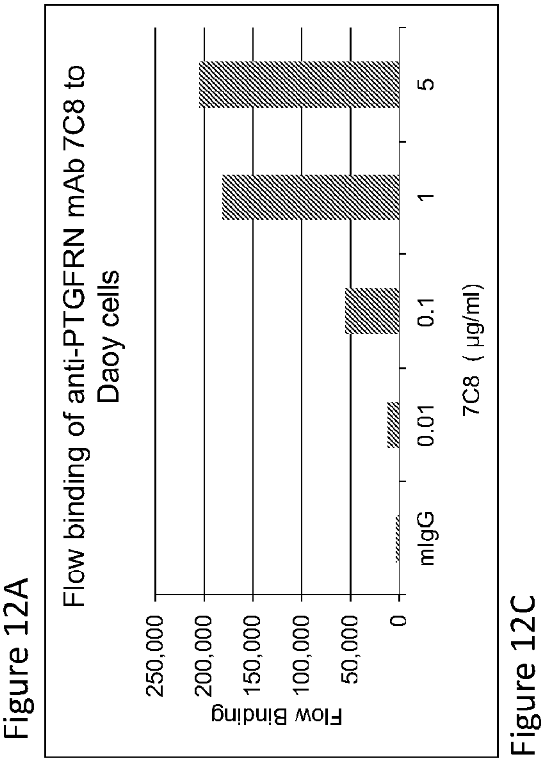
FIGS. 12A-12D show the binding of anti-PTGFRN monoclonal antibodies (mAbs) to various cell lines by Flow binding assay.
Figure 12B:
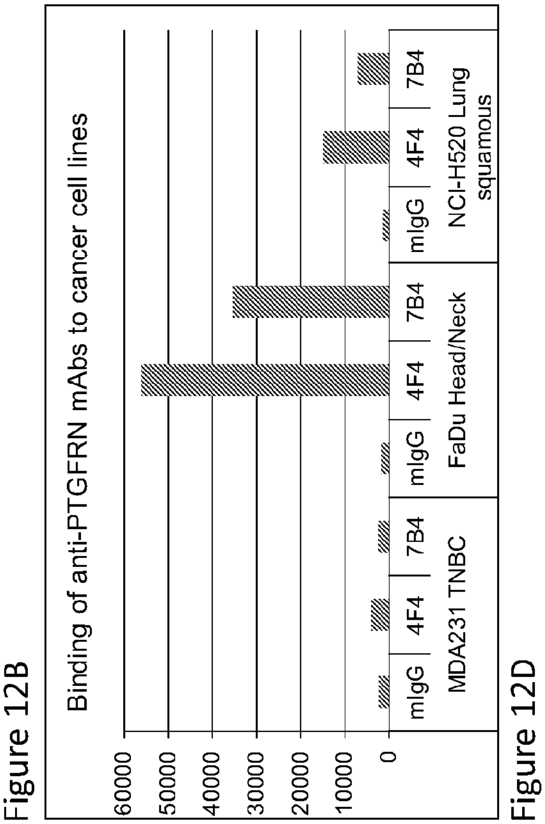
Figure 12C:
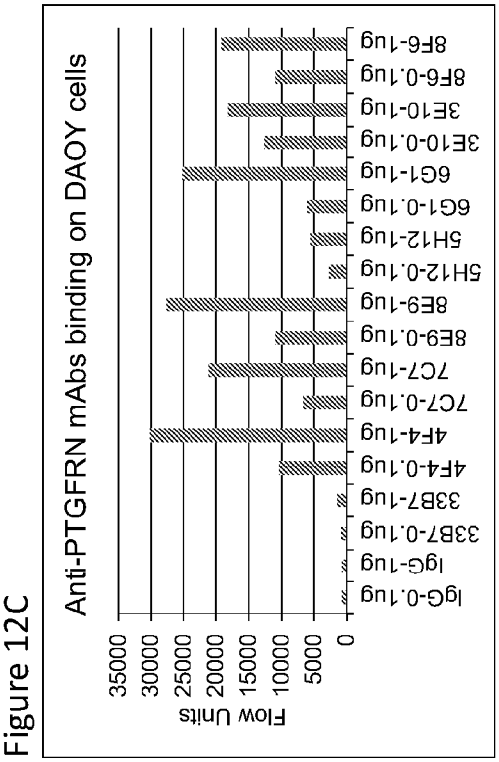
Figure 12D:
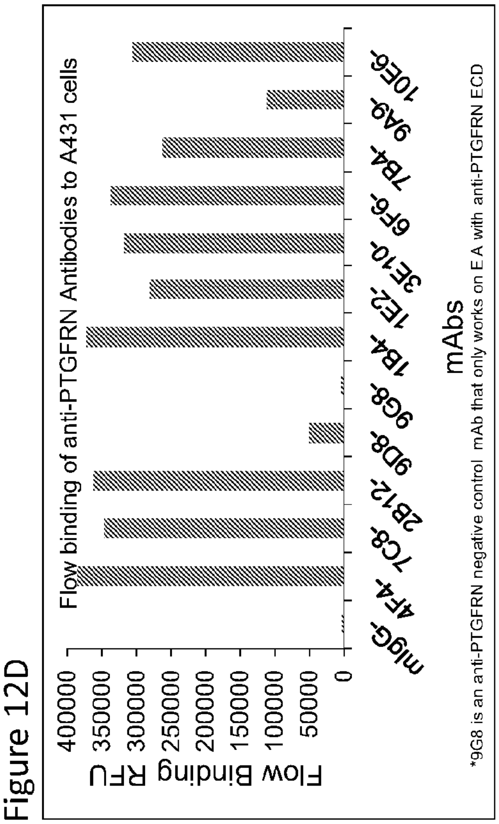

Clones were picked from 96-well plates and passed onto 48-well plates. Supernatants were assayed for confirmatory screen with the same flow binding screening assay as the one used for the initial screening. All positive clones by confirmatory screen were expanded, cryopreserved, and cultured for follow-on screening.

test are mixed with FAB-ZAP® consisting of FAB fragment of goat anti-mouse antibody that is conjugated to saporin of a cytoxic compound that is cell impermeable on its own and is only cytotoxic when inside the cells. If the antibody is internalized, FAB-ZAP® gets inside the cells and saporin exerts its cytotoxic effect. Exemplary immunofluorescence images showing the internalization of cell surface binding of 4F4 on the surface of PTGFRN positive cells at 4° C. and internalization at 37° C. are shown in FIG. 11A and FIG. 11B, respectively.

Interestingly, 17 antibodies are specific for PTGFRN and internalize but do not compete with 33B7, suggesting that more than one epitope on PTGFRN may be useful as a therapeutic, diagnostic, or imaging target. A summary of the screening results is provided in Table 2 below.

TABLE 2

| Summary of Screening | | | | | |
|---|---|---|---|---|---|
| Clones Screened 1,000 | | | | | |
| Flow assay positive for HEK-293-PTGFRN+ and negative for HEK-293 113 of 1,000 | | | | | |
| Confirmatory Screen Positive 91 of 113 | | | | | |
| Cell Surface Binding and Internationalization positivie 75 of 91 | | | | | |
| Kill >50% Daoy Cells | | Competition assay vs 33B7 HEK-PTGFRN 34 of 75 | | | |
| 44 of 75 | | Kill >50% Daoy Cells 17 of 54 | | Don't Compete 17 of 54 | |
| IgG1 | IgG2 | IgG1 | IgG2 | IgG1 | IgG2 |
| 32 of 44 | 12 of 44 | 8 of 17 | 9 of 17 | 13 of 17 | 4 of 17 |
| 9C* 12 NC* | 8C 4NC | | | | |

*NC non-competing with 33B7 by binding competition assay.
*C: copmpeting with 33B7 in the binding competition assay.

Clones picked were then expanded, cryopreserved and, further selected by internalization assay using fluorescent dye followed by killing assay by indirect ADC using FAB-ZAP®. Both assays were done with the Hek293 PTG clone 3 cell line.

Selected hybridomas were expanded and cryopreserved and antibodies were purified for further analyses on natural cell lines, as provided in the following Examples.

Example 14: Development of Stable Hek293 Cell Lines Overexpressing Human PTGFRN for Screening Approximately 1000 hybridoma clones were screened using Flow analysis. Ninety-one hydridomas (or antibodies) binding to PTGFRN positive cells were identified, termed as Cell Surface Binding (CSB) clones. Internalizing CSB positive clones (CSB-INT) were identified using Flow based internalization screening.

Briefly, the internalization assay uses pHAb Dye from Promega (Madison, WI) following the instruction manual. pHAb sensor dye has a low fluorescence at pH7 and a dramatic increase in fluorescence as the pH becomes acidic if the antibody is internalizing. pHAb dye is designed to label antibody by amine type conjugation. Using this assay, 75 hybridomas secreting internalizing anti-PTGFRN antibodies were selected.

Antibodies shown to internalize by the pHAb dye assay were then tested for their ability to kill PTGFRN positive cells by an indirect ADC assay where primary antibodies to The amino acid sequences for the heavy chain and light chain variable region CDRs (VH-CDR and VL-CDR) of the exemplary antibodies are provided in Table 3.

TABLE 3

Amino Acid Sequences of VH AND VL CDRs

| Hybridoma (antibody) | | Sequence ID | CDR1 | CDR2 | CDR3 |
|---|---|---|---|---|---|
| 4F4 | VH | HB/HE | GYTFTGY (SEQ ID NO: 11) | LPGSGS (SEQ ID NO: 12) | RRRSYYFDY (SEQ ID NO: 13) |
| | | HC | GYTFTTY (SEQ ID NO: 14) | NTYSGV (SEQ ID NO: 15) | GTGFYAMDC (SEQ ID NO: 16) |
| | VL | LE | RASGNIHNYLA (SEQ ID NO: 17) | NAKTLAD (SEQ ID NO: 18) | QHFWSTPYT (SEQ ID NO: 19) |
| | | LF | SASQGISNYLN (SEQ ID NO: 20) | YTSSLHS (SEQ ID NO: 21) | QQYSKLPWT (SEQ ID NO: 22) |
| | | LG | RSSQSLVHINGNTYLH (SEQ ID NO: 23) | KVSNRFS (SEQ ID NO: 24) | SQSTHVPWT (SEQ ID NO: 25) |

TABLE 3-continued

Amino Acid Sequences of VH AND VL CDRs

| Hybridoma (antibody) | | Sequence ID | CDR1 | CDR2 | CDR3 |
|---|---|---|---|---|---|
| 1B4 | VH | HB | DYTFTSY (SEQ ID NO: 26) | YPRSGN (SEQ ID NO: 27) | GTSITTVVERLFFDY (SEQ ID NO: 28) |
| | | HF | GFTFSDA (SEQ ID NO: 29) | RNKANNHA (SEQ ID NO: 30) | GGYYPFDY (SEQ ID NO: 31) |
| | VL | | RASQSISDYLH (SEQ ID NO: 32) | YSSQSIS (SEQ ID NO: 33) | QNGHSFPYT (SEQ ID NO: 34) |
| 3E10 | VH | | GFTFSSY (SEQ ID NO: 35) | SSGGSH (SEQ ID NO: 36) | HPSYYGSSLYCFDY (SEQ ID NO: 37) |
| | VL | | RASQDISNYLN (SEQ ID NO: 38) | YTSRLHS (SEQ ID NO: 39) | QQGSTLPWT (SEQ ID NO: 40) |
| 6F6 | VH | | GYTFTTY (SEQ ID NO: 41) | HPSDSD (SEQ ID NO: 42) | SLYYTMDY (SEQ ID NO: 43) |
| | VL | | KASQDIKKYIA (SEQ ID NO: 44) | YTSTLQP (SEQ ID NO: 45) | LQYDNLLYT (SEQ ID NO: 46) |
| 9B11 | VH | HB | DYTFTSY (SEQ ID NO: 47) | YPRSGN (SEQ ID NO: 48) | GTSITTVVERLFFDY (SEQ ID NO: 49) |
| | | HE | GYTFTTY (SEQ ID NO: 50) | YPRDGN (SEQ ID NO: 51) | DYYGSTYGYFDY (SEQ ID NO: 52) |
| | VL | LE | RASEKIYSYLA (SEQ ID NO: 53) | DANTLAQ (SEQ ID NO: 54) | QHHYVTPLT (SEQ ID NO: 55) |
| | | LF | RASQSISDYLH (SEQ ID NO: 56) | YSSQSIS (SEQ ID NO: 57) | QNGHSFPYT (SEQ ID NO: 58) |
| 10D9 | VH | | GCSITSGY (SEQ ID NO: 59) | NYDGN (SEQ ID NO: 60) | SDGYYWYFDV (SEQ ID NO: 61) |
| | VL | | KASQDIKSYLS (SEQ ID NO: 62) | YATSLAD (SEQ ID NO: 63) | LQHAERPLT (SEQ ID NO: 64) |
| 2B12 | VH | | GYTFTSY (SEQ ID NO: 65) | YPGSGN (SEQ ID NO: 66) | FFILTSYYFDY (SEQ ID NO: 67) |
| | VL | | KASQNVGTAVA (SEQ ID NO: 68) | LASNRYT (SEQ ID NO: 69) | QQYSNYPLT (SEQ ID NO: 70) |

TABLE 3-continued

Amino Acid Sequences of VH AND VL CDRs

| Hybridoma (antibody) | | Sequence ID | CDR1 | CDR2 | CDR3 |
|---|---|---|---|---|---|
| 7C8 | VH | | GYTFTSY (SEQ ID NO: 71) | NPNNGG (SEQ ID NO: 72) | GDY (SEQ ID NO: 73) |
| | VL | LF | SASQGIHNYLN (SEQ ID NO: 74) | YTSGLHS (SEQ ID NO: 75) | QQYSKLPWT (SEQ ID NO: 76) |
| | | LG | RSSQSLENSDGNTYLN (SEQ ID NO: 77) | RVSNRES (SEQ ID NO: 78) | LQVTHVPYT (SEQ ID NO: 79) |
| 9A9 | VH | | GYTFTTY (SEQ ID NO: 80) | YPRDGN (SEQ ID NO: 81) | DYYGSTYGYFDY (SEQ ID NO: 82) |
| | VL | | RASEKIYSYLA (SEQ ID NO: 83) | DANTLAQ (SEQ ID NO: 84) | QHHYVTPLT (SEQ ID NO: 85) |
| 1E2 | VH | | DYSITSGY (SEQ ID NO: 86) | SYDGS (SEQ ID NO: 87) | GWDYCFDY (SEQ ID NO: 88) |
| | VL | | SASQGISNYLN (SEQ ID NO: 89) | YTSGLHS (SEQ ID NO: 90) | QQYSQLPWT (SEQ ID NO: 91) |
| 10E6 | VH | | GFSLTSY (SEQ ID NO: 92) | WGDGS (SEQ ID NO: 93) | YGNYYYAMDY (SEQ ID NO: 94) |
| | VL | LD | KASQDINSYLS (SEQ ID NO: 95) | RANRLVD (SEQ ID NO: 96) | LQYDEFPYT (SEQ ID NO: 97) |
| | | LE | RASEKIYSYLA (SEQ ID NO: 98) | NAKTLAE (SEQ ID NO: 99) | QHHYVTPLT (SEQ ID NO: 100) |

The amino acid sequences for the heavy chain and light chain and variable regions (VH and VL, respectively) of the exemplary antibodies are provided in Table 4. The CDR sequences are in bold and highlighted in gray.

TABLE 4

| VH/VL amino acid sequences | | | |
|---|---|---|---|
| Hybridoma (antibody) | | Sequence ID | Sequence (SEQ ID NO) |
| 4F4 | VH | HB/HE | QVQLQQSGAELMKPGASVKLSCKATGYTFTGYWIEWVKQRPGHGLEWI GEILPGSGSTNYNENFKGKATFTADTSSNTAYMQLSSLTTEDSAIYYCSR RRSYYFDYWGQGTTLTVSS (SEQ ID NO: 101) |
| | | HC | QIQLVQSGPELKKPGETVKISCKASGYTFTTYGMSWVKQAPGKGLKWM GWINTYSGVPTYTDDFKGRSVFSVETSASTAYLQINNLKYEDTATYFCVR GTGFYAMDCWGQGTSVTVSS (SEQ ID NO: 102) |
| | VL | LE | DIQMTQSPASLSASVGETVTITCRASGNIHNYLAWYQQKQGKSPQLLVYN AKTLADGVPSRFSGSGSGTQYSLKINSLQPEDFGSYYCQHFWSTPYTFGG GTKLEIK (SEQ ID NO: 103) |
| | | LF | DIQMTQTTSSLSASLGDRVTISCSASQGISNYLNWYQQKPDGTVKLLIYYT SSLHSGVPSRFSGSGSGTDYSLTISNLEPEDIATYYCQQYSKLPWTFGGG TKLEIK (SEQ ID NO: 104) |
| | | LG | DVVMTQTPLSLPVSLGDQASISCRSSQSLVHINGNTYLHWYLQKPGQSPN LLIYKVSNRFSGVPDRFSGSGSGTDFTLKISRVEAEDLGVYFCSQSTHVPW TFGGGTKLEIK (SEQ ID NO: 105) |
| 1B4 | VH | HB | QVQLQQSGTELARPGASVKLSCKASDYTFTSYGINWVKQRTGQGLEWIG EIYPRSGNTYYNENFKGKATLTADKSSSTAYMELRSLTSEDSAVYFCARGT SITTVVERLFFDYWGQGTTLTVSS (SEQ ID NO: 106) |
| | | HF | EVKLEESGGGLVQPGGSMKLSCAASGFTFSDAWMDWVRQSPEKGLEWV AEIRNKANNHATYYAESVKGRFTISRDDSKSSVYLQMNSLRAEDTGIYYCT RGGYYPFDYWGQGTTLTVSS (SEQ ID NO: 107) |
| | VL | | DIVMTQSPATLSVTPGDRVSLSCRASQSISDYLHWYQQKSHESPRLLIKYS SQSISGIPSRFSGSGSGSDFTLSINSVEPEDVGVYYCQNGHSFPYTFGGG TKLEIK (SEQ ID NO: 108) |
| 3E10 | VH | | EVHLVESGGDLVKPGGSLKLSCAASGFTFSSYGMSWVRQTPDKRLEWVA SISSGGSHTYYPDRVKGRFTISRDNAKNTLYLQMSSLKSEDTAMYYCARH PSYYGSSLYCFDYWGQGTTLTVSS (SEQ ID NO: 109) |
| | VL | | DIQMTQTTSSLSASLGDRVTISCRASQDISNYLNWYQQKPDGTVKLLIYYT SRLHSGVPSRFSGSGSGTDFSLTISNLEQEDVATYFCQQGSTLPWTFGGG TKLEIK (SEQ ID NO: 110) |
| 6F6 | VH | | QVQLQQSGAELVKPGASVKVSCKASGYTFTTYWMHWVKQRPGQGLEWI GRIHPSDSDTNYNQKFKGKATLTLDKSSSTAYMQLSSLTSEDSAVYYCAM SLYYTMDYWGQGTSVTVSS (SEQ ID NO: 111) |
| | VL | | DIQMTQSPSSLSASLGGKVTITCKASQDIKKYIAWYQHKPGKGPRLLIHYTS TLQPGIPSRFSGSGSGRDYSFSISNLEPEDIATYYCLQYDNLLYTFGGGTKL EIK (SEQ ID NO: 112) |
| 9B11 | VH | HB | QVQLQQSGTELARPGASVKLSCKASDYTFTSYGINWVKKRTGQGLEWIGE IYPRSGNTYHNENFKGQATLTADKSSSTAYMELRSLTSEDSAVYFCARGT SITTVVERLFFDYWGQGTTLTVSS (SEQ ID NO: 113) |
| | | HE | QVQLQQSGTELARPGASVKLSCKASDYTFTSYGINWVKKRTGQGLEWIG EIYPRSGNTYHNENFKGQATLTADKSSSTAYMELRSLTSEDSAVYFCARG TSITTVVERLFFDYWGQGTTLTVSS (SEQ ID NO: 114) |
| | VL | LE | DIQMTQSPASLSASVGGTVTITCRASEKIYSYLAWYQQKQGKSPQLLVYDA NTLAQGVPSRFSGSGSGTQFSLKINSLQPEDFGSYYCQHHYVTPLTFGAG TKLALK (SEQ ID NO: 115) |
| | | LF | DIVMTQSPATLSVTPGDRVSLSCRASQSISDYLHWYQQKSHESPRLLIKYS SQSISGIPSRFSGSGSGSDFTLSINSVEPEDVGVYYCQNGHSFPYTFGGG TKLEIK (SEQ ID NO: 116) |
| 10D9 | VH | | DVQLQESGPGLVKPSQSLSLTCSVTGCSITSGYDWNWIRQFPGNKLEWM GYINYDGNSNYIPSLKNRVSITRDTSKNQFFLKLNSVTTEDTATYYCARSD GYYWYFDVWGTGTTVTVSS (SEQ ID NO: 117) |
| | VL | | DIKMTQSPSSMYASLGERVTITCKASQDIKSYLSWYQQKPWKSPKTLIYYA TSLADGVPSRFSASGSGQDYSLTISSLESDDTATYYCLQHAERPLTFGAGT KLELK (SEQ ID NO: 118) |
| 2B12 | VH | | QVQLQQPGAELVKPGASVKMSCKASGYTFTSYWITWVKQGPGQGLEWIG DIYPGSGNTNYNEKFKSKATLTVDTSSSTAYMQLSSLTSEDSAVYYCARFF ILTSYYFDYWGQGTTLTVSS (SEQ ID NO: 119) |
| | VL | | GIVMTQSQKFMSTTVGDRVSITCKASQNVGTAVAWFQQKPGQSPKLLIY LASNRYTGVPDRFTGSGSGTDFTLTISNMQSEDLADYFCQQYSNYPLTF GAGTKLELK (SEQ ID NO: 120) |
| 7C8 | VH | | QVQLQQPGTELVKPGASVKLSCKASGYTFTSYLMHWVKQRPGQGLEWI GNINPNNGGTNYNDKFKSKATLTVDKSSITAYMQLSSLTSEDSAVYYCAR GDYWGQGTTLTVSS (SEQ ID NO: 121) |
| | VL | LF | DIQMTQTTSSLSASLGDRVTISCSASQGIHNYLNWYQQKPDGTVKLLIYY TSGLHSGVPSRFSGSGSGTDYSLTISNLEPEDIATYFCQQYSKLPWTFG GGTKLEIK (SEQ ID NO: 122) |

TABLE 4-continued

| VH/VL amino acid sequences | | | |
|---|---|---|---|
| Hybridoma (antibody) | | Sequence ID | Sequence (SEQ ID NO) |
| | | LG | DAVLTQTPLSLAVSLGDQASISCRSSQSLENSDGNTYLNWYLQKPGQSP QLLIYRVSNRFSGGLDRFSGSGSGTDFTLKISRVEAEDLGVYFCLQVTHV PYTFGGGTKLEIK (SEQ ID NO: 123) |
| 9A9 | VH | | QVQLQQSGPELVKPGASVKLSCKASGYTFTTYDINWVKQRPGQGLEWI GWLYPRDGNTNYNEKFKGKASLTVDTSSSTAYMELHSLTSEDSAVYFCA RDYYGSTYGYFDYWGQGTTLTVSS (SEQ ID NO: 124) |
| | VL | | DIQMTQSPASLSASVGGTVTITCRASEKIYSYLAWYQQKQGKSPQLLVYD ANTLAQGVPSRFSGSGSGTQFSLKINSLQPEDFGSYYCQHHYVTPLTFG AGTKLALK (SEQ ID NO: 125) |
| 1E2 | VH | | DVQLQESGPGLVKPSQSLSLTCSVTDYSITSGYYWNWIRQFPGNKLEW MGYISYDGSNNYNPSLKNRLSITRDTSKNQFFLKLNSVTPEDTATYYCAR GWDYCFDYWGQGATLTVSS(SEQ ID NO: 126) |
| | VL | | DIQMTQTTSSLSASLGDRVTISCSASQGISNYLNWYQQKPDGTVKLLIYY TSGLHSGVPSRFSGSGSGTDYSLTISNLEPEDIATYYCQQYSQLPWTFG GGTKLEIK (SEQ ID NO: 127) |
| 10E6 | VH | | QVQLKESGPGLVAPSQSLSITCTVSGFSLTSYGVSWVRQPPGKGLEWL GVIWGDGSTNYHSALISRLSISKDNSKSQVFLKLNSLQTDDTATYYCAEY GNYYYAMDYWGQGTSVTVSS(SEQ ID NO: 128) |
| | VL | LD | DIKMTQSPSSMYASLGERVTITCKASQDINSYLSWFQQKPGKSPKTLIYR ANRLVDGVPSRFSGSGSGQDYSLTISSLEYEDMGIYYCLQYDEFPYTFG GGTKQEIK (SEQ ID NO: 129) |
| | | LE | DIQMTQSPASLSASVGETVTITCRASEKIYSYLAWYQQKQGKSPQLLVYN AKTLAEGVPSRFSGSGSGTQFSLKINSLQPEDFGSYYCQHHYVTPLTFG AGTKLELK (SEQ ID NO: 130) |

The cDNA sequences for the VH/VL of the exemplary antibodies are provided in Table 5.

TABLE 5

| VH/VL cDNA sequences | | | |
|---|---|---|---|
| Hybridoma (antibody) | | Sequence ID | Sequence (SEQ ID NO) |
| 4F4 | VH | HB/HE | CAGGTTCAGCTGCAGCAGTCTGGAGCTGAGCTGATGAAGCCTGGGGC CTCAGTGAAGCTTTCCTGCAAGGCTACTGGCTACACATTCACTGGCT ACTGGATAGAGTGGGTAAAGCAGAGGCCTGGACATGGCCTTGAGTGG ATTGGAGAGATTTTACCTGGAAGTGGTAGTACTAACTACAATGAGAA CTTCAAGGGCAAGGCCACATTCACTGCAGATACATCCTCCAACACAG CCTACATGCAACTCAGCAGCCTGACAACTGAGGACTCTGCCATCTAT TACTGTTCAAGAAGGAGATCTTACTACTTTGACTACTGGGGCCAAGG CACCACTCTCACAGTCTCCTCA (SEQ ID NO: 131) |
| | | HC | CAGATCCAGTTGGTACAGTCTGGGCCTGAGCTGAAGAAGCCTGGAGA GACAGTCAAGATCTCCTGCAAGGCTTCTGGGTATACCTTCACAACCT ATGGAATGAGCTGGGTGAAACAGGCTCCAGGAAAGGGTTTAAAGTGG ATGGGCTGGATAAACACCTACTCTGGAGTGCCAACATATACTGATGA CTTCAAGGGACGGTCTGTCTTCTCTGTGGAAACCTCTGCCAGCACTG CCTATTTGCAGATCAACAACCTCAAATATGAGGACACGGCTACATAT TTCTGTGTAAGAGGGACTGGGTTCTATGCTATGGACTGCTGGGGTCA AGGAACCTCAGTCACCGTCTCCTCA (SEQ ID NO: 132) |
| | VL | LE | GACATCCAGATGACTCAGTCTCCAGCCTCCCTATCTGCATCTGTGGG AGAAACTGTCACCATCACATGTCGAGCAAGTGGGAATATTCACAATT ATTTAGCATGGTATCAGCAGAAACAGGGAAAATCTCCTCAGCTCCTG GTCTATAATGCAAAAACCTTAGCAGATGGTGTGCCATCAAGGTTCAG TGGCAGTGGATCAGGAACACAATATTCTCTCAAGATCAACAGCCTGC AGCCTGAAGATTTTGGGAGTTATTACTGTCAACATTTTTGGAGTACT CCGTACACGTTCGGAGGGGGGACCAAACTGGAAATAAAA (SEQ ID NO: 133) |
| | | LF | GATATCCAGATGACACAGACTACATCCTCCCTGTCTGCCTCTCTGGG AGACAGAGTCACCATCAGTTGCAGTGCAAGTCAGGGCATTAGCAATT ATTTAAACTGGTATCAGCAGAAACCAGATGGAACTGTTAAACTCCTG ATCTATTACACATCAAGITTACACTCAGGAGTCCCATCAAGGTTCAG |

TABLE 5-continued

VH/VL cDNA sequences

| Hybridoma (antibody) | | Sequence ID | Sequence (SEQ ID NO) |
|---|---|---|---|
| | | | TGGCAGTGGGTCTGGGACAGATTATTCTCTCACCATCAGCAACCTGG AACCTGAAGATATTGCCACTTACTATTGTCAGCAGTATAGTAAGCTT CCGTGGACGTTCGGTGGAGGCACCAAGCTGGAAATCAAA (SEQ ID NO: 134) |
| | | LG | GATGTTGTGATGACCCAAACTCCACTCTCCCTGCCTGTCAGTCTTGG AGATCAAGCCTCCATCTCTTGCAGATCTAGTCAGAGCCTTGTACACA TTAATGGAAACACCTATTTACATTGGTACCTGCAGAAGCCAGGCCAG TCTCCAAACCTCCTGATCTACAAAGTTTCCAACCGATTTTCTGGGGT CCCAGACAGGTTCAGTGGCAGTGGATCAGGGACAGATTTCACACTCA AGATCAGCAGAGTGGAGGCTGAGGATCTGGGAGTTTATTTCTGCTCT CAAAGTACACATGTTCCGTGGACGTTCGGTGGAGGCACCAAGCTGGA AATCAAA (SEQ ID NO: 135) |
| 1B4 | VH | HB | CAGGTTCAGCTGCAGCAGTCTGGAACTGAGCTGGCGAGGCCTGGGGC TTCAGTGAAGCTGTCCTGCAAGGCTTCTGACTACACCTTCACAAGCT ATGGTATAAACTGGGTGAAGCAGAGAACTGGACAGGGCCTTGAGTGG ATTGGAGAGATTTATCCTAGAAGTGGTAATACTTACTACAATGAGAA CTTCAAGGGCAAGGCCACACTGACTGCAGACAAATCCTCCAGCACAG CGTACATGGAGCTCCGCAGCCTGACATCTGAGGACTCTGCGGTCTAT TTCTGTGCAAGAGGGACGTCTATTACTACGGTAGTAGAGAGACTCTT CTTTGACTACTGGGGCCAAGGCACCACTCTCACAGTCTCCTC (SEQ ID NO: 136) |
| | | HF | GAAGTGAAGCTTGAGGAGTCTGGAGGAGGCTTGGTGCAACCTGGAGG ATCCATGAAACTCTCTTGTGCTGCCTCTGGATTCACTTTTAGTGACG CCTGGATGGACTGGGTCCGCCAGTCTCCAGAGAAGGGGCTTGAGTGG GTTGCTGAAATTAGAAACAAAGCTAATAATCATGCAACATACTATGC TGAGTCTGTGAAAGGGAGGTTCACCATCTCAAGAGATGATTCCAAAA GTAGTGTCTACCTGCAAATGAACAGCTTAAGAGCTGAAGACACTGGC ATTTATTACTGTACCAGGGGTGGTTACTACCCTTTTGACTACTGGGG CCAAGGCACCACTCTCACAGTCTCCTCAC (SEQ ID NO: 137) |
| | VL | | GACATTGTGATGACTCAGTCTCCAGCCACCCTGTCTGTGACTCCAGG AGATAGAGTCTCTCTTTCCTGCAGGGCCAGCCAGAGTATTAGCGACT ACTTACACTGGTATCAACAAAAATCACATGAGTCTCCAAGGCTTCTC ATCAAATATTCTTCCCAATCCATCTCTGGGATCCCCTCCAGGTTCAG TGGCAGTGGATCAGGGTCAGATTTCACTCTCAGTATCAACAGTGTGG AACCTGAAGATGTTGGAGTGTATTACTGTCAAAATGGTCACAGCTTT CCGTACACGTTCGGAGGGGGGACCAAGCTGGAAATAAAA (SEQ ID NO: 138) |
| 3E10 | VH | | GAGGTGCACCTGGTGGAGTCTGGGGGAGACTTAGTGAAGCCTGGAGG GTCCCTGAAACTCTCCTGTGCAGCCTCTGGATTCACTTTCAGCAGCT ATGGCATGTCTTGGGTTCGCCAGACTCCAGACAAGAGGCTGGAGTGG GTCGCAAGTATTAGTAGTGGTGGTAGTCACACTTACTATCCAGACAG GGTGAAGGGGCGATTCACCATCTCCAGAGACAATGCCAAGAACACCC TGTACCTGCAAATGAGCAGTCTGAAGTCTGAGGACACAGCCATGTAT TACTGTGCAAGACACCCGAGTTACTACGGTAGTAGCCTGTACTGCTT TGACTACTGGGGCCAAGGCACCACTCTCACAGTCTCCTCA (SEQ ID NO: 139) |
| | VL | | GATATCCAGATGACACAGACTACATCCTCCCTGTCTGCCTCTCTGGG AGACAGAGTCACCATCAGTTGCAGGGCAAGTCAGGACATTAGCAATT ATTTAAACTGGTATCAGCAGAAACCAGATGGAACTGTTAAACTCCTG ATCTACTACACATCAAGATTACACTCAGGAGTCCCATCAAGGTTCAG TGGCAGTGGGTCTGGAACAGATTTTTCTCTCACCATTAGCAACCTGG AGCAAGAAGATGTTGCCACTTACTTTTGCCAACAGGGCAGTACGCTT CCGTGGACGTTCGGTGGAGGCACCAAGCTGGAAATCAAA (SEQ ID NO:140) |
| 6F6 | VH | | CAGGTCCAACTGCAGCAGTCTGGGGCTGAACTGGTGAAGCCTGGGGC TTCAGTGAAGGTGTCCTGCAAGGCTTCTGGCTACACCTTCACCACCT ACTGGATGCACTGGGTGAAGCAGAGGCCTGGCCAAGGCCTTGAGTGG ATTGGAAGGATTCATCCTTCTGATAGTGATACTAACTACAATCAAAA GTTCAAGGGCAAGGCCACATTGACTTTAGACAAATCCTCCAGCACAG CCTACATGCAGCTCAGCAGCCTGACATCTGAGGACTCTGCGGTCTAT TACTGTGCAATGAGCCTTTACTATACTATGGACTACTGGGGTCAAGG AACCTCAGTCACCGTCTCCTCA (SEQ ID NO: 141) |
| | VL | | GACATCCAGATGACACAGTCTCCATCCTCACTGTCTGCATCTCTGGG AGGCAAAGTCACCATCACTTGCAAGGCAAGCCAAGACATTAAAAAGT ATATAGCTTGGTACCAACACAAGCCTGGAAAAGGTCCTAGGCTGCTC ATACATTACACATCTACATTACAGCCAGGCATCCCATCAAGGTTCAG TGGAAGTGGGTCTGGGAGAGATTATTCCTTCAGCATCAGCAACCTGG |

TABLE 5-continued

| VH/VL cDNA sequences | | | |
|---|---|---|---|
| Hybridoma (antibody) | | Sequence ID | Sequence (SEQ ID NO) |
| | | | AGCCTGAAGATATTGCAACTTATTATTGTCTACAGTATGATAATCTT CTGTACACGTTCGGAGGGGGGACCAAGCTGGAAATAAAA (SEQ ID NO: 142) |
| 9B11 | VH | HB | CAGGTTCAGCTGCAGCAGTCTGGAACTGAGCTGGCGAGGCCTGGGGC TTCAGTGAAGCTGTCCTGCAAGGCTTCTGACTACACCTTCACAAGCT ATGGTATAAACTGGGTGAAGAAGAGAACTGGACAGGGCCTTGAGTGG ATTGGAGAGATTTATCCTAGAAGTGGTAATACTTACCACAATGAGAA CTTCAAGGGCCAGGCCACACTGACTGCAGACAAATCCTCCAGCACAG CGTACATGGAGCTCCGCAGCCTGACATCTGAGGACTCTGCGGTCTAT TTCTGTGCAAGAGGGACGTCTATTACTACGGTAGTAGAGAGACTCTT CTTTGACTACTGGGGCCAAGGCACCACTCTCACAGTCTCCTCA (SEQ ID NO:143) |
| | | HE | CAGGTTCAGCTGCAGCAGTCTGGACCTGAACTGGTGAAGCCTGGGGC TTCAGTGAAGTTGTCCTGCAAGGCTTCTGGCTACACCTTCACAACCT ACGATATAAACTGGGTGAAGCAGAGGCCTGGACAGGGACTTGAGTGG ATTGGATGGCTTTATCCTAGAGATGGTAATACTAACTACAATGAGAA GTTCAAGGGCAAGGCCTCATTGACTGTAGACACATCCTCCAGCACAG CGTACATGGAGCTCCACAGCCTGACATCTGAGGACTCTGCGGTCTAT TTCTGTGCACGAGATTACTACGGTAGTACCTACGGGTACTTTGACTA CTGGGGCCAAGGCACCACTCTCACAGTCTCCTCA (SEQ ID NO: 144) |
| | VL | LE | GACATCCAGATGACTCAGTCTCCAGCCTCCCTATCTGCATCTGTGGG AGGAACTGTCACCATCACATGTCGAGCAAGTGAGAAGATTTACAGTT ATTTAGCATGGTATCAGCAGAAACAGGGAAAATCTCCTCAGCTCCTG GTCTATGATGCAAACACCTTAGCACAAGGTGTGCCATCAAGGTTCAG TGGCAGTGGATCAGGCACACAGTTTTCTCTGAAGATCAACAGCCTGC AGCCTGAAGATTTTGGGAGTTATTACTGTCAACATCATTATGTTACT CCGCTCACGTTCGGTGCTGGGACCAAGCTGGCGCTGAAA (SEQ ID NO: 145) |
| | | LF | GACATTGTGATGACTCAGTCTCCAGCCACCCTGTCTGTGACTCCAGG AGATAGAGTCTCTCTTTCCTGCAGGGCCAGCCAGAGTATTAGCGACT ACTTACACTGGTATCAACAAAAATCACATGAGTCTCCAAGGCTTCTC ATCAAATATTCTTCCCAATCCATCTCTGGGATCCCCTCCAGGTTCAG TGGCAGTGGATCAGGGTCAGATTTCACTCTCAGTATCAACAGTGTGG AACCTGAAGATGTTGGAGTGTATTACTGTCAAAATGGTCACAGCTTT CCGTACACGTTCGGAGGGGGGACCAAGCTGGAAATAAAAC (SEQ ID NO: 146) |
| 10D9 | VH | | GATGTACAGCTTCAGGAGTCAGGACCTGGCCTCGTGAAACCTTCTCA GTCTCTGTCTCTCACCTGCTCTGTCACTGGCTGCTCCATCACCAGTG GTTATGACTGGAACTGGATCCGGCAGTTTCCAGGAAACAAACTGGAA TGGATGGGCTACATAAACTACGATGGTAACAGTAACTACATCCCATC TCTCAAAAATCGAGTCTCCATCACTCGTGACACATCTAAGAACCAGT TTTTCCTGAAGTTGAATTCTGTGACTACTGAGGACACAGCCACATAT TACTGTGCAAGATCTGATGGTTACTACTGGTACTTCGATGTCTGGGG CACAGGGACCACGGTCACCGTCTCCTC (SEQ ID NO : 147) |
| | VL | | GACATCAAGATGACCCAGTCTCCATCCTCCATGTATGCATCGCTGGG AGAGAGAGTCACTATCACTTGCAAGGCGAGTCAGGACATTAAAAGCT ATTTAAGCTGGTACCAGCAGAAACCATGGAAATCTCCTAAGACCCTG ATCTATTATGCAACAAGCTTGGCAGATGGGGTCCCATCAAGATTCAG TGCCAGTGGATCTGGGCAAGATTATTCTCTAACCATCAGCAGCCTGG AGTCTGACGATACAGCAACTTATTACTGTCTACAGCATGCTGAGCGC CCTCTCACGTTCGGTGCTGGGACCAAGCTGGAGCTGAAA (SEQ ID NO: 148) |
| 2B12 | VH | | CAGGTCCAACTGCAGCAGCCTGGGGCTGAGCTTGTGAAGCCTGGGGC TTCAGTGAAGATGTCCTGCAAGGCTTCTGGCTACACCTTCACCAGCT ACTGGATAACCTGGGTGAAGCAGGGGCCTGGACAAGGCCTTGAGTGG ATTGGAGATATTTATCCTGGTAGTGGTAATACTAACTACAATGAGAA GTTCAAGAGCAAGGCCACACTGACTGTAGACACATCCTCCAGCACAG CCTACATGCAGCTCAGCAGCCTGACATCTGAGGACTCTGCGGTCTAT TACTGTGCAAGATTCTTCATACTGACCTCGTACTACTTTGACTACTG GGGCCAAGGCACCACTCTCACAGTCTCCTCA (SEQ ID NO: 149) |
| | VL | | GGCATTGTGATGACCCAGTCTCAAAAATTCATGTCCACAACAGTAGG AGACAGGGTCAGCATCACCTGCAAGGCCAGTCAGAATGTGGGTACTG CTGTAGCCTGGTTTCAACAGAAACCAGGACAATCTCCTAAACTACTG ATTTACTTAGCATCCAATCGGTACACTGGAGTCCCTGATCGCTTCAC AGGCAGTGGATCTGGGACAGATTTCACTCTCACCATTAGCAATATGC AGTCTGAAGACCTGGCAGATTATTTCTGTCAGCAATATAGCAACTAT |

TABLE 5-continued

VH/VL cDNA sequences

| Hybridoma (antibody) | Sequence ID | Sequence (SEQ ID NO) |
| --- | --- | --- |
| | | CCTCTCACGTTCGGTGCTGGGACCAAGCTGGAGCTGAAA (SEQ ID NO: 150) |
| 7C8 | VH | CAGGTCCAACTGCAGCAGCCTGGGACTGAACTGGTGAAGCCTGGGGC TTCAGTGAAGCTGTCCTGCAAGGCATCTGGCTACACCTTCACCAGCT ACCTGATGCACTGGGTGAAGCAGAGGCCTGGACAAGGCCTTGAGTGG ATTGGAAATATTAATCCTAACAATGGTGGTACTAACTACAATGATAA ATTCAAAAGCAAGGCCACACTGACTGTGGACAAATCCTCCATCACAG CCTACATGCAGCTCAGCAGCCTGACATCTGAGGACTCTGCGGTCTAT TATTGTGCAAGAGGGGACTACTGGGGCCAAGGCACCACTCTCACAGT CTCCTCA (SEQ ID NO: 151) |
| | VL LF | GATATCCAGATGACACAGACTACATCCTCCCTGTCTGCCTCTCTGGG AGACAGAGTCACCATCAGTTGCAGTGCAAGTCAGGGCATTCACAATT ATTTAAACTGGTATCAGCAGAAACCAGATGGAACTGTTAAACTCCTG ATCTATTACACATCAGGTTTACACTCAGGAGTCCCATCAAGGTTCAG TGGCAGTGGGTCTGGGACAGATTATTCTCTCACCATCAGCAACCTGG AACCTGAAGATATTGCCACTTACTTTTGTCAGCAGTATAGTAAGCTT CCGTGGACGTTCGGTGGAGGCACCAAGCTGGAAATCAAA (SEQ ID NO: 152) |
| | LG | GATGCTGTGCTGACCCAAACTCCACTCTCCCTGGCTGTCAGTCTTGG AGATCAAGCCTCCATCTCTTGTAGGTCTAGTCAGAGCCTTGAAAACA GTGATGGAAACACCTATTTGAACTGGTACCTCCAGAAACCAGGCCAG TCTCCACAGCTCCTGATCTACAGGGTTTCGAACCGATTTTCTGGGGG CCTAGACAGGTTCAGTGGTAGTGGATCAGGGACAGATTTCACACTGA AAATCAGCAGAGTGGAGGCTGAGGATTTGGGAGTTTATTTCTGCCTC CAAGTTACACATGTCCCGTACACGTTCGGAGGGGGGACCAAGCTG GAA (SEQ ID NO: 153) |
| 9A9 | VH | CAGGTTCAGCTGCAGCAGTCTGGACCTGAACTGGTGAAGCCTGGGGC TTCAGTGAAGTTGTCCTGCAAGGCTTCTGGCTACACCTTCACAACCT ACGATATAAACTGGGTGAAGCAGAGGCCTGGACAGGGACTTGAGTGG ATTGGATGGCTTTATCCTAGAGATGGTAATACTAACTACAATGAGAA GTTCAAGGGCAAGGCCTCATTGACTGTAGACACATCCTCCAGCACAG CGTACATGGAGCTCCACAGCCTGACATCTGAGGACTCTGCGGTCTAT TTCTGTGCACGAGATTACTACGGTAGTACCTACGGGTACTTTGACTA CTGGGGCCAAGGCACCACTCTCACAGTCTCCTCA (SEQ ID NO: 154) |
| | VL | GACATCCAGATGACTCAGTCTCCAGCCTCCCTATCTGCATCTGTGGG AGGAACTGTCACCATCACATGTCGAGCAAGTGAGAAGATTTACAGTT ATTTAGCATGGTATCAGCAGAAACAGGGAAAATCTCCTCAGCTCCTG GTCTATGATGCAAACACCTTAGCACAAGGTGTGCCATCAAGGTTCAG TGGCAGTGGATCAGGCACACAGTTTTCTCTGAAGATCAACAGCCTGC AGCCTGAAGATTTTGGGAGTTATTACTGTCAACATCATTATGTTACT CCGCTCACGTTCGGTGCTGGGACCAAGCTGGCGCTGAAA (SEQ ID NO: 155) |
| 1E2 | VH | GATGTACAGCTTCAGGAGTCAGGACCTGGCCTCGTGAAACCTTCTCA GTCTCTGTCTCTCACCTGCTCTGTCACTGACTACTCCATCACCAGTG GTTATTACTGGAACTGGATCCGGCAGTTTCCAGGAAACAAACTGGAA TGGATGGGCTACATAAGCTACGATGGTAGCAATAACTACAACCCATC TCTCAAAAATCGACTCTCCATCACTCGTGACACATCTAAGAACCAGT TTTTCCTGAAGTTGAATTCTGTGACTCCTGAGGACACAGCCACATAT TACTGTGCAAGAGGATGGGACTACTGCTTTGACTACTGGGGCCAAGG CGCCACTCTCACAGTCTCCTCA (SEQ ID NO: 156) |
| | VL | GATATCCAGATGACACAGACTACATCCTCCCTGTCTGCCTCTCTGGG AGACAGAGTCACCATCAGTTGCAGTGCAAGTCAGGGCATTAGCAATT ATTTAAACTGGTATCAGCAGAAACCAGATGGAACTGTTAAACTCCTG ATCTATTACACATCAGGTTTACACTCAGGAGTCCCATCAAGGTTCAG TGGCAGTGGGTCTGGGACAGATTATTCTCTCACCATCAGCAACCTGG AACCTGAAGATATTGCCACTTACTATTGTCAGCAGTATAGTCAACTT CCGTGGACGTTCGGTGGAGGCACCAAGCTGGAAATCAAA (SEQ ID NO: 157) |
| 10E6V | VH | CAGGTGCAGCTGAAGGAGTCAGGACCTGGCCTGGTGGCGCCCTCACA GAGCCTGTCCATCACATGCACTGTCTCAGGGTTCTCATTAACCAGCT ATGGTGTAAGCTGGGTTCGCCAGCCTCCAGGAAAGGGTCTGGAGTGG CTGGGAGTAATATGGGGTGACGGGAGCACAAATTATCATTCAGCTCT CATATCCAGACTGAGCATCAGCAAGGATAACTCCAAGAGCCAAGTTT TCTTAAAACTGAACAGTCTGCAAACTGATGACACAGCCACGTACTAC TGTGCCGAATATGGTAACTATTACTATGCTATGGACTACTGGGGTCA AGGAACCTCAGTCACCGTCTCCTCA (SEQ ID NO: 158) |

TABLE 5-continued

| VH/VL cDNA sequences | | |
|---|---|---|
| Hybridoma (antibody) | Sequence ID | Sequence (SEQ ID NO) |
| VL | LD | GACATCAAGATGACCCAGTCTCCATCTTCCATGTATGCATCTCTAGG AGAGAGAGTCACTATCACTTGCAAGGCGAGTCAGGACATTAATAGCT ATTTAAGCTGGTTCCAGCAGAAACCAGGGAAATCTCCTAAGACCCTG ATCTATCGTGCAAACAGATTGGTAGATGGGGTCCCATCAAGGTTCAG TGGCAGTGGATCTGGGCAAGATTATTCTCTCACCATCAGCAGCCTGG AGTATGAAGATATGGGAATTTATTATTGTCTACAGTATGATGAGTTT CCGTACACGTTCGGAGGGGGGACCAAGCAGGAAATAAAA (SEQ ID NO: 159) |
| | LE | GACATCCAGATGACTCAGTCTCCAGCCTCCCTATCTGCATCTGTGGG AGAAACTGTCACCATCACATGTCGAGCAAGTGAGAAAATTTACAGTT ATTTAGCATGGTATCAGCAGAAACAGGGAAAATCTCCTCAGCTCCTG GTCTATAATGCAAAAACCTTAGCAGAAGGTGTGCCATCAAGGTTCAG TGGCAGTGGATCAGGCACACAGTTTTCTCTGAAGATCAACAGCCTGC AGCCTGAAGATTTTGGGAGTTATTACTGTCAACATCATTATGTTACT CCGCTCACGTTCGGTGCTGGGACCAAGCTGGAGCTGAAA (SEQ ID NO: 160) |

Example 15: Cell Binding of Anti-PTGFRN Antibodies

Hek-293 #3 is a positive cell line stably transfected with PTGFRN cDNA. 33B7 and 4F4 bind significantly to Hek-293 PTG clone #3 (labeled as HEK-PTG #3 in Table 6) cells. Human cancer cells show different biding affinities for the two Abs. In addition, 4F4 binds different cell lines with various binding efficacy. The results are summaries in Table 6.

TABLE 6

Comparison of Binding of 33B7 and 4F4 to various human cell lines

| Cell type | 1st Ab | Flow binding | Cell type | 1st Ab | Flow binding |
|---|---|---|---|---|---|
| Daoy | IgG-0.1 ug | 720 | HEK-PTG-#3 | IgG-0.1 ug | 376 |
| Daoy | IgG-1 ug | 768.5 | HEK-PTG-#3 | IgG-1 ug | 379 |
| Daoy | 33B7-0.1 ug | 816 | HEK-PTG-#3 | 33B7-0.1 ug | 4172 |
| Daoy | 33B7-1 ug | 908 | HEK-PTG-#3 | 33B7-1 ug | 20300 |
| Daoy | 4F4-0.1 ug | 3456 | HEK-PTG-#3 | 4F4-0.1 ug | 10908 |
| Daoy | 4F4-1 ug | 12269.5 | HEK-PTG-#3 | 4F4-1 ug | 50318 |
| A431 | IgG-0.1 ug | 703 | MSTO-211H | IgG-0.1 ug | 625 |
| A431 | IgG-1 ug | 711 | MSTO-211H | IgG-1 ug | 626 |
| A431 | 33B7-0.1 ug | 685 | MSTO-211H | 33B7-0.1 ug | 634 |
| A431 | 33B7-1 ug | 803 | MSTO-211H | 33B7-1 ug | 657 |
| A431 | 4F4-0.1 ug | 8081 | MSTO-211H | 4F4-0.1 ug | 2094 |
| A431 | 4F4-1 ug | 31963.5 | MSTO-211H | 4F4-1 ug | 5962 |
| MDA231 | IgG-0.1 ug | 571 | H1299 | IgG-0.1 ug | 886 |
| MDA231 | IgG-1 ug | 575 | H1299 | IgG-1 ug | 852 |
| MDA231 | 33B7-0.1 ug | 571 | H1299 | 33B7-0.1 ug | 948 |
| MDA231 | 33B7-1 ug | 582 | H1299 | 33B7-1 ug | 863.5 |
| MDA231 | 4F4-0.1 ug | 1241 | H1299 | 4F4-0.1 ug | 978.5 |
| MDA231 | 4F4-1 ug | 2480 | H1299 | 4F4-1 ug | 1013 |

The binding of additional anti-PTGFRN antibodies to various cell lines are shown in FIGS. 12A-12D.

Example 16: Cell Killing Assay

CSB-INT positive clones were screened by a killing assay using indirect ADC on overexpressing or natural cancer cell lines. An exemplary protocol is provided below.

Killing Assay Protocol:

1. Prepare antibodies: Final concentration in each well is 1 nM. Prepare 2.5 nM (0.375 μg/ml) antibodies stock solution with culture media (DMEM+10% FBS), prepare enough Ab solution for 40 μl/well. mIgG (6.9 mg/ml in stock) is used as control.

Anti-H-PTGFRN mAbs: 7B4 (95.8 μg/ml; lot112217); purified 4F4 (0.94 μg/ul lot030818); 1B4 (120 μg/ml; lot112217); 1E2 (107 μg/ml; lot112217); 9A9 (49.6 μg/ml; lot112217); 9B11 (7.8 μg/ml; lot112217); 10D9 (120 μg/ml; lot112217); 10E6 (118 μg/ml; lot112217); 3E10 (120 μg/ml; lot112217); and 6F6 (30.4 μg/ml; lot112217). Anti-H-ICAM mAb: 5E11 (24.4 μg/ml; lot112617).

2. Prepare Fab-ZAP: Final concentration in each well is 9 nM. Prepare 4.5 μg/ml stock solution with culture media (DMEM+10% FBS), 20 μl/well. Fab-ZAP mouse is available from, for example, Advanced Targeting Systems (Cat #IT-48 Lot #130-10). The concentration of Fab-ZAP mouse is 1.9 mg/ml and 100 μg in total. Fab-ZAP mouse is aliquoted to 5 μl/tube and stored at −20 degree freezer.

3. Add 40 μl/well Abs and 20 μl/well Fab-ZAP onto 96-well flat-bottom plates and mix well, leave at room temperature (RT).

4. Prepare cells: Detach cells with 5 mM EDTA and resuspend cells in culture media, Count cell number and seed 2000 cells/40 µl/well onto plate.

5. Culture cells and check cells every day. Difference in viability may start to be visible at day 2. Stop the assay to check cell viability with CellTiter-Glo® (Promega, Madison, WI) at day 3.

6. At Day 3, remove media from the plate. Add prepared Cell-glo solution (Cell-glo 1:10 diluted with media) at 150 µl/well, mix and incubate at RT for 10 minutes. Transfer 90 µl/well to Costar® white plate, read Absorbance at 600 nm using SoftMax® Pro6.3 (Molecular Devices, LLC, San Jose, Calif.).

Figure 13A:
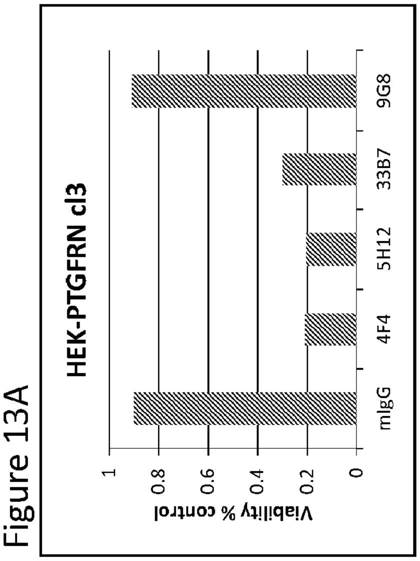
FIGS. 13A-13C show examples of killing assay efficacy.
Figure 13B:
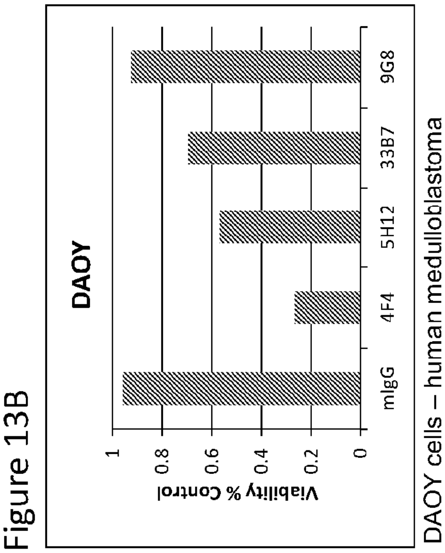
Figure 13C:
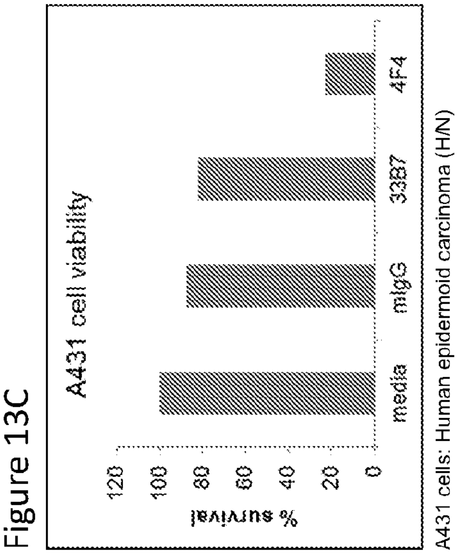
Figure 14A:
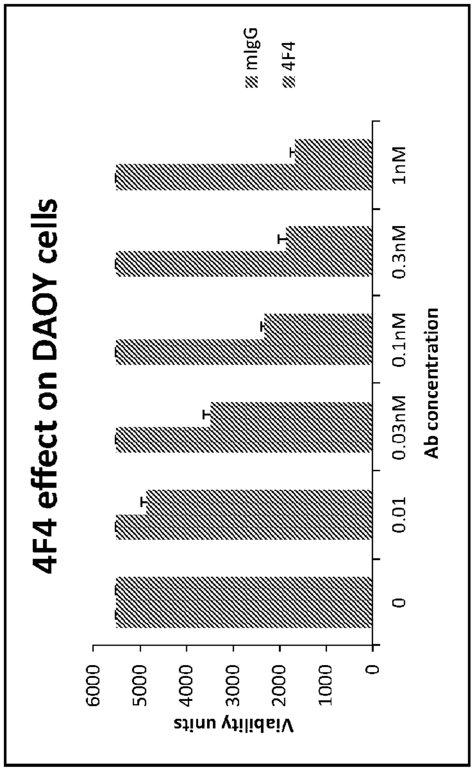
FIGS. 14A-14E show the cell-killing efficacy of multiple anti-PTGFRN mAbs on various cell lines. Specifically.
Figure 14B:
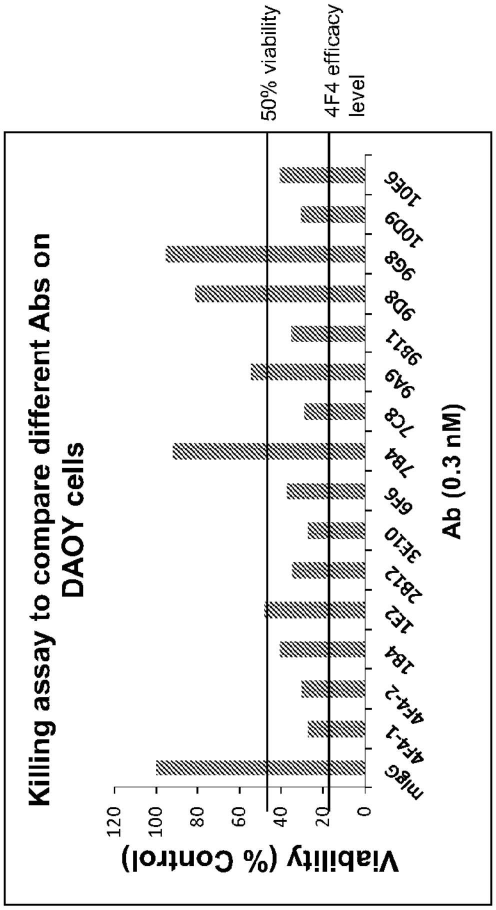
Figure 14C:
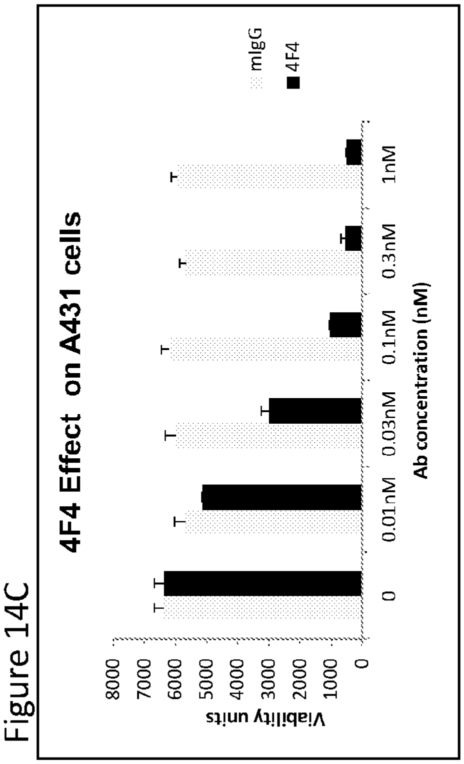
Figure 14D:
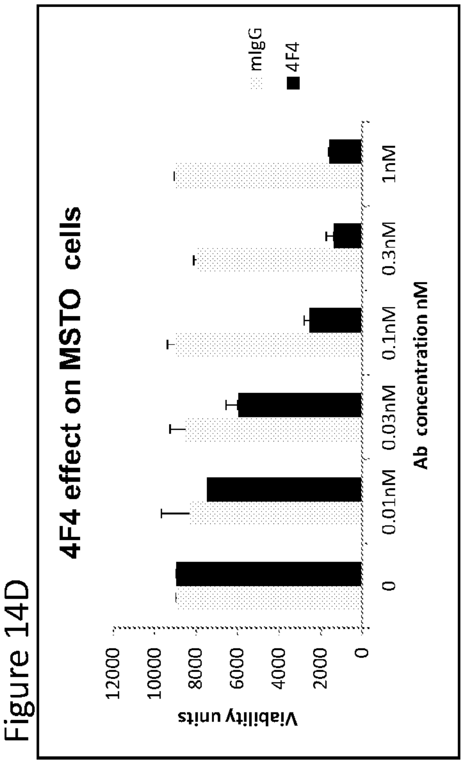
Figure 14E:
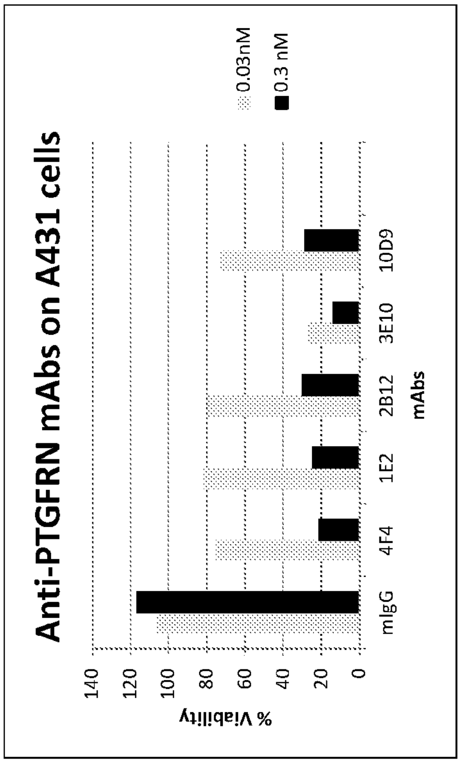

Using HEK cells that overexpress PTGFRN (HEK-293 PTG clone 3) in killing assays masks the gradation of response seen when the same antibodies are used in killing assay with naturally expressing PTGFRN cancer cell lines. An exemplary result is shown in FIG. 13A. Internalizing antibodies selected by killing assay were purified and tested on natural cancer cells. The natural cell lines highlight the high efficacy of the new antibodies compared to 33B7. Exemplary results are shown in FIGS. 13B and 13C. A dose response of antibody 4F4 on human medulloblastoma DAOY cells is shown in FIG. 14A. 4F4 is effective at a dose as low as 0.03 nM. In addition, the effects of various anti-PTGFRN antibodies on DAOY cells are shown in FIG. 14B. The upper line indicating 50% viability is used as cut point, i.e. any antibody unable to kill at least 50% cells was considered below requirement. The lower line indicates 4F4 efficacy level. 4F4-1 and 4F4-2 are different preparations of the same antibody. 9G8, a PTGFRN specific but not internalizing antibody, and mIgG (murine IgG) were used as negative controls. Assay has been repeated to show consistency. Nine antibodies in addition to 4F4 have been identified as good candidates in killing assay. Three antibodies (3E10, 7C8 & 10D9) have similar killing of DAOY cells to that of 4F4. Further, dose response of antibody 4F4 on A431 and MSTO cell lines are shown in FIG. 14C and FIG. 14D. 4F4 has an EC50 of 0.03 nM and 0.06 nM against A431 and MSTO cells, respectively. The EC50 of 33B7 is between 1 and 10 nM (data not shown). Thus, the data demonstrate that not only is 4F4 superior to 33B7 in its EC50, but also in its ability to kill cells derived from various cancer types, such as lung, prostate, and ovarian cancer cell lines. Additionally, FIG. 14E compares the cell-killing efficacy of anti-PTGFRN mAbs 4F4, 1E2, 2B12, 3E10, and 10D9, on A431 cell line at 0.03 nM and 0.3 nM of concentrations. As can be seen, in addition to 4F4, the other anti-PTGFRN mAbs, in particular, 3E10, are also effective in cell-killing at low nanomolar concentrations.

Example 17: Development of IHC Assay with PTGFRN Antibodies

Figure 15A:
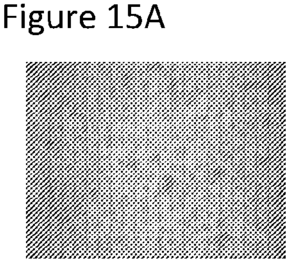
FIGS. 15A and 15B show an exemplary negative/low control slide (Hek293) and positive control slide (A431 cells), respectively, for immunohistochemistry (IHC) staining.
Figure 15B:
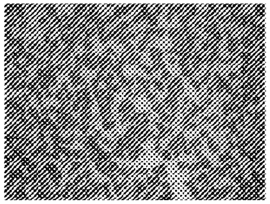

Ability to detect PTGFRN on tumor cells can be a good indicator to identify patients whose tumor will respond to anti-PTGFRN treatment, particularly anti-PTGFRN ADC treatment. Thus, anti-PTGFRN antibodies were investigated for their ability to detect PTGFRN protein in formalin fixed paraffin embedded (FFPE) tumor tissues. Hek PTG clone 3 or A431 human epidermoid carcinoma cells were used as positive control cells and Hek293 cells were used as the negative control. Exemplary negative and positive staining slides are shown in FIGS. 15A and 15B, respectively.

Figure 15C:
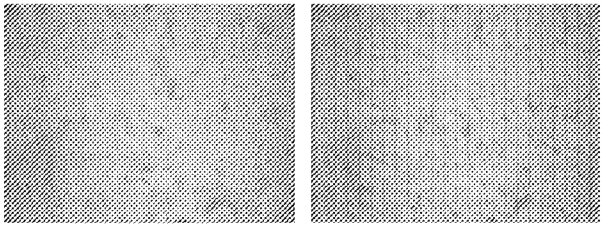
FIG. 15C shows the IHC staining of PTGFRN in mesothelioma tumors with 1B4 antibody. The upper panel shows the staining results in benign pleural mesothelioma and the lower panel shows the staining results in malignant pleural mesothelioma.
Figure 15C:
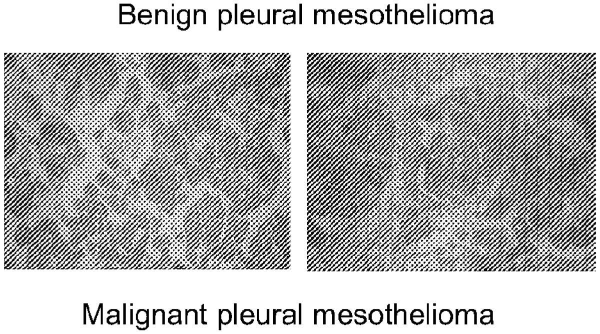

Selection of antibodies for immunohistochemistry (IHC) was first carried out with positive and negative cells on cytospin, followed by sections from cell pellets fixed and embedded in FFPE. Then the antibodies were assayed on tumor tissues (Tissue micro arrays). Several antibodies were qualified for use on IHC. An exemplary IHC staining of PTGFRN in mesothelioma tumors with 1B4 antibody is shown in FIG. 15C.

An IHC staining protocol is provided herein. Briefly, dissolve paraffin in xylene, rehydrate with 100% EtOH (3 times, 3 minutes each), 95% EtOH (3 times, 3 minutes each), and water. Antigen is retrieved at 95° C. and blocked with 5 mg/mL BSA in PBS (30 min at RT). Incubate with primary Antibody, e.g., 1B4, for 30 minutes at RT in 0.5 µg/mL in BSA-PBS solution. Then wash with PBS-T 3 times, 4 minutes each time. 1.5% H2O2 is used to block endogenous peroxidase. Incubate with anti-mouse IgG HRP-Polymer (e.g., from Vector Laboratories, Inc., Burlingame, CA) for 30 minutes at RT, 1 drop per slide, followed by washing with PBS-T 3 times, 4 minutes each time. Incubate with ImmPACT™ Chromogen Substrate (Vector Laboratories, Inc.) for 10 min and wash with H2O for 1 minute. Let slides dry completely. Then mount and proceed to the next steps.

Example 18: Determination of PTGFRN Binding Sites on Cancer Cells

Figure 16A:
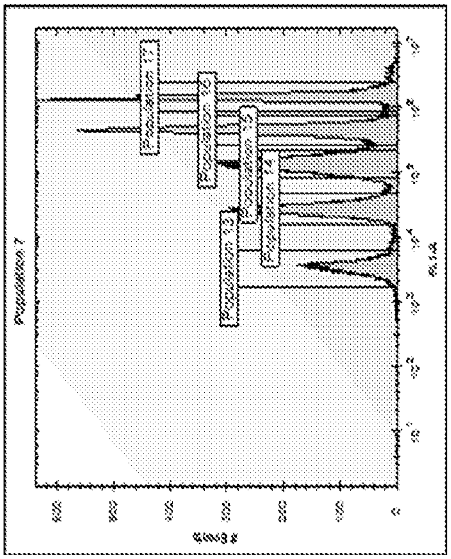
FIG. 16A shows the result of calibration using the QIFIKIT® to quantify the cell surface PTGFRN antigen on DAOY cell line.
Figure 16B:
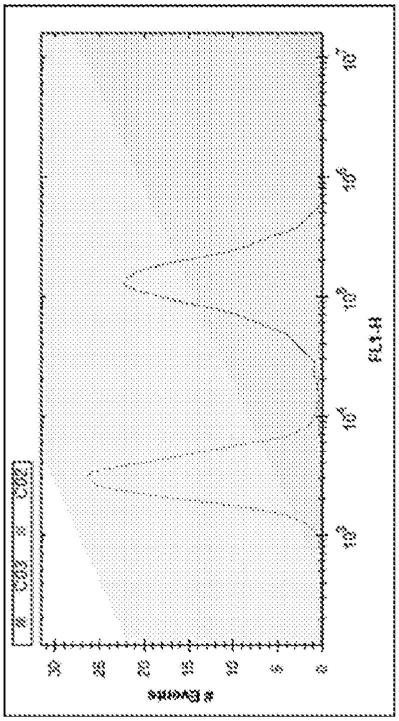
FIG. 16B is a histogram of mIgG and 4F4 (10 μg/ml) binding against DAOY Cells. The peak on the right (4F4) indicates >105 PTGFRN antigen/cell. The calibration panel and histogram results for 33B7 is shown in FIG. 16C.
Figure 16C:
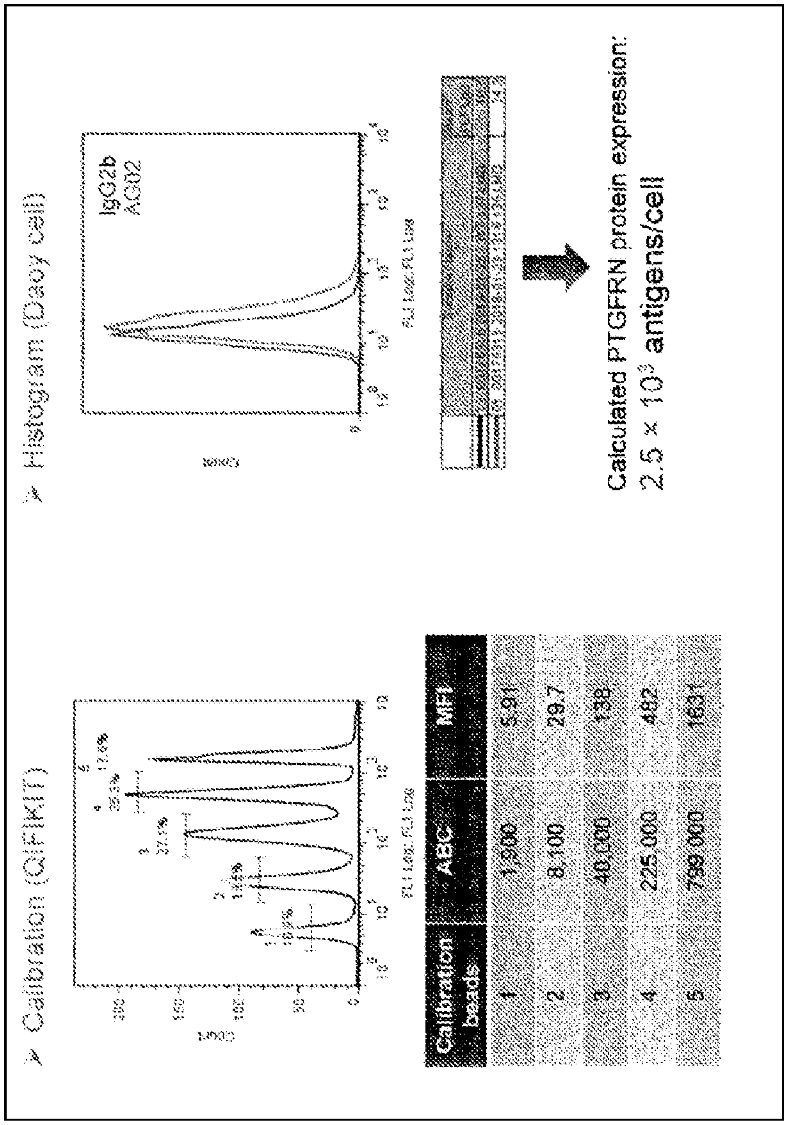

Using QIFIKIT® (Calibration panel, FIG. 16A), PTGFRN antigen (Ag) expression on DAOY cell line was investigated. The histogram (FIG. 16B) using 4F4 (10 µg/ml) (the peak on the right) with DAOY cells indicates >$10^5$ Ag/cell compared to $2.5\times10^3$ using 33B7 (FIG. 16C), a 65-fold improvement thereof. Using 4F4 in the same system with different cell lines indicates that several cancers express sufficient level of PTGFRN protein to be interesting as an ADC target. A summary is shown in Table 7.

TABLE 7

PTGFRN binding sites on cancer cell lines determined by QIFIKIT

| Cell lines | Cancer Type | H-PTGFRN sites/cell |
|---|---|---|
| A431 | Head & Neck | $1.9 \times 10^5$ |
| DAOY | Medulloblastoma | $1.4 \times 10^5$ |
| HS-578T | Squamous Basal TNBC | $7.7 \times 10^4$ |
| MSTO-211H | Mesothelioma | $2.6 \times 10^4$ |
| NCI-H520 | Squamous Lung | $1.3 \times 10^4$ |

As shown, PTGFRN is present in head & neck, lung, prostate and ovarian cancers and is a hot target for anticancer therapy. The multiple IgG1 and IgG2 PTGFRN antibodies developed herein are Western Blot and IHC capable. They are either internalizing or non-internalizing. These antibodies demonstrate potential to be used in in vitro diagnostic assays or kits to identify patients for treatment, in vivo imageable diagnostic assays or kits to identify tumor sites, and/or druggable antibodies or antibody-drug conjugates to treat cancer selectively.

Of the 44 antibodies that killed >50% of DAOY cells, 10 candidates were selected and assessed for binding and killing efficacy with several cancer cell lines. Cell lines tested by Flow and killing assays include PC-3 (Prostate castrate resistant), MSTO 211H (Mesothelioma), DAOY (Medulloblastoma), A431 (epidermoid carcinoma), TOV21G (ovarian clear cells), NCI-H520 (Lung Cancer), FaDu (Head & Neck pharyngeal), and MDA 231 (Triple Neg Breast).

Figure 17A:
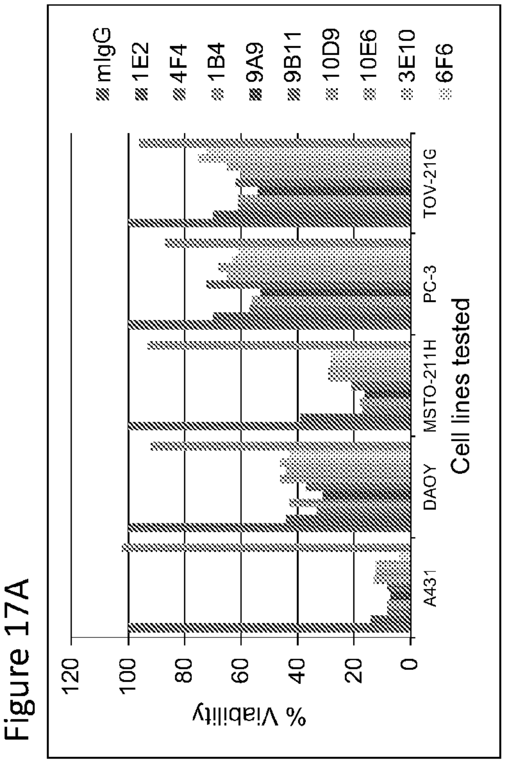
FIGS. 17A and 17B show the cell-killing efficacy of selected anti-PTGFRN mAbs on multiple human cancer cell lines.
Figure 17B:
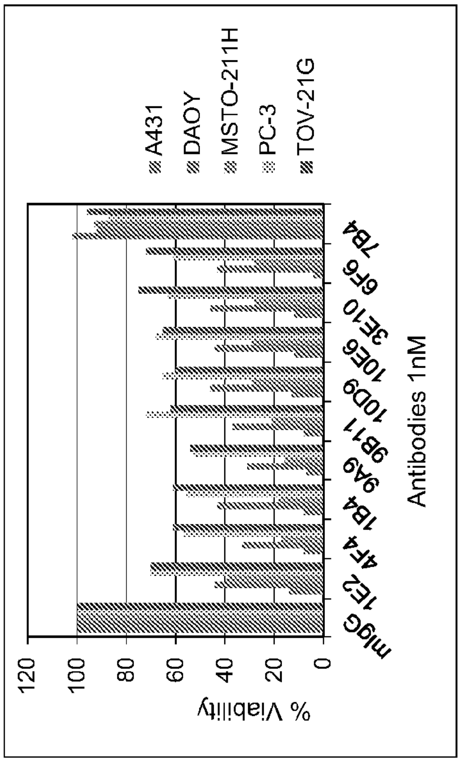

Example 19: Cell Killing Activity of Selected Anti-PTGFRN Antibodies on Cancer Cell Lines Selected anti-PTGFRN antibodies were tested on several human cancer cell lines for cell killing activity. All candidates showed different levels of killing against the various cell lines tested except that MDA231 is PTGFRN negative and acted as a negative control. The results are shown in FIGS. 17A and 17B. Antibodies 4F4 (IgG2) and 3E10 (IgG1), for example, show favorable activities both in the level of killing and in the number of different cancers susceptible to killing. The results of 4F4 mAb flow binding and killing assays on various cancer cell lines are summarized in Table 8.

TABLE 8

4F4 Mab Flow Binding and Killing Assays on Cancer Cell Lines

| Cell name | Cell type | Flow Binding[+] | Viability* % control |
|---|---|---|---|
| MDA-MB-231 | Breast adeno | Neg | 97 |
| HS-578T | Breast Squam. Basal | 30,000 | 50 |
| A431 | H&N squamous | 110,000 | 10 |
| FaDu | H&N | 55,000 | 60 |
| PC3 | Cast. Res Prostate | 20,000 | 57 |
| MSTO-211H | Mesothelioma | 30,000 | 25 |
| DAOY | Medulloblastoma | 64,000 | 30 |
| SK-LMS-1 | Leiomyosarcoma | Neg | 100 |
| H520 | Lung squamous | 14,000 | 60 |
| H1299 | Lung adeno | Neg | 100 |
| TOV-21G | Ovarian, clear cell | 45,000 | 54 |
| BXPC3 | Pancreas | 60,000 | ND** |

[+]Flow assay 4F4 assayed at 1 μg/ml.
*Viability assay 4F4 assayed at 1 nM in Fab-ZAP assay.
**Not Defined.

Example 20: Octet-Based Binding Characteristics of Anti-PTGFRN Mabs

Antibody scouting/affinity based antibody ranking was performed to determine on/off rates and KD ranking of selected anti-PTGFRN mAbs using AMC sensor on forteBio Octet® Red96 (ForteBio, Menlo Park, Calif.). PTGFRN-ECD, 100 nM, was used as the analyte. The Kinetic Rates and Equilibrium Binding Constants of the assessed antibodies are summarized in Table 9. Thirteen candidates have improved affinity compared with 33B7. 9G8 was found not to internalize and 9D8 was found to internalize poorly. 4F4 has approximately 1000-fold better affinity (KD) and increased binding activity (response) than 33B7. Twelve antibodies have similar KD to 4F4.

TABLE 9

Octet-based Binding Characteristics of anti-PTGFRN mAbs

| Clone # | Response | KD (M) | kon (I/Ms) | kdis (1/s) | Full $\chi 2$ | Full R2 |
|---|---|---|---|---|---|---|
| 4F4 | 0.5984 | <1.0E−12 | 1.30E+05 | <1.0E−07 | 0.0609 | 0.9936 |
| 33B7 | 0.2447 | 3.09E−09 | 1.95E+05 | 6.02E−04 | 0.0451 | 0.9392 |
| 7B4 | 0.2416 | 8.38E−09 | 8.02E+04 | 6.72E−04 | 0.0077 | 0.9948 |
| 2B12 | 0.2717 | <1.0E−12 | 4.85E+04 | <1.0E−07 | 0.0189 | 0.9944 |
| 9A9 | 0.3192 | <1.0E−12 | 1.51E+05 | <1.0E−07 | 0.0245 | 0.9898 |
| 6F6 | 0.3349 | <1.0E−12 | 6.91E+04 | <1.0E−07 | 0.0407 | 0.9910 |
| 10D9 | 0.3416 | <1.0E−12 | 8.56E+04 | <1.0E−07 | 0.0497 | 0.9877 |
| 1E2 | 0.4104 | <1.0E−12 | 6.38E+04 | <1.0E−07 | 0.0209 | 0.9970 |
| 9B11 | 0.4704 | <1.0E−12 | 1.80E+05 | <1.0E−07 | 0.0274 | 0.9940 |
| 3E10 | 0.4725 | <1.0E−12 | 1.20E+05 | <1.0E−07 | 0.0271 | 0.9955 |
| 10E6 | 0.5316 | <1.0E−12 | 1.02E+05 | <1.0E−07 | 0.0460 | 0.9949 |
| 7C8 | 0.5829 | <1.0E−12 | 1.08E+05 | <1.0E−07 | 0.0368 | 0.9965 |
| 1B4 | 0.5879 | <1.0E−12 | 9.79E+04 | <1.0E−07 | 0.1028 | 0.9914 |
| 9G8 | 0.3500 | <1.0E−12 | 6.94E+04 | <1.0E−07 | 0.0331 | 0.9932 |
| 9D8 | 0.4207 | <1.0E−12 | 1.12E+05 | <1.0E−07 | 0.0267 | 0.9950 |

*$\chi 2$ is chi square analyzed the closeness between raw data and calculated data. <2 indicate a good fit.
*R2 is a statistical measure of how close the data are to the fitted regression line. 1 indicates a perfect fit. 0.99 is excellent.

Further, pairing analysis of 15 Abs with PTGFRN-ECD based on the epitope binning/pairing data from Octet® Red96 (binning matrix, FIG. 18) indicate that the 15 antibodies can be grouped into 4 epitope bins as following: Bin #1: 10D9, 2B12, 7C8, 7B4, 9A9, 9G8; Bin #2: 1B4, 3E10, 6F6, 9B11, 4F4, 33B7; Bin #3: 1E2; and Bin #4: 10E6. Each Bin is reflective of a discrete epitope. Both 4F4 and 33B7 antibodies recognize the same epitope.

In conclusion, the 33B7 antibody had effect on hamster spindle cell carcinoma where the binding by Flow and cell killing activity with indirect ADC were shown. See Examples 7, 9, and 10. However, in human cancer cell lines, the flow assay even with triple amplification showed little cell surface binding with 33B7. Further, the killing effect was observable when 33B7 was directly conjugated to Saporin and added at 10 nM, which was also demonstrated by in vivo studies on mouse xenografts models. The cells where 33B7-ADC showed activities in addition to hamster spindle cell carcinoma were A431 human epidermoid carcinoma and MSTO-211H human biphasic mesothelioma.

Therefore, it is unexpected that the anti-human PTGFRN mAbs showed that they could significantly bind to many cancer cell lines by Flow binding assay. Further, it is unexpected that the internalizing antibodies can kill many cancer cell lines using indirect ADC with FAB-ZAP at concentrations with optimal effect at as low as 0.3 nM, in particular some of these mAbs are grouped in the same epitope bin as 33B7. The concentration is at least 30-fold lower than the concentration of direct 33B7-ADC that had killing effect.

Additionally, Octet® binning assay with recombinant PTGFRN show that the antibodies can be separated into 4 groups based on their epitope recognition with some antibodies having shared epitope with 33B7 and some antibodies having different epitopes than 33B7.

It is to be appreciated that the Detailed Description section, and not the Summary and Abstract sections, is intended to be used to interpret the claims. The Summary and Abstract sections set forth one or more, but not all, exemplary embodiments of the present disclosure as contemplated by the inventor(s), and thus, are not intended to limit the present disclosure and the appended claims in any way.

The present disclosure has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary embodiments, but should be defined only in accordance with the following claims and their equivalents.

What is claimed is:

1. A conjugate comprising an antibody and a functional moiety joined by a linker, the antibody being an isolated antibody or antigen binding fragment thereof that specifically binds to prostaglandin F2 receptor inhibitor (PTGFRN), comprising:

a) a heavy chain variable region comprising the CDR sequences SEQ ID NOs: 8, 9 and 10 and a light chain variable region comprising CDR sequences SEQ ID NOs: 5, 6 and 7;

b) a heavy chain variable region comprising the CDR sequences SEQ ID NOs: 11, 12 and 13 and a light chain variable region comprising CDR sequences SEQ ID NOs: 20, 21 and 22; or c) a heavy chain variable region comprising the CDR sequences SEQ ID NOs: 35, 36 and 37 and a light chain variable region comprising CDR sequences SEQ ID NOs: 38, 39 and 40.

2. The conjugate of claim 1, wherein the functional moiety is a cytotoxic reagent.

3. The conjugate of claim 2, wherein the cytotoxic reagent is selected from the group consisting of a nucleoside antagonist, an intercalating agent, a microtubule assembly inhibitor, a folate inhibitor, a ribosome inactivating protein, and a toxin.

4. The conjugate of claim 1, wherein the linker is selected from the group consisting of a cleavable linker, a non-cleavable linker, a hydrophilic linker, and a dicarboxylic acid based linker.

5. The conjugate of claim 1, wherein the conjugate is internalized by a PTGFRN expressing cell.

6. The conjugate of claim 1, wherein said antibody or antigen binding fragment thereof is murine, humanized, or chimeric.

7. The conjugate of claim 1, wherein said antibody or antigen binding fragment thereof comprises an IgG1 or IgG2 constant region.

8. A method for inducing cytotoxicity in a cell expressing PTGFRN comprising contacting the cell with a conjugate of claim 1.

9. The conjugate of claim 3, wherein the cytotoxic reagent is a toxin.

10. The conjugate of claim 3, wherein the cytotoxic reagent is a nucleoside antagonist.

11. The conjugate of claim 3, wherein the cytotoxic reagent is a microtubule assembly inhibitor.

12. The conjugate of claim 11, wherein the microtubule assembly inhibitor is a vinca alkaloid.

13. The conjugate of claim 3, wherein the cytotoxic reagent is a folate inhibitor.

14. The conjugate of claim 3, wherein the cytotoxic reagent is a ribosome inactivating protein.

15. The conjugate of claim 14, wherein the ribosome inactivating protein is saporin.

16. The conjugate of claim 10, wherein the nucleoside antagonist is selected from the group consisting of 5-fluorouracil, 6-mercaptopurine, arabinosylcytosine, capecitabine, clofarabine, cytarabine, dacarbazine, fludarabine, gemcitabine and nelarabine.

17. The conjugate of claim 3, wherein the cytotoxic reagent is an intercalating agent.

18. The conjugate of claim 17, wherein the intercalating agent is selected from the group consisting of oxaliplatin, cisplatin and carboplatin.

19. The conjugate of claim 11, wherein the microtubule assembly inhibitor is an auristatin.

20. The conjugate of claim 19, wherein the auristatin is selected from the group consisting of monomethyl auristatin E and monomethyl auristatin F.

21. The conjugate of claim 11, wherein the microtubule assembly inhibitor is a taxane.

22. The conjugate of claim 21, wherein the taxane is selected from the group consisting of a docetaxel and paclitaxel.

23. The conjugate of claim 12, wherein the vinca alkaloid is selected from the group consisting of vindesine, vincristine, vinorelbine and vinblastine.

24. The conjugate of claim 11, wherein the microtubule assembly inhibitor is a maytansinoid.

25. The conjugate of claim 11, wherein the microtubule assembly inhibitor is ixabepilone.

26. The conjugate of claim 9, wherein the toxin is selected from the group consisting of ricin and cholera toxin.

27. The conjugate of claim 13, wherein the folate inhibitor selected from the group consisting of methotrexate and pemetrexed.

28. The conjugate of claim 3, wherein the cytotoxic agent is selected from the group consisting of an anthracycline, a camptothecin, a combretastatin, a dolastatin, a duocarmycin, an enediyne, a geldanamycin, an indolino-benzodiazepine dimer, a maytansine, a puromycin, a pyrrolobenzodiazepine dimer, a taxane, a vinca alkaloid, a tubulysin, a hemiasterlin, a spliceostatin, a pladienolide, a calicheamicin, a monomethyl auristatin a E, monomethyl auristatin F, a maytansinoid DM1, a maytansinoid DM4, calicheamicin, ozogamicin, α-amanitin, yttrium-90, and iodine-131.

29. The conjugate of claim 24, wherein the maytansinoid is a mertansine.

* * * * *